US 11,446,345 B2
Sep. 20, 2022

(12) United States Patent
Hu et al.

(10) Patent No.: US 11,446,345 B2
(45) Date of Patent: Sep. 20, 2022

(54) THERAPEUTIC AGENTS AND USES THEREOF FOR DRUGS FOR TREATMENT OF TUMORS AND/OR CANCERS

(71) Applicant: HANGZHOU CONVERD CO., LTD., Hangzhou (CN)

(72) Inventors: Fang Hu, Hangzhou (CN); Lin Chen, Hangzhou (CN); Ronghua Zhao, Hangzhou (CN)

(73) Assignee: HANGZHOU CONVERD CO., LTD., Hangzhou (CN)

(*) Notice: Subject to any disclaimer, the term of this patent is extended or adjusted under 35 U.S.C. 154(b) by 410 days.

(21) Appl. No.: 16/474,349

(22) PCT Filed: Jan. 3, 2018

(86) PCT No.: PCT/CN2018/070166
§ 371 (c)(1),
(2) Date: Jun. 27, 2019

(87) PCT Pub. No.: WO2018/127052
PCT Pub. Date: Jul. 12, 2018

(65) Prior Publication Data
US 2019/0336549 A1 Nov. 7, 2019

(30) Foreign Application Priority Data
Jan. 4, 2017 (CN) .......................... 201710003954.1

(51) Int. Cl.
*A61K 35/761* (2015.01)
*A61P 35/00* (2006.01)
*A61K 35/17* (2015.01)
*A61K 35/768* (2015.01)
*A61K 35/763* (2015.01)
*A61K 35/765* (2015.01)
*A61K 35/766* (2015.01)
*A61K 35/76* (2015.01)

(52) U.S. Cl.
CPC ............ *A61K 35/761* (2013.01); *A61K 35/17* (2013.01); *A61K 35/763* (2013.01); *A61K 35/765* (2013.01); *A61K 35/766* (2013.01); *A61K 35/768* (2013.01); *A61P 35/00* (2018.01); *A61K 35/76* (2013.01); *C12N 2710/10032* (2013.01); *C12N 2710/24132* (2013.01)

(58) Field of Classification Search
CPC .................................................. A61K 35/761
See application file for complete search history.

(56) References Cited

U.S. PATENT DOCUMENTS 10,064,893 B2   9/2018   Contag et al.
10,434,169 B2   10/2019  Kim et al.
10,612,005 B2 * 4/2020   Coffin ................ C07K 16/2818
2007/0077231 A1  4/2007  Contag et al.
2016/0339066 A1  11/2016 Szalay et al.
2018/0100053 A1  4/2018  Jing et al.
2019/0167641 A1  6/2019  Yan et al.
2020/0264190 A1  8/2020  Gimenez et al.

FOREIGN PATENT DOCUMENTS

CN       105307671 A      2/2016
CN       106177961 A      12/2016
JP       2014502970 A     2/2014
JP       2019536062 A     12/2019
JP       2019536075 A     12/2019
WO       2016/009017 A1   1/2016
WO       2016008976 A1    1/2016
WO       2016146894 A1    9/2016
WO       2016164370 A1    10/2016
WO       WO2016/164370    * 10/2016    ............. A61K 39/00

OTHER PUBLICATIONS

Chen et al. (Oncotarget, vol. 7, No. 19, pp. 27764-27777 [Apr. 1, 2016]) (Year: 2016).*
Oncolytic HSV-1 rQNestin34.5v2 (NCI thesaurus, downloaded Jan. 10, 2022) (Year: 2022).*
Yoo et al. (Clin Cancer Res. Nov. 1, 2016;22(21):5265-5276. doi: 10.1158/1078-0432.CCR-16-1003. Epub Jul. 7, 2016) (Year: 2016).*
Russell et al. (Nature Biotechnology vol. 30, pp. 658-670 (2012)). (Year: 2012).*
Vasey et al. (J Clin Oncol 20:1562-1569 (2002)) (Year: 2002).*
International Search Report and Written Opinion dated Apr. 4, 2018, for corresponding International Patent Application No. PCT/CN2018/070172.
Danyang Li et al.; The Progress of Oncolytic Vaccinia Viruses Modified Genetically for the Tumor Treatment; Chinese Journal of Cell Biology; Dec. 31, 2016; vol. 38, No. 12; pp. 1523-1534.
Zhihua Wang; Research progress of clinical transplation in NK cells against tumor; Chinese Journal of Cancer Biotherapy; Jun. 30, 2016; vol. 23, No. 3; pp. 419-426.
Limei Zhao; Research on Vaccinia Virus-based Oncolytic Virus and Oncolytic Effect thereof; Master's Dissertation of Nankai University; May 31, 2014.
First Office Action dated Oct. 29, 2018, for Chinese Patent Application No. 201710003954.1.
Extended European Search Report issued by EUIPO for corresponding European patent application No. 18736087.0 dated Jun. 25, 2020.
Tai et al.; "Preventing Postoperative Metastatic Disease by Inhibiting Surgery-Induced Dysfunction in Natural Killer Cells," Cancer Research; vol. 73, No. 1; pp. 97-107; Jan. 1, 2013.
Tai et al.; "Attacking postoperative metastases using perioperative oncolytic viruses and viral vaccines;" Frontier in Oncology 2014 Frontiers Research Foundation; vol. 4; Aug. 2014.

(Continued)

*Primary Examiner* — Scott Long
(74) *Attorney, Agent, or Firm* — Renner, Otto, Boisselle & Sklar, LLP

(57) ABSTRACT

The present disclosure provides therapeutic agents and uses thereof for drugs for treatment of tumors and/or cancers. The active ingredients of the therapeutic agents comprise an oncolytic virus that selectively replicate in tumor cells and comprise NK cells.

15 Claims, 34 Drawing Sheets

(56) References Cited

OTHER PUBLICATIONS

PCT/CN2018/070166; PCT International Search Report and Written Opinion of the International Searching Authority dated Apr. 4, 2018.
First Office Action dated Oct. 26, 2021, for corresponding Japanese Patent Application No. 2019-536062.
First Office Action dated Oct. 26, 2021, for corresponding Japanese Patent Application No. 2019-536075.
Extended European Search Report dated Nov. 5, 2020 for application No. 18736473.2.
Tai Lee-Hwa et al:"Preventing Postoperative Metastatic Disease by inhibiting Surgery-Induced Dysfunction in Natural Killer Cells", Cancer Research, vol. 73, No. 1, Jan. 1, 2013, pp. 97-107, ISSN:0008-5472(print).
Tai L -H et al:"Attacking postoperative metastases using perioperative oncolytic viruses and viral vaccines", Frontiers in Oncology 2014 Frontiers Research Foundation CHE, vol. 4 AUG, 2014,XP9520984, ISSN: 2234-943X.
Second Office Action dated Apr. 26, 2022, for corresponding Japanese Patent Application No. 2019-536062.
Second Office Action dated Apr. 26, 2022, for corresponding Japanese Patent Application No. 2019-536075.
Hiroshi Ternuma et al.; BIO Clinica; News from Industry; Jan. 2016; pp. 55-61, 108; vol. 31, No. 1.
Keerthana Shankar et al.; Genome engineering of induced pluripotent stem cells to manufacture natural killer cell therapies; Stem Cell Research & Therapy; 2020; pp. 1-14.

* cited by examiner

THERAPEUTIC AGENTS AND USES THEREOF FOR DRUGS FOR TREATMENT OF TUMORS AND/OR CANCERS

This application is a national phase entry under 35 U.S.C. § 371 of International Patent Application No. PCT/CN2018/070166 filed on Jan. 3, 2018, which claims priority to Chinese Patent Application No. 201710003954.1, filed on Jan. 4, 2017, which is incorporated herein by reference in its entirety.

FIELD OF THE INVENTION

The present invention relates to the field of biotechnology, and particularly to a therapeutic agent and use thereof for drugs for treatment of tumors and/or cancers.

BACKGROUND OF THE INVENTION

Malignant tumors are among the leading causes of death in human diseases, and the main therapeutic methods thereof are surgery, radiotherapy and chemotherapy. Biological therapy for tumors has been developed in recent years and is called the fourth modality of malignant tumor treatment, which includes tumor vaccine therapy, non-specific tumor immunotherapy, targeted immunotherapy with monoclonal antibodies, cytokine therapy, adoptive cellular immunotherapy, tumor gene therapy, etc. Cancer virotherapy also belongs to biological therapy, and has been advancing rapidly in the last 20 years. At present, one of the most significant progresses in virotherapy is that some viruses can be structurally modified based on the difference between normal cells and cancer cells, such that they can replicate selectively in tumor cells and ultimately kill those tumor cells. These modified viruses originated from adenovirus, herpesvirus, poxvirus, etc., and are collectively called as 'oncolytic viruses' based on their function. It has been discovered that some wild-type viruses can also replicate selectively in and lyse tumor cells.

The ingredient in H101, which is an oncolytic virus injection approved for sale in China, is a genetically modified adenovirus type 5 that can preferably replicate in tumor cells. For H101, the E1B 55KD gene and E3 regions were mainly deleted from a human adenovirus type 5, which leads H101 to achieve the ability to selectively replicate in and eventually lyse tumor cells. One of the mechanisms of action thereof is that the 55KD protein encoded in E1B region in a wild-type adenovirus can combine with p53 protein, so as to inhibit the clearance of the adenovirus by p53 gene. Because the oncolytic virus cannot express E1B-55KD protein, it can't replicate in cells with functional p53 gene. However, in tumor cells with p53 gene mutation, which have no inhibitory function of p53 gene, the virus can replicate massively. In addition, the deletion of E3 region allows the virus to be recognized and cleared by the immune system (for example, NK cells), which increases the safety of the virus for clinical application. The current opinion is that, not only the mutation of p53 gene but also any defects in the p53 pathway can promote the selective replication of H101. By intratumoral administration, H101 can replicate massively in tumor cells, ultimately causing lysis and death of tumor cells.

The ingredient of T-Vec, which is an oncolytic virus approved for sale by the FDA in U.S., is a genetically modified herpes simplex virus type 1 (HSV-1). The ICP34.5 gene and ICP47 gene were deleted from T-Vec, while a gene for granulocyte-macrophage colony-stimulating factor (GM-CSF), i.e., a human immunostimulating protein, was inserted into T-Vec, such that it can replicate in tumor cells and express GM-CSF. After being injected into melanoma lesions, it can lyse the tumor cells, causing them to burst, and at the same time release tumor-associated antigens and GM-CSF, which promote anti-tumor immune response, although the mechanism has not yet been elucidated by Amgen Inc. On Oct. 27, 2015, FDA approved T-Vec for the local treatment of unresectable melanoma lesions in patients with melanoma recurrence after initial surgery.

Vaccinia virus has a relatively large size and an oncolytic vaccinia virus obtained by genetic modification of a wild-type one may replicate in tumor cells with significantly increased selectivity. In some of these oncolytic vaccinia viruses, the thymidine kinase (TK) gene was deleted from the viral DNA, such that the oncolytic virus cannot replicate or proliferate in normal cells. Unlike normal cells, tumor cells can synthesize thymidine kinase, which can be provided to the oncolytic vaccinia virus for its replication, therefore the oncolytic virus can replicate massively in tumor cells. In addition, the vascular growth factor (VGF) gene was deleted in certain oncolytic vaccinia viruses, so as to increase their tumor-specific proliferation and eventually cause lysis and death of tumor cells. Further, both TK gene and VGF gene were deleted in certain oncolytic vaccinia viruses. By far, no oncolytic vaccinia virus has been approved for sale. Compared to the oncolytic viruses based on adenovirus or herpesvirus, the oncolytic vaccinia virus has the advantage that it can be systemically administered by intravenous injection to reach tumor sites. Furthermore, the vaccinia virus has a large genome, which allows for genetic modification aiming to increase its tumor-killing effect.

However, when used as a monotherapy for tumors, sometimes the oncolytic viruses do not show satisfactory effectiveness; and when oncolytic viruses were combined with chemotherapeutic agents for the treatment of tumors, serious adverse effects can occur because chemotherapeutic agents also damage normal cells.

NK cells (natural killer cells) are a type of non-specific innate immune cells produced in bone marrow and exist in almost all the organs in human body. They are uniformly identified as $CD3^-/CD56^+$ and can be divided into two sub-types, i.e., $CD16^-/CD56^{bright}$ and $CD16^+/CD56^{dim}$, which have in vivo functions of immune regulation and tumor killing, respectively. NK cells don't have MHC class I antigenic determinants, so there is little to no risk for immune responses against normal cells of hosts (GvHD). In vitro expanded NK cells have the advantages that the quality testing can be easily conducted, and the cells can be used allogeneically. Although the number of NK cells in human body is less than that of T cells, NK cells respond faster, functioning as a sentry and capable of killing cancer cells directly, especially relatively small cancer foci, which can be the source of metastasis and cause of relapse. NK cells can also kill tumor cells in the circulatory system. NK cells can also inhibit viruses; for example, hepatitis B virus and herpes virus causing cervical cancer, and they can clear aged cells as well. However, NK cells kill cancer cells and viruses in a non-specific fashion; therefore, the effectiveness of monotherapy with NK cells to treat cancer is yet to be improved. Although currently, various combination therapies of NK cells and monoclonal antibodies have been developed and showed therapeutic effect, the application of such combination therapies was limited due to off-target effects of the monoclonal antibodies.

There is still a need for more effective treatment regimens and drugs developed therefor in the immunotherapy of tumors and/or cancers.

SUMMARY OF THE INVENTION

In order to solve the above-mentioned problems in the art, the present disclosure provides therapeutic agents, pharmaceutical compositions, kits, uses thereof for drugs for the treatment of tumors and/or cancers, and methods for the treatment of tumors and/or cancers. The therapeutic agents, compositions, methods and kits may be embodied in a variety of ways.

In an embodiment, provided is a therapeutic agent or pharmaceutical composition, comprising: (a) a first pharmaceutical composition comprising an oncolytic virus in a first pharmaceutically acceptable carrier; and (b) a second pharmaceutical composition comprising NK cells in a second pharmaceutically acceptable carrier; wherein the oncolytic virus can selectively replicate in tumor cells.

In another embodiment, provided is the use of the therapeutic agent or pharmaceutical composition for preparation of drugs for treatment of tumors and/or cancers.

In yet another embodiment, provided is a kit of combinational drugs with synergistic effects for treatment of tumors and/or cancers, comprising a first container containing an oncolytic virus and a second container containing NK cells, wherein the first container is separate from the second container; and instructions specifying timing and routes of administration; wherein the oncolytic virus can selectively replicate in tumor cells.

In still another embodiment, provided is a method for treating a tumor and/or cancer, comprising the following steps in a sequential manner: 1) administering an oncolytic virus to a tumor and/or cancer patient, wherein the oncolytic virus can selectively replicate in tumor cells; and 2) 18 to 72 hours after the administration of the oncolytic virus, administering NK cells to the tumor and/or cancer patient.

Specifically, the present disclosure provides:

In an aspect, provided is a pharmaceutical composition, wherein the active ingredients of the pharmaceutical composition comprise an oncolytic virus and NK cells, and wherein the oncolytic virus can selectively replicate in tumor cells. Preferably, the active ingredients of the pharmaceutical composition consist of the oncolytic virus and the NK cells In some examples, the oncolytic virus and the NK cells are present separately in the pharmaceutical composition without being mixed together.

In certain embodiments, the pharmaceutical composition may comprise the oncolytic virus at a therapeutically effective dose, and may comprise the NK cells at a dose ranging from $1\times10^7$ to $1\times10^{10}$ cells/day.

In some embodiments, the oncolytic virus is selected from genetically mutated viruses with oncolytic abilities and wild-type viruses with oncolytic abilities. Preferably, the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

In some embodiments, the NK cells are selected from autologous NK cells and allogeneic NK cells. Preferably, the NK cells are in vitro expanded autologous NK cells or in vitro expanded allogeneic NK cells.

The oncolytic virus of the pharmaceutical composition may be administered via intratumoral injection or administered intravenously, and the NK cells may be administered intravenously.

In certain embodiments, the oncolytic virus of the pharmaceutical composition is an oncolytic adenovirus. In some examples, E1 region and/or E3 region of the oncolytic adenovirus are/is genetically modified. In some examples, the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

In certain embodiments, the active ingredients of the pharmaceutical composition comprise an oncolytic adenovirus at a dose ranging from $5\times10^7$ to $5\times10^{12}$ VP/day, and the NK cells at a dose ranging from $1\times10^7$ to $1\times10^{10}$ cells/day. Preferably, the active ingredients of the pharmaceutical composition consist of an oncolytic adenovirus at a dose ranging from $5\times10^7$ to $5\times10^{12}$ VP/day, and the NK cells at a dose ranging from $1\times10^7$ to $1\times10^{10}$ cells/day.

In certain embodiments, the active ingredients of the pharmaceutical composition comprise the oncolytic virus H101, and the NK cells at a dose ranging from $1\times10^9$ to $3\times10^9$ cells/day. Preferably, the active ingredients of the pharmaceutical composition consist of the oncolytic virus H101, and the NK cells at a dose ranging from $1\times10^9$ to $3\times10^9$ cells/day.

In another aspect, provided is the use of the pharmaceutical composition for preparation of drugs for treatment of tumors and/or cancers.

The tumors and/or cancers may include lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia.

Also provided is a therapeutic agent. In an embodiment, the therapeutic agent may comprise: (a) a first pharmaceutical composition comprising an oncolytic virus in a first pharmaceutically acceptable carrier; and (b) a second pharmaceutical composition comprising NK cells in a second pharmaceutically acceptable carrier; wherein the oncolytic virus can selectively replicate in tumor cells.

The first pharmaceutically acceptable carrier may be either the same as or different from the second pharmaceutically acceptable carrier.

In some embodiments, the first pharmaceutical composition and the second pharmaceutical composition are present separately in the therapeutic agent without being mixed together. In an embodiment, the active ingredient of the first pharmaceutical composition is the oncolytic virus, and the active ingredient of the second pharmaceutical composition is the NK cells.

Various dose levels may be applied as appropriate. In certain embodiments, the first pharmaceutical composition comprises the oncolytic virus at a therapeutically effective dose, and the second pharmaceutical composition comprises the NK cells at a dose ranging from $1\times10^7$ to $1\times10^{10}$ cells/day.

Various oncolytic viruses may be applied as appropriate. In certain embodiments, the oncolytic virus is selected from genetically mutated viruses with oncolytic abilities and wild-type viruses with oncolytic abilities. For example, the oncolytic virus may be selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

Various NK cells may be applied as appropriate. In certain embodiments, the NK cells are selected from autologous NK cells and allogeneic NK cells. Preferably, the NK cells are in vitro expanded autologous NK cells or in vitro expanded allogeneic NK cells.

Various routes of administration may be applied as appropriate. For example, the oncolytic virus is formulated to be administered via intratumoral injection or administered intravenously, and the NK cells are formulated to be administered intravenously.

In specific embodiments of the therapeutic agent, the oncolytic virus is an oncolytic adenovirus. In some examples, E1 region and/or E3 region of the oncolytic adenovirus are/is genetically modified. In some examples, the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

In specific embodiments of the therapeutic agent, the active ingredients of the first pharmaceutical composition comprise an oncolytic adenovirus at a dose ranging from $5\times10^7$ to $5\times10^{12}$ VP/day, and the active ingredients of the second pharmaceutical composition comprise the NK cells at a dose ranging from $1\times10^7$ to $1\times10^{10}$ cells/day. In other specific embodiments, the active ingredient of the first pharmaceutical composition consists of an oncolytic adenovirus at a dose ranging from $5\times10^7$ to $5\times10^{12}$ VP/day, and the active ingredients of the second pharmaceutical composition consist of the NK cells at a dose ranging from $1\times10^7$ to $1\times10^{10}$ cells/day. In other specific embodiments, the therapeutic agent consists of the first pharmaceutical composition and the second pharmaceutical composition.

In some embodiments, the therapeutic agent may be used for preparing drugs for treatment of tumors and/or cancers. The tumors and/or cancers include, but are not limited to, lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia.

The present disclosure also provides a kit of combinational drugs with synergistic effects for treatment of tumors and/or cancers. In certain embodiments, the kit includes independent containers containing an oncolytic virus and NK cells, respectively, and instructions specifying timing and routes of administration; wherein the oncolytic virus can selectively replicate in tumor cells.

In some embodiments of the kit, the independent container containing the oncolytic virus (first container) comprises a therapeutically effective dose of the oncolytic virus, and the independent container containing the NK cells (second container) comprises a dose of the NK cells in the range of $1\times10^7$ to $1\times10^{10}$ cells/day.

In some embodiments, the oncolytic virus is selected from genetically mutated viruses with oncolytic abilities and wild-type viruses with oncolytic abilities. Preferably, the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

The NK cells in the kit may be selected from autologous NK cells and allogeneic NK cells. Preferably, the NK cells are in vitro expanded autologous NK cells or in vitro expanded allogeneic NK cells.

The tumors and/or cancers may include lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukaemia.

In some embodiments, the oncolytic virus is formulated to be administered via intratumoral injection or administered intravenously, and the NK cells are formulated to be administered intravenously.

In specific embodiments, the oncolytic virus in the kit is an oncolytic adenovirus. In some examples, E1 region and/or E3 region of the oncolytic adenovirus are/is genetically modified. In some examples, the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

In specific embodiments, the first container contains an oncolytic adenovirus at a dose ranging from $5\times10^7$ to $5\times10^{12}$ VP/day, and the second container contains the NK cells at a dose ranging from $1\times10^7$ to $1\times10^{10}$ cells/day.

The present disclosure further provides a method for treating a tumor and/or cancer, comprising the following steps in a sequential manner:

1) administering an oncolytic virus to a tumor and/or cancer patient, wherein the oncolytic virus can selectively replicate in tumor cells; and 2) 18 to 72 hours after the administration of the oncolytic virus, administering NK cells to the tumor and/or cancer patient.

In some embodiments, the oncolytic virus is selected from genetically mutated viruses with oncolytic abilities and wild-type viruses with oncolytic abilities. Preferably, the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

In some embodiments, the NK cells are selected from autologous NK cells and allogeneic NK cells. Preferably, the NK cells are in vitro expanded autologous NK cells or in vitro expanded allogeneic NK cells.

In some embodiments, the tumor and/or cancer includes lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia.

In certain embodiments, the oncolytic virus is given at a therapeutically effective dose once daily, consecutively for 1 to 6 days; and the NK cells are given at a dose level ranging from $1\times10^7$ to $1\times10^{10}$ cells/day, once daily, consecutively for 1 to 6 days. Alternatively, the oncolytic virus is given at a therapeutically effective dose every other day, consecutively for 2 to 6 days; and the NK cells are given at a dose level ranging from $1\times10^7$ to $1\times10^{10}$ cells/day, every other day, consecutively for 2 to 6 days.

Various routes of administration may be applied as appropriate. In some embodiments, the oncolytic virus is administered via intratumoral injection or administered intravenously, and the NK cells are administered intravenously.

In specific embodiments of the method, the oncolytic virus is an oncolytic adenovirus. In some examples, E1 region and/or E3 region of the oncolytic adenovirus are/is genetically modified. In some examples, the oncolytic adenovirus is selected from Onyx-015, H101, Ad5-yCD/ mutTKSR39rep-hIL12, CG0070, DNX-2401, OBP-301, ONCOS-102, ColoAd1, VCN-01, and/or ProstAtak™.

In specific embodiments of the method, the oncolytic virus is an oncolytic adenovirus, and the dosage thereof ranges from $5 \times 10^7$ to $5 \times 10^{12}$ VP/day.

Other embodiments are described hereinafter.

The present disclosure has the following advantages and positive effects compared to the prior art:

For the first time, it is provided according to the present disclosure with the idea of combining an oncolytic virus and NK cells for the treatment of tumors and/or cancers, and the pharmaceutical compositions and methods thereof based on this idea allow the oncolytic virus to fully play its role of selective replication in tumor cells and lysis of these tumor cells, and further induction of immune response; meanwhile, it allows NK cells to fully play their role in killing the tumor cells; also, the advantage that the oncolytic virus can selectively replicate in the tumor cells is artfully utilized, so that the oncolytic virus-infected tumor cells become specific targets for NK cells, which further improves the tumor killing functions of NK cells. It was discovered according to the present disclosure that the simple combination of the oncolytic virus and NK cells can produce a synergistic effect. In addition, since both the oncolytic virus and NK cells can recognize tumor cells and basically would do no harm to normal cells, the combination of these two can have significant advantage in terms of safety and efficacy.

Furthermore, theory exploration and experimental research were carried out according to the present disclosure, and the dose levels for each of the oncolytic virus and NK cells, administration sequence thereof and intervals between the administrations were provided to achieve the best synergistic effect for the combined therapy, while avoiding antagonistic effects, so as to provide an effective treatment for tumors and/or cancers.

Definitions

As used herein, the terms "tumor", "cancer", "tumor cell" and "cancer cell" cover the meanings generally recognized in the art.

As used herein, the term "oncolytic virus" refers to a virus that can replicate selectively in and lyse tumor cells. Oncolytic viruses can be genetically modified viruses or wild-type viruses.

As used herein, the term "therapeutically effective dose" refers to an amount of a functional agent or of a pharmaceutical composition useful for exhibiting a detectable therapeutic or inhibitory effect or invoking an antitumor response. The effect can be detected by any assay method known in the art. For example, some of the therapeutically effective doses are listed in Table 1, under the column heading "Dose range or best dose level in clinical practice."

As used herein, the term "administer" or "administration" refers to providing a compound, a composite or a composition (including viruses and cells) to a subject.

As used herein, the term "patient" refers to a human or non-human organism. Thus, the methods and compositions described herein are applicable to both human and veterinary diseases. In certain embodiments, the patient has a tumor. In some cases, the patient may suffer from one or more types of cancer simultaneously.

As used herein, the term "synergistic effect" refers to an effect arising between two or more agents that produce an effect greater than the sum of their individual effects.

As used herein, the term "pfu", or "plaque forming unit" refers to the number of viruses forming a plaque.

As used herein, the term "VP" refers to number of viral particles.

As used herein, the term "VP/kg" refers to number of viral particles per kilogram of patient's body weight.

As used herein, the term "TCID50" stands for median tissue culture infective dose and refers to the viral dose that leads to infection and causes a cytopathic effect in 50% of the tissue culture.

As used herein, the term "MOI", or "multiplicity of infection" refers to the ratio between the number of viruses and the number of cells, I.e., the number of virus particles used to initiate viral infection per cell. MOI=pfu/cell, that is, the number of cells×MOI=Total PFU.

DETAILED DESCRIPTION

Figure 1:
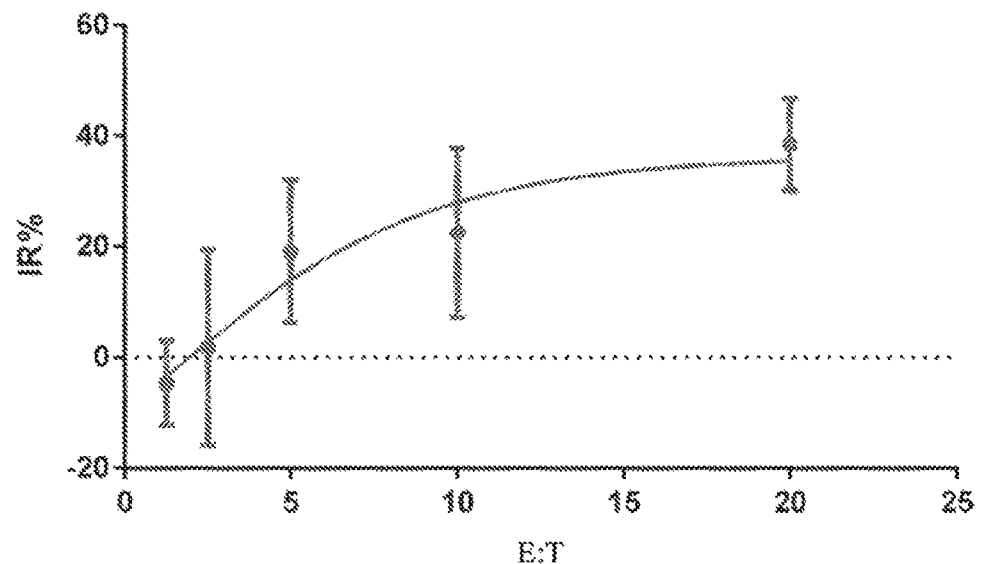
FIG. 1 shows the result of a dose-response experiment of NK cells against A549 cells in Experimental example A1 according to the present disclosure.

The present disclosure is further explained with the following detailed description of preferred embodiments with references to the accompanying drawings, which is not to be taken in a limiting sense, and it will be apparent to those skilled in the art that various modifications or improvements can be made accordingly without departing from the spirit of the present disclosure and these are therefore within the scope of the present disclosure.

Human body is a complex organism comprising ten systems which include respiratory system, circulatory system, digestive system, and etc. These systems coordinate with each other, which allow for normal function of all kinds of complicated life activities. A systemic thinking is such an approach that it is based on an integrated concept and takes into account comprehensively the correlations and interactions between drug actions, diseases, systems and human body.

Currently, many non-cytotoxic anti-tumor drugs do not improve long-term survivals in tumor patients when combined with chemotherapy. This may be due to the lack of systemic thinking in these combination therapies. For example, when a tumor occurs, human body develops anti-tumor responses via multiple, closely correlated immune effects or mechanisms, including cell-mediated immunity and humoral immunity and involving various immune effector molecules and effector cells. It has been generally believed that cell-mediated immunity plays a major role in an anti-tumor process, and that humoral immunity plays more secondary role under some conditions. However, traditional chemotherapies primarily interfere with certain stages of cell life cycle such as synthesis of RNA or DNA, and mitosis, and so, mainly target fast-growing cells. Consequently, while these chemotherapies can kill tumor cells, they also can cause damage to the immune system; when the immune system is weakened, the growth of tumor cells can become unstoppable. Therefore, when targeted non-cytotoxic anti-tumor drugs are combined with chemotherapy or radiotherapy, the sequence and dosage of chemotherapy or radiotherapy should be appropriately scheduled and determined in order to protect the immune system, which is the key to improving efficacy.

On the basis of the above-mentioned systemic thinking, it is possible to maximize efficacy while minimizing damaging to the immune system by employing other approaches for improving the immune function and systematically combining various therapies according to the present disclosure. Accordingly, the disclosure provides a novel combination therapy involving an oncolytic virus and NK cells for the treatment of tumors and/or cancers. Particularly, a synergistic effect can be achieved by only combining oncolytic virus and NK cells according to the present disclosure.

Therefore, the present disclosure provides a therapeutic agent comprising (a) a first pharmaceutical composition comprising an oncolytic virus in a first pharmaceutically acceptable carrier; and (b) a second pharmaceutical composition comprising NK cells in a second pharmaceutically acceptable carrier, wherein the oncolytic virus can selectively replicate in tumor cells.

In some cases, the therapeutic agent can also be interpreted as a combination of drugs.

In some embodiments, the active ingredient of the first pharmaceutical composition is the oncolytic virus, and the active ingredient of the second pharmaceutical composition is the NK cells. In some embodiments, the first pharmaceutical composition comprises the oncolytic virus at a therapeutically effective dose, and the second pharmaceutical composition comprises the NK cells at a dose ranging from $1\times10^7$ to $1\times10^{10}$ cells/day (preferably from $1\times10^8$ to $5\times10^9$ cells/day, more preferably from $1\times10^9$ to $4\times10^9$ cells/day, and still more preferably from $1\times10^9$ to $3\times10^9$ cells/day).

The present disclosure also provides a pharmaceutical composition, wherein active ingredients of the pharmaceutical composition include an oncolytic virus and NK cells, and wherein the oncolytic virus can selectively replicate in tumor cells. Preferably, the active ingredients of the pharmaceutical composition consist of the oncolytic virus and NK cells.

Preferably, the oncolytic virus and the NK cells are provided separately in the pharmaceutical composition without being mixed together.

The mechanisms through which oncolytic viruses kill tumor cells are generally similar. In various embodiments, the oncolytic viruses are administered via intratumoral injection or administered intravenously, and when the oncolytic viruses come into contact with tumor cells, they will infect and enter the tumor cells. Since the oncolytic virus mainly replicates and reproduces in tumor cells with little to no replication in normal cells, large amounts of progeny oncolytic viruses can be produced in the infected tumor cells, leading to lysis and death of the tumor cells. When the tumor cells lyse, large numbers of tumor-associated antigens and the progeny oncolytic viruses may be released, and the antigens can then further activate the immune system in vivo, stimulating NK cells and T cells in vivo to continue to attack the remaining tumor cells. Meanwhile, the progeny oncolytic viruses can infect the tumor cells which have not been infected yet.

NK cells are immune cells which can kill a broad spectrum of tumor cells, and NK cells can distinguish tumor cells from normal cells. When NK cells come into contact with tumor cells, they can recognize tumor cells as abnormal cells, and will kill the tumor cells through multiple assisting processes such as receptor recognition, target recognition by antibodies (ADCC), as well as releases of granzymes, perforins and interferons capable of killing the tumor cells indirectly. An in vitro study has indicated that a healthy NK cell is able to kill up to 27 tumor cells during its life cycle.

NK cells also have anti-virus functions. If normal cells are infected by viruses, the viruses will replicate massively and the infected cells will become aged, showing changes in the composition of protein clusters on the cellular membrane thereof. During this process, NK cells are able to recognize the infected cells sensitively and effectively, and kill these cells with similar approaches they use to kill tumor cells as described above, so as to inhibit replication and proliferation of viruses in the normal cells. Afterwards, with activation of antigens and participation of immune factors like interferons, other types of immune cells will continue to fight against viruses.

In the present disclosure, individual features of the oncolytic virus and NK cells have been taken into account, so they can be combined skillfully. When combined together, the anti-virus mechanism of NK cells is also applicable to tumor cells infected by the oncolytic virus, and this is complementary to the anti-tumor mechanism of NK cells. In addition, the combination therapy allows the tumor cells infected by the oncolytic viruses to become specific targets for NK cells, which can improve their tumor killing effect. The oncolytic viruses not only replicate selectively in cancer cells and kill them from inside, but may also cause the protein receptor clusters on the cellular membrane to change and thus facilitate the recognition of cancer cells by NK cells, so that NK cells can attack the cancer cells from outside. Therefore, the oncolytic virus and NK cells synergistically kill cancer cells, achieving improved efficacy.

Wild-type viruses and NK cells can inhibit each other. On one hand, the viruses inactivate NK cells through the activation of KIR receptors on the surface of NK cells, evading the anti-virus activity of NK cells; on the other hand, NK cells not only can recognize and kill the cells infected by the viruses so as to inhibit the proliferation of the viruses, they also can directly inhibit the viruses via release of interferons. However, since most oncolytic viruses are genetically modified, their tumor specificity is improved, and also their inhibition of immune cells such as NK cells is weakened.

The oncolytic virus in the present disclosure includes genetically mutated viruses with oncolytic abilities and wild-type viruses with oncolytic abilities. Viruses that can be genetically mutated to acquire oncolytic abilities include, but are not limited to, adenovirus, poxvirus (also known as vaccinia virus), herpes simplex virus (HSV), measles virus, Semliki Forest virus, vesicular stomatitis virus, poliovirus, and retrovirus. The wild-type viruses with oncolytic abilities include, but are not limited to, reovirus, vesicular stomatitis virus, poliovirus, Seneca Valley virus, Echo enterovirus, Coxsackie virus, Newcastle disease virus, and Maraba virus.

Exogenous genes may be integrated into the genome of the oncolytic virus. Examples of the exogenous genes include exogenous immunoregulatory genes, exogenous screening genes, exogenous reporter genes, and the like. The exogenous genes may not be integrated into the genome of the oncolytic virus, as well.

The adenovirus includes, but is not limited to, human adenovirus type 5 or human chimeric adenovirus; and specifically includes, such as for example, Onyx-015 (obtainable from Onyx Pharmaceuticals), H101 (obtainable from Shanghai Sunway Biotech Company), Ad5-yCD/mutTKSR39rep-hIL12 (obtainable from Henry Ford Health System), CG0070 (obtainable from Cold Genesys), DNX-2401 (obtainable from DNAtrix), OBP-301 (obtainable from Oncolys BioPharma), ONCOS-102 (obtainable from Targovax Oy/Oncos Therapeutics), ColoAd1 (obtainable from PsiOxus Therapeutics), VCN-01 (obtainable from VCN Biosciences), ProstAtak™ (obtainable from Advantagene), and etc.

Preferably, the adenovirus is H101.

The vaccinia virus may be Wyeth strain, WR strain, Listera strain, Copenhagen strain, or the like.

The vaccinia virus may be functionally deficient in the TK gene, functionally deficient in the VGF gene, or functionally deficient in the TK gene and the VGF gene. The vaccinia virus may also be functionally deficient in other genes including, but not limited to, HA, F14.5L, and F4L.

Preferably, the vaccinia virus is functionally deficient in the TK gene and the VGF gene.

The vaccinia virus includes, but is not limited to, Pexa-vac (obtainable from Jennerex Biotherapeutics), JX-963 (obtainable from Jennerex Biotherapeutics), JX-929 (obtainable from Jennerex Biotherapeutics), VSC20 (for the preparation method thereof, see "McCart, J A, et al. Systemic cancer therapy with a tumor-selective vaccinia virus mutant lacking thymidine kinase and vaccinia growth factor genes. Cancer Res (2001) 61: 8751-8757"), GL-ONC1 (obtainable from Genelux), TG6002 (obtainable from Transgene) and etc.

The herpes simplex virus includes, but is not limited to, HSV-1, HSV-2; and specifically includes, such as for example, Imlygic® (obtainable from Amgen), G207 (obtainable from Medigene), HF10 (obtainable from Takara Bio), Seprehvir (obtainable from Virttu Biologics), OrlenX010 (obtainable from Beijing OrienGene Biotechnology Ltd.), NV1020 (obtainable from Catherax), and etc.

The specific examples of the above mentioned oncolytic viruses are listed in Table 1 below:

TABLE 1

List of oncolytic viruses described in the present disclosure

| Name or Trade name of oncolytic virus | Type of virus/Main features | Source | Dose range or best dose level in clinical practice | Route of administration |
|---|---|---|---|---|
| Onyx-015 | Adenovirus (type 2/5 chimera); E1B-55KD deletion; partial E3 deletion | Onyx Pharmaceuticals | $1 \times 10^7$ to $1 \times 10^{10}$ pfu or $1 \times 10^{10}$ to $2 \times 10^{12}$ VP | Intratumoral or intravenous |
| Oncorine (H101) | Adenovirus type 5 (E1B-55KD deletion; E3 region modification) | Shanghai Sunway Biotech Co., LTD. | $5 \times 10^7$ to $1.5 \times 10^{12}$ VP | Intratumoral |
| Ad5-yCD/mutTKSR 39rep-hIL12 | Adenovirus type 5 (insertion of IL12, yCD, and HSV-1 TKSR39 genes) | Henry Ford Health System | $1 \times 10^{10}$ to $1 \times 10^{12}$ VP | Intraprostatic |
| CG0070 | Adenovirus type 5 (partial E3 deletion; insertion of GM-CSF gene; insertion of E2F promoter into E1a) | Cold Genesys | $1 \times 10^{12}$ VP | Intravesical |
| DNX-2401 (Delta-24-RGD) | Adenovirus (deletion of 24 nucleotides from E1A; insertion of RGD) | DNAtrix | $5 \times 10^8$ to $5 \times 10^{10}$ VP | Intratumoral or intraperitoneal |
| OBP-301 | Adenovirus (insertion of hTERT promoter) | Oncolys BioPharma | $1 \times 10^{10}$ to $1 \times 10^{12}$ VP | Intratumoral |
| ONCOS-102 | Adenovirus (type 3/5 chimera; deletion of 24 nucleotides from E1; partial deletion of E3; insertion of GM-CSF gene) | Targovax Oy/Oncos Therapeutics | $3 \times 10^{10}$ to $3 \times 10^{11}$ VP | Intratumoral or intravenous |
| ColoAd1 (Enadenotucirev) | Adenovirus (Ad11/Ad3 chimeric group B) | PsiOxus Therapeutics | $6 \times 10^{10}$ to $1 \times 10^{12}$ VP | Intratumoral or intravenous or intraperitoneal |
| VCN-01 | Adenovirus type 5 (deletion of 24 nucleotides from E1; insertion of PH20 gene) | VCN Biosciences | $1 \times 10^9$ to $2 \times 10^{11}$ VP | Intratumoral or intravenous |
| ProstAtak ™ | Adenovirus (insertion of TK gene) | Advantagene | | Intraprostatic |
| Imlygic ® (T-Vec) | HSV-1 (ΔICP34.5/ΔICP47; insertion of GM-CSF) | Amgen | $4 \times 10^6$ to $1 \times 10^9$ pfu | Intratumoral |
| G207 | HSV-1 (ΔICP34.5/ΔICP6; insertion of LacZ) | Medigene | $1 \times 10^9$ to $1 \times 10^{10}$ pfu | Intratumoral |
| HF10 | HSV-1 (ΔUL56/ΔUL52) | Takara Bio | $1 \times 10^5$ to $1 \times 10^7$ TCID50 or $1 \times 10^4$ to $1 \times 10^6$ pfu | Intratumoral |

TABLE 1-continued

List of oncolytic viruses described in the present disclosure

| Name or Trade name of oncolytic virus | Type of virus/Main features | Source | Dose range or best dose level in clinical practice | Route of administration |
|---|---|---|---|---|
| Seprehvir (HSV1716) | HSV-1 (ΔICP34.5) | Virttu Biologics | $1 \times 10^5$ to $1 \times 10^7$ i.u. or $1 \times 10^3$ to $5 \times 10^5$ pfu | Intratumoral or intravenous or intrathoracic |
| OrienX010 | HSV-1 (ΔICP6/ΔICP34.5/ΔICP47; insertion of GM-CSF) | Beijing OrienGene Biotechnology Ltd. | ≤$8 \times 10^8$ pfu | Intratumoral |
| NV1020 | HSV (ΔIR/Δγ34.5; envelope glycoprotein gene expressing of HSV2) | Catherax | $3 \times 10^6$ to $1 \times 10^8$ pfu | Intrahepatic |
| Pexa-vac (JX-594) | Vaccinia virus (ΔTK; expression of GM-CSF) | Jennerex Biotherapeutics | $1 \times 10^6$ to $3 \times 10^7$ pfu/kg | Intratumoral or intravenous |
| JX-963 | Vaccinia virus (ΔTK/ΔVGF; expression of GM-CSF) | Jennerex Biotherapeutics | | |
| JX-929 (vvDD-CDSR) | Vaccinia virus (ΔTK/ΔVGF; expression of LacZ, CD/Somatostatin R) | Jennerex Biotherapeutics | $3 \times 10^7$ to $3 \times 10^9$ pfu | Intratumoral or intravenous |
| VSC20 | Vaccinia virus (ΔVGF; insertion of LacZ) | McCart, JA, et al. Systemic cancer therapy with a tumor-selective vaccinia virus mutant lacking thymidine kinase and vaccinia growth factor genes. Cancer Res (2001) 61: 8751-8757. | | |
| GL-ONC1 | Vaccinia virus (ΔTK/ΔHA/ΔF14.5L; insertion of ruc-gfp, LacZ, gusA genes) | Genelux | $1 \times 10^5$ to $5 \times 10^9$ pfu | Intravenous or intraperitoneal or intrathoracic |
| TG6002 | Vaccinia virus (ΔTK/ΔRR; insertion of fuc1 gene) | Transgene | | |
| VSV-hIFNβ | vesicular stomatitis virus (insertion of IFN-β gene) | Obuchi M, et al. Development of recombinant vesicular stomatitis viruses that exploit defects in host defense to augment specific oncolytic activity. J Virol. 2003 Aug; 77(16): 8843-56. | | Intratumoral |
| Toca 511 | Retrovirus (insertion of CD gene) | Tocagen | | Intratumoral or intravenous |
| MV-NIS | Measles virus (insertion of NIS gene) | Mayo Clinic | $1 \times 10^{11}$ $TCID_{50}$ | Intratumoral or intraperitoneal or intrathoracic or intravenous |
| MV-CEA | Measles virus (insertion of CEA gene) | Mayo Clinic | | Intratumoral or intraperitoneal |

TABLE 1-continued

List of oncolytic viruses described in the present disclosure

| Name or Trade name of oncolytic virus | Type of virus/Main features | Source | Dose range or best dose level in clinical practice | Route of administration |
|---|---|---|---|---|
| PVSRIPO | Poliovirus (modification of IRES) | Brown, Michael C., et al. Oncolytic polio virotherapy of cancer. Cancer. 2014. 120 (21): 3277-3286 | | |
| NTX-010 (SVV-001) | Seneca Valley virus (wild-type) | Neotropix | $1 \times 10^7$ to $1 \times 10^{11}$ VP/kg | Intratumoral or systematical |
| Cavatak ™ (CVA21) | Coxsackie virus (wild-type) | Viralytics | $1 \times 10^8$ to $1 \times 10^9$ TCID50 | Intratumoral or intravenous |
| Reolysin ® | reovirus (wild-type) | Oncolytics Biotech | $1 \times 10^8$ to $3 \times 10^{10}$ TCID50 or $1 \times 10^{10}$ pfu | Intratumoral or intravenous or intraperitoneal |
| PV701 | Newcastle disease virus (wild-type) | Wellstat Biologics | | Intravenous |
| MTH-68/H | Newcastle disease virus (wild-type) | United Cancer Research Institute | | |

The NK cells in the present disclosure include autologous NK cells and allogeneic NK cells. The NK cells may be in vitro expanded NK cells. The technology for massive in vitro expansion of NK cells is known in the art and highly developed (see, for example, "Somanchi S S, Lee D A. Ex Vivo Expansion of Human NK Cells Using K562 Engineered to Express Membrane Bound IL21. Methods Mol Biol. 2016; 1441:175-93" or "Phan M T, Lee S H, Kim S K, Cho D. Expansion of NK Cells Using Genetically Engineered K562 Feeder Cells. Methods Mol Biol. 2016; 1441: 167-74"). It has been demonstrated from clinical data that when autologous NK cells, semi-allogeneic NK cells (belonging to allogeneic NK cells) or umbilical cord blood-derived NK cells were infused into human body, no toxicities or long-term dependency had been observed, and the treatment was safe and effective.

The purity of the NK cells useful for the treatment may be 85% or more for the autologous NK cells and 90% or more for the allogeneic NK cells, and the impurity cells therein may be NK-T and/or γδ T cells. Preferably, the NK cell activity (survival rate) is 90% or more, and the NK cell killing activity is 80% or more.

Based on the combination strategies in the present disclosure, further explorations and improvements are made regarding respective dose levels of the oncolytic virus and NK cells, administration sequence thereof and intervals between the administrations, which are essential for determining the anti-tumor efficacy of the oncolytic virus, the anti-tumor efficacy of NK cells and the best synergistic killing effect of the combination of the two against tumor cells.

Therefore, preferably, the pharmaceutical composition or therapeutic agent includes the oncolytic virus at a therapeutically effective dose, and includes the NK cells at a dose ranging from $1 \times 10^7$ to $1 \times 10^{10}$ cells/day (preferably from $1 \times 10^8$ to $5 \times 10^9$ cells/day, more preferably from $1 \times 10^9$ to $4 \times 10^9$ cells/day, and still more preferably from $1 \times 10^9$ to $3 \times 10^9$ cells/day). For different oncolytic viruses, different preferable dose ranges suitable for clinical application can be chosen, such as those listed in Table 1.

The oncolytic viruses can be administered through different routes commonly used in the art, respectively; for example, they can be administered via intratumoral injection or administered intravenously.

The NK cells can be administered through different routes commonly used in the art; for example, they can be administered intravenously.

In specific embodiments, the oncolytic virus in the pharmaceutical composition or therapeutic agent according to the present disclosure is an adenovirus with oncolytic abilities (hereinafter also referred to as "oncolytic adenovirus"). In some examples, the E1 region and/or E3 region of the oncolytic adenovirus are/is genetically modified. In some examples, the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

In certain embodiments, the active ingredients of the pharmaceutical composition or therapeutic agent according to the present disclosure include the oncolytic adenovirus at a dose ranging from $5 \times 10^7$ to $5 \times 10^{12}$ VP/day (e.g., $5 \times 10^7$ to $1.5 \times 10^{12}$ VP/day, $5 \times 10^8$ to $1 \times 10^{12}$ VP/day, $1 \times 10^9$ to $5 \times 10^{11}$ VP/day, $3 \times 10^{10}$ to $3 \times 10^{11}$ VP/day, etc.) and the NK cells at a dose ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, $1 \times 10^9$ to $3 \times 10^9$ cells/day, etc.). Preferably, the active ingredients of the pharmaceutical composition or therapeutic agent consist of the oncolytic adenovirus at a dose ranging from $5 \times 10^7$ to $5 \times 10^{12}$ VP/day (e.g., $5 \times 10^7$ to $1.5 \times 10^{12}$ VP/day, $5 \times 10^8$ to $1 \times 10^{12}$ VP/day, $1 \times 10^9$ to $5 \times 10^{11}$ VP/day, $3 \times 10^{10}$ to $3 \times 10^{11}$ VP/day, etc.) and the NK cells at a dose ranging from $1 \times 10^7$ to $1 \times 10^{10}$ cells/day (e.g., $1 \times 10^9$ to $5 \times 10^9$ cells/day, $1 \times 10^9$ to $4 \times 10^9$ cells/day, $1 \times 10^9$ to $3 \times 10^9$ cells/day, etc.).

In an embodiment, the active ingredients of the pharmaceutical composition or therapeutic agent according to the present disclosure include the oncolytic virus H101 at a dose ranging from $5 \times 10^7$ to $1.5 \times 10^{12}$ VP/day (e.g., $5 \times 10^{11}$ to $1.5 \times 10^{12}$ VP/day, etc.) and the NK cells at a dose ranging from $1 \times 10^7$ to $1 \times 10^{10}$ cells/day. Preferably, the active ingredients of the pharmaceutical composition or therapeutic agent consist of the oncolytic virus H101 at a dose ranging from $5 \times 10^7$ to $1.5 \times 10^{12}$ VP/day (e.g., $5 \times 10^{11}$ to $1.5 \times 10^{12}$ VP/day, etc.) and the NK cells at a dose ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, $1 \times 10^9$ to $3 \times 10^9$ cells/day, etc.).

In specific embodiments, the oncolytic virus in the pharmaceutical composition or therapeutic agent according to the present disclosure is a vaccinia virus with oncolytic abilities (hereinafter also referred to as "oncolytic vaccinia virus"). In some examples, the oncolytic vaccinia virus is selected from genetically mutated viruses with oncolytic abilities and wild-type viruses with oncolytic abilities. In some examples, the oncolytic vaccinia virus is functionally deficient in the TK gene and/or in the VGF gene. In some examples, the oncolytic vaccinia virus is selected from Pexa-vac, JX-963, JX-929, VSC20, GL-ONC1, and/or TG6002.

In certain embodiments, the active ingredients of the pharmaceutical composition or therapeutic agent according to the present disclosure include the oncolytic vaccinia virus at a dose ranging from $1 \times 10^5$ to $5 \times 10^9$ pfu/day (e.g., $1 \times 10^5$ to $3 \times 10^9$ pfu/day, $1 \times 10^5$ to $1 \times 10^8$ pfu/day, etc.) and the NK cells at a dose ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, $1 \times 10^9$ to $3 \times 10^9$ cells/day, etc.). Preferably, the active ingredients of the pharmaceutical composition or therapeutic agent consist of the oncolytic vaccinia virus at a dose ranging from $1 \times 10^5$ to $5 \times 10^9$ pfu/day (e.g., $1 \times 10^5$ to $3 \times 10^9$ pfu/day, $1 \times 10^5$ to $1 \times 10^8$ pfu/day, etc.) and the NK cells at a dose ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, $1 \times 10^9$ to $3 \times 10^9$ cells/day, etc.).

A person skilled in the art can understand that the pharmaceutical composition or therapeutic agent according to the present disclosure can also include suitable pharmaceutical excipients.

The pharmaceutical composition or therapeutic agent according to the present disclosure may also include other active ingredients known in the field, such as interleukin-2 (IL-2), granulocyte-macrophage colony stimulating factor (GM-CSF), interferon-γ (IFN-γ), tumor necrosis factor-α (TNF-α), etc.

Preferably, the pharmaceutical composition or therapeutic agent according to the present disclosure does not include bortezomib.

In some embodiments, the pharmaceutical composition or therapeutic agent of the present disclosure comprises one or more pharmaceutically acceptable carriers. Pharmaceutical formulations can be prepared by procedures known in the art. For example, the active ingredients including compounds and the like can be formulated with common excipients, diluents (such as phosphate buffer or saline), tissue-culture medium, and carriers (such as autologous plasma or human serum albumin) and administered as a suspension. Other carriers can include liposomes, micelles, nanocapsules, polymeric nanoparticles, solid lipid particles (see, e.g., E. Koren and V. Torchilin, Life, 63:586-595, 2011). Details on techniques for formulation of the pharmaceutical composition or therapeutic agent disclosed herein are well described in the scientific and patent literature, see, e.g., the latest edition of Remington's Pharmaceutical Sciences, Maack Publishing Co., Easton Pa. ("Remington's").

In some embodiments, the disclosure provides a therapeutic agent comprising: (a) a first pharmaceutical composition comprising an oncolytic virus in a first pharmaceutically acceptable carrier; and (b) a second pharmaceutical composition comprising NK cells in a second pharmaceutically acceptable carrier, wherein the oncolytic virus can selectively replicate in tumor cells. In some embodiments, the first and the second pharmaceutically acceptable carriers are the same. In other embodiments, the first and second pharmaceutically acceptable carriers are different.

The pharmaceutical composition or therapeutic agent according to the present disclosure can be used to treat various tumors and/or cancers, including, but not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia, etc.

The application method of the pharmaceutical composition or therapeutic agent of the present disclosure is as follows: first, administering the oncolytic virus (e.g., oncolytic adenovirus, oncolytic vaccinia virus or oncolytic herpes simplex virus) to a patient having tumor and/or cancer; then, 18-72 hours (e.g., 20-70 hours, 22-48 hours, 24-48 hours, 30-48 hours, etc.) after the administration of the oncolytic virus, administering the NK cells to the tumor and/or cancer patient. The phrase "18-72 hours (e.g., 20-70 hours, 22-48 hours, 24-48 hours, 30-48 hours, etc.) after the administration of the oncolytic virus, administering the NK cells to the tumor and/or cancer patient" means that the time interval between the first administration of the NK cells and the first administration of the oncolytic virus is in the range of 18-72 hours (e.g., 20-70 hours, 22-48 hours, 24-48 hours, 30-48 hours, etc.), or the time interval between the first administration of the NK cells and the most recent administration of the oncolytic virus is in the range of 18-72 hours (e.g., 20-70 hours, 22-48 hours, 24-48 hours, 30-48 hours, etc.). Preferably, the time interval between the first administration of the NK cells and the most recent administration of the oncolytic virus is in the range of 18-72 hours (e.g., 20-70 hours, 22-48 hours, 24-48 hours, 30-48 hours, etc.). More preferably, the time interval between the first administration of the NK cells and the most recent administration of the oncolytic virus is in the range of 24-48 hours.

In a preferred embodiment of the present disclosure, the oncolytic virus (e.g., oncolytic adenovirus, oncolytic vaccinia virus or oncolytic herpes simplex virus) is given at a therapeutically effective dose once daily, consecutively for 1 to 6 days; and the NK cells are given at a dose level ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, or $1 \times 10^9$ to $3 \times 10^9$ cells/day) once daily, consecutively for 1 to 6 days. In another preferred embodiment of the present disclosure, the oncolytic virus (e.g., oncolytic adenovirus, oncolytic vaccinia virus or oncolytic herpes simplex virus) is given at a therapeutically effective dose every other day, consecutively for 2 to 6 days; and the NK cells are given at a dose level ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, or $1 \times 10^9$ to $3 \times 10^9$ cells/day) every other day, consecutively for 2 to 6 days. Any one of the above mentioned embodiments or any other alternative embodiment can be adopted according to the present disclosure, as long as the NK cells are to be given to the tumor and/or cancer patient 18 to 72 hours after administration of the oncolytic virus (e.g., oncolytic adenovirus, oncolytic vaccinia virus or oncolytic herpes simplex virus). The oncolytic virus and NK cells may be administered alternatively (for example, administering the oncolytic virus on day 1, administering the NK cells on day 2, administering the oncolytic virus on day 3, and administering the NK cells on day 4, and so on); or may be administered sequentially (for example, administering the oncolytic virus on day 1, administering the oncolytic virus and NK cells in a sequential order on day 2, administering the oncolytic virus and NK cells in a sequential order on day 3, and administering the oncolytic virus and NK cells in a sequential order on day 4, and so on); or may be administered using other dosage regimens (for example, first, administering the oncolytic virus once daily for consecutive 1 to 6 days, and after an interval of 18 to 72 hours, administering the NK cells once daily for consecutive 1 to 6 days). Preferably, the oncolytic virus is administered first, and the NK cells are administered 18 to 72 hours after completion of administrating all the doses of oncolytic virus. In a preferred embodiment of the present disclosure, first, the tumor and/or cancer patient is given the oncolytic virus, and the oncolytic virus is given once only at a therapeutically effective dose; 18 to 72 hours after administration of the oncolytic virus, the tumor and/or cancer patient is administered the NK cells, and the NK cells are administered once only at a dose level ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, or $1 \times 10^9$ to $3 \times 10^9$ cells/day). For different oncolytic viruses, different preferable dose ranges suitable for clinical application can be chosen, such as those listed in Table 1.

The oncolytic viruses can selectively replicate in tumor or cancer cells and the amount thereof will reach a peak after a certain period of time. The inventors of the present disclosure have discovered that after a period of viral replication, the oncolytic viruses in tumor cells can promote the killing effect of the NK cells against tumor cells. Therefore, the intervals between the administrations of the oncolytic virus and NK cells proposed in the present disclosure can enable that the peak values of their functions overlap.

The present disclosure also provides use of the pharmaceutical compositions or therapeutic agents of the disclosure for the preparation of drugs for treatment of tumors and/or cancers.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia, etc.

The present disclosure also provides a kit of combinational drugs with synergistic effect for treatment of tumors and/or cancers, including a first container containing the oncolytic virus and a second container containing the NK cells according to the present disclosure, wherein the first container is separate from the second container. The kit further comprises instructions specifying timing and routes of administration, wherein the oncolytic virus can selectively replicate in tumor cells. Preferably, the kit consists of independent containers respectively containing the oncolytic virus and the NK cells according to the present disclosure, and an instruction sheet specifying timing and routes of administration.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia, etc.

Preferably, the first container in the kit containing the oncolytic virus includes the oncolytic virus at a therapeutically effective dose, and the second container containing the NK cells includes the NK cells at an amount that is sufficient for providing a dose ranging from $1 \times 10^7$ to $1 \times 10^{10}$ cells/day (e.g., $1 \times 10^8$ to $5 \times 10^9$ cells/day, $1 \times 10^9$ to $4 \times 10^9$ cells/day, $1 \times 10^9$ to $3 \times 10^9$ cells/day, etc.). For different oncolytic viruses, different preferable dose ranges suitable for clinical application may be chosen, such as those listed in Table 1.

The oncolytic viruses can be administered through the respective routes commonly used in the art; for example, they can be administered via intratumoral injection or administered intravenously.

The NK cells can be administered through the routes commonly used in the art; for example, they can be administered intravenously.

In specific embodiments of the kit according to the present disclosure, the oncolytic virus is an adenovirus with oncolytic abilities. In some examples, the E1 region and/or E3 region of the oncolytic adenovirus are/is genetically modified. In some examples, the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

In specific embodiments of the kit according to the present disclosure, the first container contains the oncolytic adenovirus at a dose ranging from $5 \times 10^7$ to $5 \times 10^{12}$ VP/day (e.g., $5 \times 10^7$ to $1.5 \times 10^{12}$ VP/day, $5 \times 10^8$ to $1 \times 10^{12}$ VP/day, $1 \times 10^9$ to $5 \times 10^{11}$ VP/day, $3 \times 10^{10}$ to $3 \times 10^{11}$ VP/day, etc.).

In an embodiment, the first container contains the oncolytic virus H101 at a dose ranging from $5 \times 10^7$ to $1.5 \times 10^{12}$ VP/day (e.g., $5 \times 10^{11}$ to $1.5 \times 10^{12}$ VP/day, etc.).

In specific embodiments of the kit according to the present disclosure, the oncolytic virus is an oncolytic vaccinia virus. In some examples, the oncolytic vaccinia virus is selected from genetically mutated viruses with oncolytic abilities and wild-type viruses with oncolytic abilities. In some examples, the oncolytic vaccinia virus is functionally deficient in the TK gene and/or in the VGF gene. In some examples, the oncolytic vaccinia virus is selected from Pexa-vac, JX-963, JX-929, VSC20, GL-ONC1, and/or TG6002.

In specific embodiments of the kit according to the present disclosure, the first container contains the oncolytic vaccinia virus at a dose ranging from $1 \times 10^5$ to $5 \times 10^9$ pfu/day (e.g., $1 \times 10^5$ to $3 \times 10^9$ pfu/day, $1 \times 10^5$ to $1 \times 10^8$ pfu/day, etc.).

The present disclosure also provides a method for treatment of tumors and/or cancers, comprising, in a sequential manner, the following steps:

1) administering the oncolytic viruses according to the present disclosure to a tumor and/or cancer patient, wherein the oncolytic virus can selectively replicate in tumor cells;

2) 18-72 hours (e.g., 20-70 hours, 22-48 hours, 24-48 hours, 30-48 hours, etc.) after the administration of the oncolytic virus, administering the NK cells according to the present disclosure to the tumor and/or cancer patient.

The phrase "18-72 hours (e.g., 20-70 hours, 22-48 hours, 24-48 hours, 30-48 hours, etc.) after the administration of the oncolytic virus, administering the NK cells according to the present disclosure to the tumor and/or cancer patient" means that the time interval between the first administration of the NK cells and the first administration of the oncolytic virus is in the range of 18-72 hours (e.g., 20-70 hours, 22-48 hours, 24-48 hours, 30-48 hours, etc.), or the time interval between the first administration of the NK cells and the most recent administration of the oncolytic virus is in the range of 18-72 hours (e.g., 20-70 hours, 22-48 hours, 24-48 hours, 30-48 hours, etc.). Preferably, the time interval between the first administration of the NK cells and the most recent administration of the oncolytic virus is in the range of 18-72 hours (e.g., 20-70 hours, 22-48 hours, 24-48 hours, 30-48 hours, etc.). More preferably, the time interval between the first administration of the NK cells and the most recent administration of the oncolytic virus is in the range of 24-48 hours.

The tumors and/or cancers include, but are not limited to, lung cancer (e.g., non-small cell lung cancer), melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia, etc.

In a preferred embodiment of the present disclosure, the oncolytic virus is given at a therapeutically effective dose once daily, consecutively for 1 to 6 days; and the NK cells are given at a dose level ranging from $1\times10^7$ to $1\times10^{10}$ cells/day (e.g., $1\times10^8$ to $5\times10^9$ cells/day, $1\times10^9$ to $4\times10^9$ cells/day, or $1\times10^9$ to $3\times10^9$ cells/day) once daily, consecutively for 1 to 6 days. In another preferred embodiment of the present disclosure, the oncolytic virus is given at a therapeutically effective dose every other day, consecutively for 2 to 6 days; and the NK cells are given at a dose level ranging from $1\times10^7$ to $1\times10^{10}$ cells/day (e.g., $1\times10^8$ to $5\times10^9$ cells/day, $1\times10^9$ to $4\times10^9$ cells/day, or $1\times10^9$ to $3\times10^9$ cells/day) every other day, consecutively for 2 to 6 days. Any one of the above mentioned embodiments or any other alternative embodiment can be adopted according to the present disclosure, as long as the NK cells are to be given to the tumor and/or cancer patient 18 to 72 hours after administration of the oncolytic virus. The oncolytic virus and NK cells may be administered alternatively (for example, administering the oncolytic virus on day 1, administering the NK cells on day 2, administering the oncolytic virus on day 3, and administering the NK cells on day 4, and so on); or may be administered sequentially (for example, administering the oncolytic virus on day 1, administering the oncolytic virus and NK cells in a sequential order on day 2, administering the oncolytic virus and NK cells in a sequential order on day 3, and administering the oncolytic virus and NK cells in a sequential order on day 4, and so on); or may be administered using other dosage regimens (for example, first, administering the oncolytic virus once daily for consecutive 1 to 6 days, and after an interval of 18 to 72 hours, administering the NK cells once daily for consecutive 1 to 6 days). Preferably, the oncolytic virus is administered first, and the NK cells are administered 18 to 72 hours after completion of administrating all the doses of oncolytic virus. In a preferred embodiment of the present disclosure, first, the tumor and/or cancer patient is given the oncolytic virus, and the oncolytic virus is given once only at a therapeutically effective dose; 18 to 72 hours after administration of the oncolytic virus, the tumor and/or cancer patient is given the NK cells, and the NK cells are given once only at a dose level ranging from $1\times10^7$ to $1\times10^{10}$ cells/day (e.g., $1\times10^8$ to $5\times10^9$ cells/day, $1\times10^9$ to $4\times10^9$ cells/day, or $1\times10^9$ to $3\times10^9$ cells/day). For different oncolytic viruses, different preferable dose ranges suitable for clinical application can be chosen, such as those listed in Table 1.

Based on specific situations and needs, the method for the treatment of tumors and/or cancers according to the present disclosure can be applied to a patient for one time or multiple times.

The oncolytic viruses can be administered through the respective routes commonly used in the art; for example, they can be administered via intratumoral injection or administered intravenously.

The NK cells can be administered through the routes commonly used in the art; for example, they can be administered intravenously.

In specific embodiments of the method according to the present disclosure, the oncolytic virus is an adenovirus with oncolytic abilities. In some examples, the E1 region and/or E3 region of the oncolytic adenovirus are/is genetically modified. In some examples, the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

In certain embodiments of the method according to the present disclosure, the oncolytic virus is an oncolytic adenovirus, and the dosage thereof ranges from $5\times10^7$ to $5\times10^{12}$ VP/day (e.g., $5\times10^7$ to $1.5\times10^{12}$ VP/day, $5\times10^8$ to $1\times10^{12}$ VP/day, $1\times10^9$ to $5\times10^{11}$ VP/day, $3\times10^{10}$ to $3\times10^{11}$ VP/day, etc.).

In an embodiment, the oncolytic virus is the oncolytic virus H101, and the dosage thereof ranges from $5\times10^7$ to $1.5\times10^{12}$ VP/day (e.g., $5\times10^{11}$ to $1.5\times10^{12}$ VP/day, etc.).

In specific embodiments of the method according to the present disclosure, the oncolytic virus is an oncolytic vaccinia virus. In some examples, the oncolytic vaccinia virus is selected from genetically mutated viruses with oncolytic abilities and wild-type viruses with oncolytic abilities. In some examples, the oncolytic vaccinia virus is functionally deficient in the TK gene and/or in the VGF gene. In some examples, the oncolytic vaccinia virus is selected from Pexa-vac, JX-963, JX-929, VSC20, GL-ONC1, and/or TG6002.

In certain embodiments of the method according to the present disclosure, the oncolytic virus is an oncolytic vaccinia virus, and the dosage thereof ranges from $1\times10^5$ to $5\times10^9$ pfu/day (e.g., $1\times10^5$ to $3\times10^9$ pfu/day, $1\times10^5$ to $1\times10^8$ pfu/day, etc.).

EXEMPLARY EMBODIMENTS OF THE INVENTION

Provided hereafter is a listing of non-limiting embodiments of the invention.

1. A therapeutic agent, comprising:
(a) a first pharmaceutical composition comprising an oncolytic virus in a first pharmaceutically acceptable carrier; and
(b) a second pharmaceutical composition comprising NK cells in a second pharmaceutically acceptable carrier;
wherein the oncolytic virus can selectively replicate in tumor cells.

2. The therapeutic agent of embodiment 1, wherein the first pharmaceutical composition and the second pharmaceutical composition are present separately in the therapeutic agent without being mixed together.

3. The therapeutic agent of embodiment 1, wherein the active ingredient of the first pharmaceutical composition is the oncolytic virus; and wherein the active ingredient of the second pharmaceutical composition is the NK cells.

4. The therapeutic agent of embodiment 1, wherein the first pharmaceutical composition comprises the oncolytic virus at a therapeutically effective dose, and the second pharmaceutical composition comprises the NK cells at a dose ranging from $1\times10^7$ to $1\times10^{10}$ cells/day.

5. The therapeutic agent of embodiment 1, wherein the oncolytic virus is selected from genetically mutated viruses with oncolytic abilities and wild-type viruses with oncolytic abilities.

6. The therapeutic agent of embodiment 1, wherein the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

7. The therapeutic agent of embodiment 1, wherein the NK cells are selected from autologous NK cells and allogeneic NK cells.

8. The therapeutic agent of embodiment 7, wherein the NK cells are in vitro expanded autologous NK cells or in vitro expanded allogeneic NK cells.

9. The therapeutic agent of embodiment 1, wherein the oncolytic virus is formulated to be administered via intratumoral injection or administered intravenously; and wherein the NK cells are formulated to be administered intravenously.

10. The therapeutic agent of any one of embodiments 1-9, wherein the oncolytic virus is an oncolytic adenovirus.

11. The therapeutic agent of embodiment 10, wherein E1 region and/or E3 region of the oncolytic adenovirus are/is genetically modified.

12. The therapeutic agent of embodiment 10, wherein the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

13. The therapeutic agent of embodiment 1, wherein the active ingredients of the first pharmaceutical composition comprise an oncolytic adenovirus at a dose ranging from $5 \times 10^7$ to $5 \times 10^{12}$ VP/day; and wherein the active ingredients of the second pharmaceutical composition comprise the NK cells at a dose ranging from $1 \times 10^7$ to $1 \times 10^{10}$ cells/day.

14. The therapeutic agent of embodiment 1, consisting of the first pharmaceutical composition and the second pharmaceutical composition.

15. Use of the therapeutic agent of any one of embodiments 1-14 for preparation of drugs for treatment of tumors and/or cancers.

16. The use of embodiment 15, wherein the tumors and/or cancers include lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia.

17. A kit of combinational drugs with synergistic effects for treatment of tumors and/or cancers, comprising a first container containing an oncolytic virus and a second container containing NK cells, wherein the first container is separate from the second container; and instructions specifying timing and routes of administration; wherein the oncolytic virus can selectively replicate in tumor cells.

18. The kit of embodiment 17, wherein the first container contains the oncolytic virus at a therapeutically effective dose, and the second container contains the NK cells at a dose ranging from $1 \times 10^7$ to $\times 10^{10}$ cells/day.

19. The kit of embodiment 17, wherein the oncolytic virus is selected from genetically mutated viruses with oncolytic abilities and wild-type viruses with oncolytic abilities.

20. The kit of embodiment 17, wherein the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

21. The kit of embodiment 17, wherein the NK cells are selected from autologous NK cells and allogeneic NK cells.

22. The kit of embodiment 21, wherein the NK cells are in vitro expanded autologous NK cells or in vitro expanded allogeneic NK cells.

23. The kit of embodiment 17, wherein the tumors and/or cancers include lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukaemia.

24. The kit of embodiment 17, wherein the oncolytic virus is formulated to be administered via intratumoral injection or administered intravenously; and wherein the NK cells are formulated to be administered intravenously.

25. The kit of any one of embodiments 17-24, wherein the oncolytic virus is an oncolytic adenovirus.

26. The kit of embodiment 25, wherein E1 region and/or E3 region of the oncolytic adenovirus are/is genetically modified.

27. The kit of embodiment 25, wherein the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

28. The kit of embodiment 17, wherein the first container contains an oncolytic adenovirus at a dose ranging from $5 \times 10^7$ to $5 \times 10^{12}$ VP/day; and wherein the second container contains the NK cells at a dose ranging from $1 \times 10^7$ to $1 \times 10^{10}$ cells/day.

29. A method for treating a tumor and/or cancer, comprising the following steps in a sequential manner:
1) administering an oncolytic virus to a tumor and/or cancer patient, wherein the oncolytic virus can selectively replicate in tumor cells; and
2) 18 to 72 hours after the administration of the oncolytic virus, administering NK cells to the tumor and/or cancer patient.

30. The method of embodiment 29, wherein the oncolytic virus is selected from genetically mutated viruses with oncolytic abilities and wild-type viruses with oncolytic abilities.

31. The method of embodiment 29, wherein the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

32. The method of embodiment 29, wherein the NK cells are selected from autologous NK cells and allogeneic NK cells.

33. The method of embodiment 32, wherein the NK cells are in vitro expanded autologous NK cells or in vitro expanded allogeneic NK cells.

34. The method of embodiment 29, wherein the tumor and/or cancer includes lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia.

35. The method of embodiment 29, wherein the oncolytic virus is given at a therapeutically effective dose once daily, consecutively for 1 to 6 days.

36. The method of embodiment 29, wherein the NK cells are given at a dose level ranging from $1\times10^7$ to $1\times10^{10}$ cells/day, once daily, consecutively for 1 to 6 days.

37. The method of embodiment 29, wherein the oncolytic virus is given at a therapeutically effective dose every other day, consecutively for 2 to 6 days.

38. The method of embodiment 29, wherein the NK cells are given at a dose level ranging from $1\times10^7$ to $1\times10^{10}$ cells/day, every other day, consecutively for 2 to 6 days.

39. The method of embodiment 29, wherein the oncolytic virus is administered via intratumoral injection or administered intravenously; and wherein the NK cells are administered intravenously.

40. The method of any one of embodiments 29-39, wherein the oncolytic virus is an oncolytic adenovirus.

41. The method of embodiment 40, wherein E1 region and/or E3 region of the oncolytic adenovirus are/is genetically modified.

42. The method of embodiment 40, wherein the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

43. The method of embodiment 29, wherein the oncolytic virus is an oncolytic adenovirus, and the dosage thereof ranges from $5\times10^7$ to $5\times10^{12}$ VP/day.

Hereinafter, the present disclosure will be further explained or described by way of examples, but these examples are not intended to limit the scope of protection of the present disclosure.

EXAMPLES

Unless otherwise specified, all the percentage concentrations (%) of the respective agents indicate percentage by volume (% (v/v)).

The materials used in the following examples are described below.

1. Tumor Cells

A549 (human non-small cell lung cancer cells), HepG2 (human hepatocellular carcinoma cells), HT29 (human colon cancer cells), HCT116 (human colorectal cancer cells), FaDu (human head and neck cancer cells), SK-HEP-1 (human hepatocellular carcinoma cells), PANC-1 (human pancreatic cancer cells) and the like were obtained from China National Infrastructure of Cell Line Resource. The cells were cultured in normal environment: DMEM+10% FBS, DMEM:F12 (1:1)+10% FBS, McCoy's 5A+10% FBS, or MEM+10% FBS. DMEM:F12 (1:1) was purchased from Hyclone, while DMEM, McCoy's 5A and MEM were purchased from GIBCO. Fetal bovine serum (FBS) was purchased from GIBCO Inc. Human umbilical vein endothelial cells (HUVEC) and its culture system were both purchased from ALLCELLS LLC, Germany.

2. NK Cells

The sources of NK cells used in the experiments are as follows:

1) The NK cells used in each example of Group A were human NK cells, Sample No. 0215111703, purchased from Hangzhou Ding Yun Biotech Co., Ltd.

2) The NK cells used in each example of Groups B, C, F, G H, I, and J were human NK cells cultured and cryopreserved by Hangzhou ConVerd Co., Ltd. The human NK cells were prepared by the following process. As commonly used techniques in the art, a blood collection needle was inserted into an ulnar vein to collect peripheral venous blood of a healthy person for extraction of immune cells PBMC. Irradiated K562 feeder cells (purchased from Hangzhou Ding Yun Biotech Co., Ltd.) were used to expand NK cells by autologous plasma culture, and the NK cells had a final purity up to 90%, a viability up to 90%, and in vitro tumor cell killing rate up to 85%.

3) The NK cells used in each example of Groups D and E are human NK cells, Sample No. 0116010805, purchased from Hangzhou Ding Yun Biotech Co., Ltd.

3. Oncolytic Virus (OV)

The oncolytic adenovirus H101 was obtained from Shanghai Sunway Biotech Co., Ltd.

The oncolytic vaccinia virus ddvv-RFP is known, and it belongs to the oncolytic vaccinia virus WR strain (see, for example, "X Song, et al. T-cell Engager-armed Oncolytic Vaccinia Virus Significantly Enhances Antitumor Therapy Molecular Therapy. (2014); 22 1, 102-111"). The oncolytic vaccinia virus ddvv-RFP is functionally deficient in both TK gene and VGF gene, and carries an exogenous red fluorescent protein (RFP) gene. Since the RFP gene only plays a screening/reporting role, the anti-tumor function of the oncolytic vaccinia virus ddvv-RFP is substantially equivalent to the oncolytic vaccinia virus functionally deficient in TK gene and VGF gene. Also, the oncolytic vaccinia virus ddvv-RFP can be obtained by genetic modification of VSC20 vaccinia virus using conventional techniques in the art. VSC20 vaccinia virus is a vaccinia virus lack of VGF gene. For the preparation method of VSC20 vaccinia virus, see "McCart, J A, et al. Systemic cancer therapy with a tumor-selective vaccinia virus mutant lacking thymidine kinase and vaccinia growth factor genes. Cancer Res (2001) 61: 8751-8757". The genetic modification involves the use of an artificial synthetic vaccinia virus early/late promoter pSEL to regulate the exogenous DsRed gene (i.e., the RFP gene), and insertion of the DsRed gene into the TK gene region of the vaccinia virus VSC20 strain using an in vitro intracellular recombination technique, thereby constructing the oncolytic vaccinia virus ddvv-RFP.

4. Culture Plate

A 24-well cell culture plate (500 µl per well; Corning Inc.) was used in each example of Groups A-J (except for Experimental examples C11 and C12). A 12-well cell culture plate (1 ml per well; Corning Inc.) was used in each of Experimental examples C11 and C12.

The cell counting method used in the following examples is described below:

Cell counting using Trypan Blue Staining method: the cells were washed with PBS and digested using trypsin, and then the cells were suspended in PBS. To the suspension added Trypan Blue solution to a final concentration of 0.04% (w/v). Then, cell counting was performed under a microscope, during which dead cells were stained blue and living cells appeared transparent without any color. The living cell counts were used as final data.

In the dose-response experiments and killing experiments of oncolytic viruses against tumor cells in the following examples, when the tumor cells were infected by an oncolytic virus first and then cultured or incubated, the time point at which the oncolytic virus was added was taken as 0 hour.

A: Study on the Killing Effect of Combined Application of Oncolytic Adenovirus and NK Cells Against A549 Cells Experimental Example A1: Dose-Response Experiment of NK Cells Against A549 Cells A549 cells were plated into culture plates at 30% confluency and incubated in DMEM+10% FBS at 37° C. in 5%

$CO_2$ for 48 hours. Then, the medium was replaced with fresh DMEM+10% FBS, and NK cells were added with the effector to target cell ratios (i.e., E:T, ratio of cell numbers) as follows: NK:A549=20:1, 10:1, 5:1, 2.5:1, and 1.25:1, respectively. The killing processes at each E:T ratio were carried out for 24 hours and 48 hours, respectively, with the cells being incubated at 37° C. in 5% $CO_2$. Afterwards, Trypan Blue Staining method was used for counting the living A549 cells, and the killing rates of A549 cells by NK cells were calculated relative to the control group in which no NK cells were added. The X axis of the dose-response curve represents E:T ratio, and Y axis represents the percentage value of inhibition rate (IR). The result of the experiment with killing time (i.e., the period from the time when NK cells were introduced to the tumor cells culture to the time when the killing was detected) being 48 hours is shown in FIG. 1, which exhibits an inhibition rate of about 14% when E:T ratio is 5:1, indicating a suitable dose level. This dosage was adopted as the dose level of NK cells to be used in the combined killing experiment. The killing effect was much weaker when the killing time was 24 hours compared to that when the killing time was 48 hours. Therefore, the suitable length of killing time for the NK cells was about 48 hours.

Experimental Example A2: Dose-Response Experiment of H101 Against A549 Cells

Figure 2:
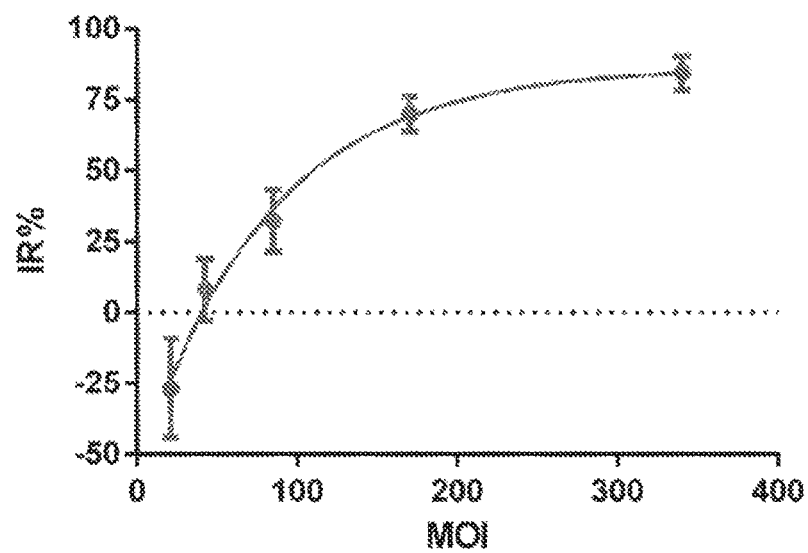
FIG. 2 shows the result of a dose-response experiment of the oncolytic virus H101 against A549 cells in Experimental example A2 according to the present disclosure.

A549 cells were plated into culture plates at 30% confluency and incubated in DMEM+10% FBS at 37° C. in 5% $CO_2$ for 24 hours. Then, the medium was replaced with fresh serum-free DMEM, and H101 was added with MOI being 340, 170, 85, 42.5 and 21.25, respectively. The time point at which H101 was added was taken as 0 hour (the same below). The infection process lasted for 6 hours with the cells being incubated at 37° C. In 5% $CO_2$, then the medium was removed, and the cells were washed with PBS. Then, fresh DMEM+10% FBS was added, and the cells were further incubated to 72 hours. Afterwards, Trypan Blue Staining method was used for counting the living A549 cells, and the killing rates of A549 cells by H101 were calculated relative to the control group in which no H101 was added. FIG. 2 shows the dose-response curve (wherein X axis represents MOI, and Y axis represents the percentage value of inhibition rate (IR)), which exhibits an inhibition rate of about 37% when the dose level of H101 against A549 cells is the MOI being about 85, indicating a suitable dose level. This dosage was adopted as the dose level of H101 to be used in the combined killing experiment.

Experimental Example A3: Length of Time Experiment for Infection of A549 Cells with H101

Different lengths of time for infection of A549 cells with H101 were studied to achieve a suitable infection effect. A549 cells were plated into culture plates at 30% confluency and incubated in DMEM+10% FBS at 37° C. In 5% $CO_2$ for 24 hours. Then, the medium was replaced with either serum-free DMEM or DMEM+10% FBS, and H101 was added (MOI=85). For cells in the serum-free DMEM environment, the infection process lasted for 2 or 6 hours, respectively. For cells in the DMEM+10% FBS environment, the infection process lasted for 24 hours. All the infection processes were carried out at 37° C. in 5% $CO_2$. After the viruses were washed off, fresh DMEM+10% FBS was added and the cells were incubated at 37° C. In 5% $CO_2$ to 24 hours, 48 hours or 72 hours, respectively. Afterwards, living A549 cells were counted using Trypan Blue Staining method and the inhibition rates of A549 cells were compared.

The results indicated that the suitable length of time for the infection of A549 cells with H101 was about 6 hours in serum-free environment, and the suitable length of time for the intracellular replication of H101 was about 24 hours.

Example A4: Combined Killing Experiment of H101 and NK

It can be concluded from the above Experimental examples that the suitable dose level for the killing of H101 against A549 was the MOI being about 85; the suitable length of time for the infection of A549 cells with H101 was about 6 hours; the suitable length of time for the intracellular replication of H101 was about 24 hours; the suitable dose level for the killing of NK cells against A549 cells was the E:T ratio (i.e., NK:A549) being about 5:1; and the suitable length of time for the killing of NK cells was about 48 hours.

A549 cells were plated into culture plates at 30% confluency and incubated in DMEM+10% FBS at 37° C. in 5% $CO_2$ for 24 hours. Then, the medium was replaced with serum-free DMEM, and H101 was added (MOI=85). After a six-hour infection, the medium was replaced with DMEM+10% FBS, and the cells were incubated at 37° C. in 5% $CO_2$ to 24 hours. The medium was replaced with fresh DMEM+10% FBS, and NK cells were added (E:T ratio (NK:A549)=5:1), and the cells were further incubated to 48 hours. Dead cells and debris were washed off, and Trypan Blue Staining method was used for counting the remaining living A549 cells. In the experiment, there were also a blank control group, in which none of the virus or NK cells were added to A549 cells; a H101 group, in which H101 was added at its corresponding time point but no NK cells were added; and a NK group, in which the NK cells were added at their corresponding time point but no H101 was added. All the control groups underwent the corresponding medium replacement operations at corresponding times. All the experiments were repeated for over 3 times, and the averages were used for statistical analysis.

Figure 3:
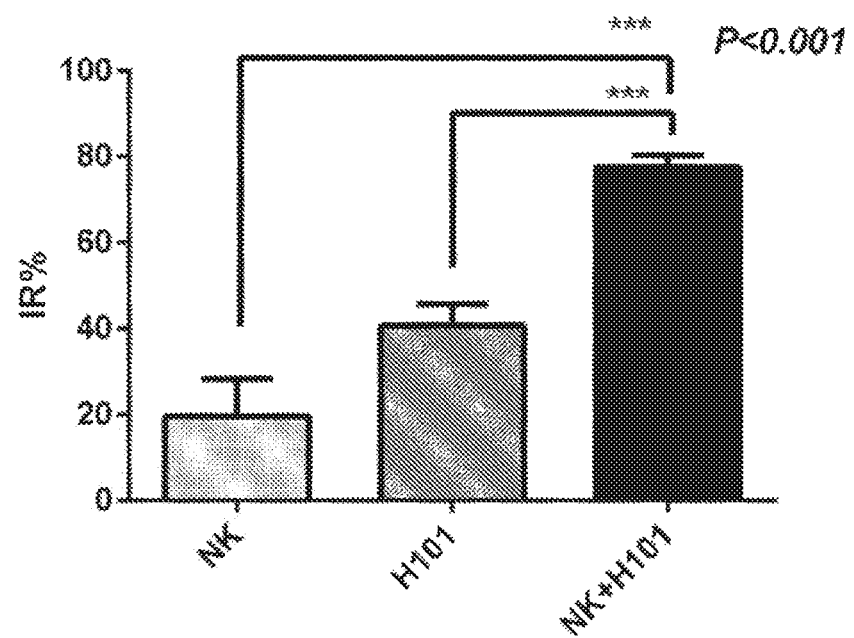
FIG. 3 shows the result of the combined killing experiment of H101 and NK cells in Example A4 according to the present disclosure.

As shown in FIG. 3 (wherein X axis represents the different groups, and Y axis represents the corresponding percentage values of inhibition rates), the combined application of H101 and NK cells (the oncolytic virus being administered first and the NK cells later) had significant synergistic killing effect against A549 cells, and the synergistic inhibition rate was about 78%. However, in this experiment, the inhibition rate of single application of H101 was about 41% and the inhibition rate of single application of the NK cells was about 20%.

In another experiment which was similar to the one above with the exception that, after infection by adding H101, the cells were incubated to 48 hours instead of 24 hours, the results also demonstrated that combined application of H101 and NK cells (the oncolytic virus being administered first and the NK cells later) had significant synergistic killing effect against A549 cells, and the synergistic inhibition rate was about 80%.

Comparative Example A5: Simultaneous Combined Administration of the Drugs

A549 cells were plated into culture plates at 30% confluency and incubated in DMEM+10% FBS at 37° C. in 5% $CO_2$ for 24 hours. Then, the medium was replaced with fresh DMEM+10% FBS, and H101 (MOI=85) and NK cells (E:T ratio (NK:A549)=5:1) were added simultaneously. The cells were further incubated for 72 hours, then dead cells and debris were washed off, and the remaining living A549 cells were counted using Trypan Blue Staining method. In the experiment, there were also a blank control group, in which none of the virus or NK cells were added to A549 cells; a H101 group, in which H101 was added at its corresponding time point but no NK cells were added; and a NK group, in which the NK cells were added at their corresponding time point but no H101 was added. All the control groups underwent the corresponding medium replacement operation at the corresponding time. All the experiments were repeated over 3 times, and the averages were used for statistical analysis.

Figure 4:
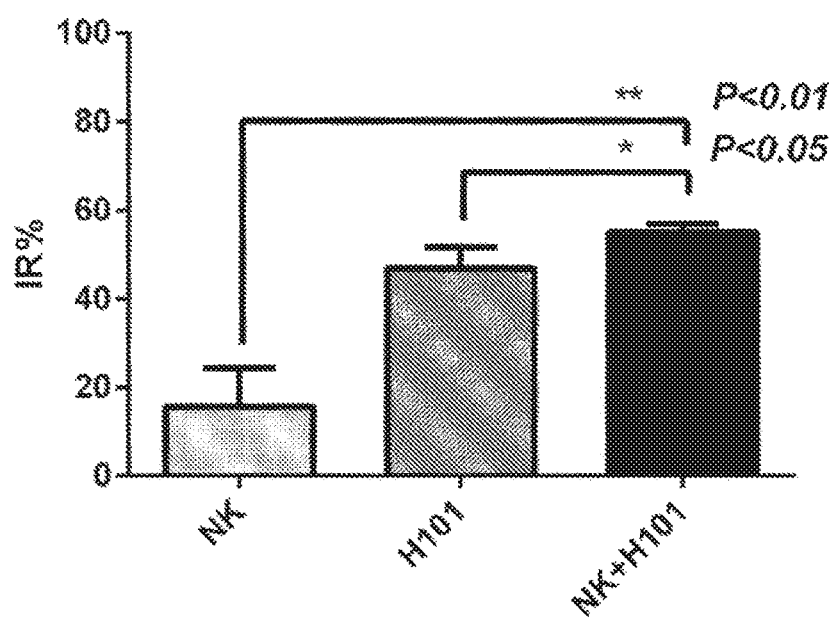
FIG. 4 shows the result of the simultaneous combined administration of H101 and NK cells in Comparative example A5 according to the present disclosure.
Figure 5:
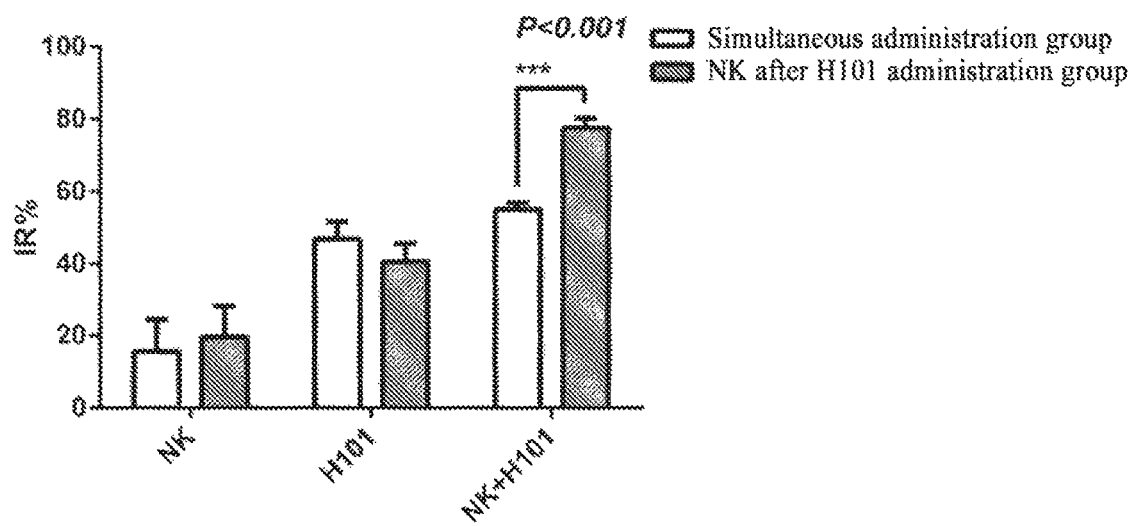
FIG. 5 shows a comparison between the result of the combined killing experiment of H101 and NK cells in Example A4 and the result of the simultaneous combined administration of H101 and NK cells in Comparative example A5 according to the present disclosure.

As shown in FIG. 4 (wherein X axis represents the different groups, and Y axis represents the corresponding percentage values of inhibition rates), the inhibition rate of the single application of H101 was about 47% and the inhibition rate of the single application of NK cells was about 16%. Compared to these single applications, the inhibition rate of combined use of NK cells and H101 was increased, which was about 55%; however, no significant synergistic effect was shown as compared to Example A4 (see the comparison shown in FIG. 5, wherein X axis represents the different groups, and Y axis represents the corresponding percentage values of inhibition rates).

The above results indicate that 1) the combined application of H101 and NK cells has superior efficacy than the single application of either H101 or NK cells; and 2) the timing of administration can significantly affect the efficacy of the combined application of H101 and NK cells—when H101 and NK cells were substantially administered simultaneously, the combined application did not show a synergistic effect; whereas when NK cells were administered about 24 to 48 hours after the administration of H101, the combined application showed a significant synergistic effect.

Comparative Example A6: Comparison Between Different Administration Sequences in Combined Application A549 cells were plated into culture plates at 30% confluency and incubated in DMEM+10% FBS at 37° C. in 5% $CO_2$ for 24 hours. Then, the medium was replaced with fresh DMEM+10% FBS, and NK cells were added (E:T ratio (NK:A549)=5:1). The cells were incubated at 37° C. in 5% $CO_2$ for 24 hours. Then, H101 (MOI=85) was added without replacing the medium, and the cells were further incubated for 48 hours. Dead cells and debris were washed off, and Trypan Blue Staining method was used for counting the remaining living A549 cells. In the experiment, there were also a blank control group, in which none of the virus or NK cells were added to A549 cells; a H101 group, in which H101 was added at its corresponding time point but no NK cells were added; and a NK group, in which the NK cells were added at their corresponding time point but no H101 was added. All the control groups underwent the corresponding medium replacement operation at the corresponding time. All the experiments were repeated for over 3 times, and the averages were used for statistical analysis.

Figure 6:
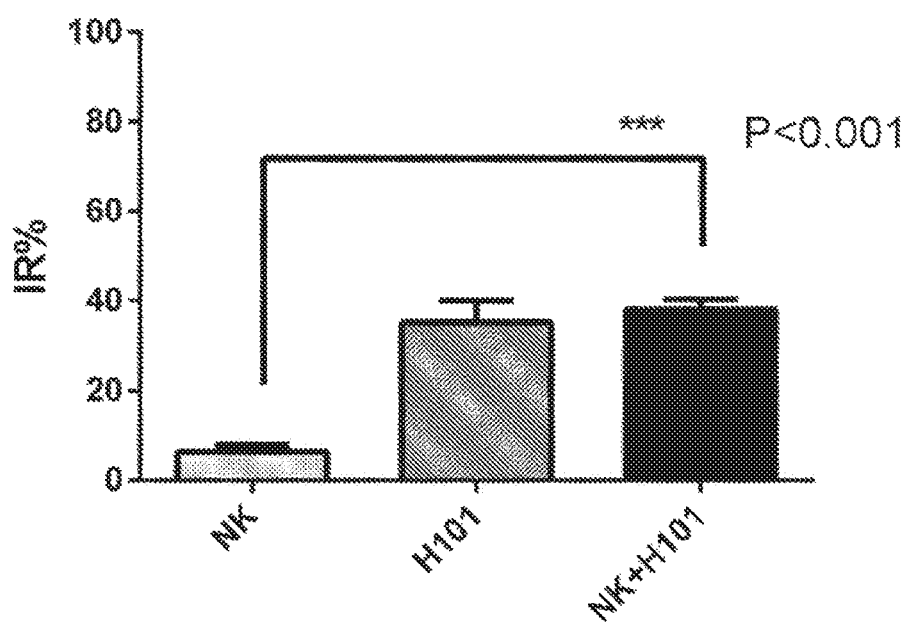
FIG. 6 shows the result of the combined administration of H101 and NK cells in a reverse sequential manner in Comparative example A6 according to the present disclosure.

As shown in FIG. 6 (wherein X axis represents the different groups, and Y axis represents the corresponding percentage values of inhibition rates), the inhibition rate of the combined application in a reverse sequential manner (NK cells being administered first and H101 later) was about 38%, the inhibition rate of the single application of H101 was about 35%, and the inhibition rate of the single application of NK cells was about 6%. The inhibition rate of the single application of NK cells against A549 cells for 72 hours was lower than that for 48 hours. This may be because A549 cells have a fast growth rate but a relatively poor sensitivity to NK cells, and the killing effect of NK cells has short-term characteristics. Thus, those A549 cells that were not killed by NK cells proliferated rapidly, resulting in that the inhibition rate of the killing for 72 hours was lower than that for 48 hours. The combined application in the reverse sequential manner did not show a synergistic effect.

Comparative Example A7: Combined Application of the Drugs in Normal Cells

HUVEC cells (Human Umbilical Vein Endothelial Cells) were plated into culture plates with gelatin, at 30% confluency, and cultured in a proper complete medium (HUVEC cells and complete medium were purchased from ALLCELLS LLC; Item No. H-003) at 37° C. in 5% $CO_2$ for 24 hours. Then, the medium was replaced with a fresh complete medium, and H101 (MOI=85) was added and the infection process lasted for 6 hours. Then, the medium was replaced with a fresh complete medium, and the cells were incubated at 37° C. in 5% $CO_2$ to 24 hours. Afterwards, the medium was replaced with a fresh complete medium, then NK cells were added (E:T ratio (NK:HUVEC)=5:1), and the cells were further incubated for 48 hours. Dead cells and debris were washed off and Trypan Blue Staining method was used for counting the remaining living HUVEC cells. In the experiment, there were also a blank control group, in which none of the virus or NK cells were added to HUVEC cells; a H101 group, in which H101 was added at its corresponding time point but no NK cells were added; and a NK group, in which NK cells were added at their corresponding time point but no H101 was added. All the control groups underwent the corresponding medium replacement operations at corresponding times. All the experiments were repeated for over 3 times, and the averages were used for statistical analysis.

Figure 7:
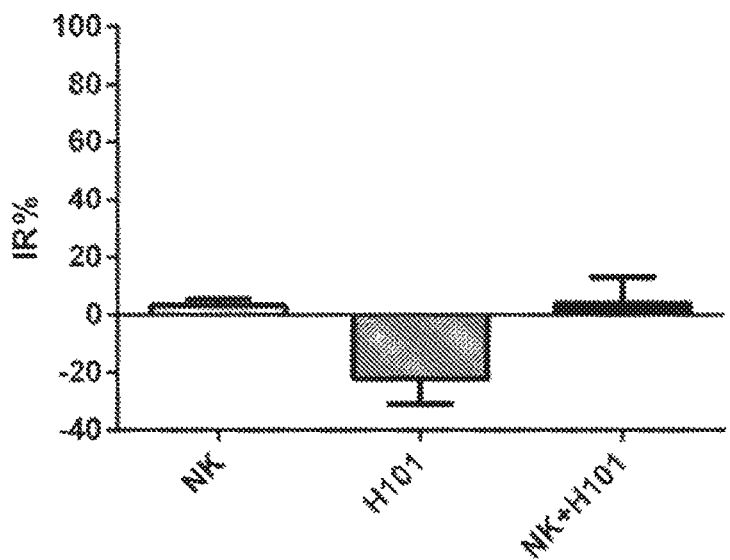
FIG. 7 shows the killing effect of combined administration of H101 and NK cells on normal cells in Comparative example A7 according to the present disclosure.

As shown in FIG. 7 (wherein X axis represents the different groups, and Y axis represents the corresponding percentage values of inhibition rates), the combined application of NK cells and H101 had no killing effect against the normal human primary cells HUVEC. The single application of H101 or single application of NK cells had no killing effect against the normal human primary cells HUVEC either.

Example A8: Dose Escalation Study of Combined Administrations

A549 cells were plated into culture plates at 30% confluency, and incubated in DMEM+10% FBS at 37° C. in 5% $CO_2$ for 24 hours. In the first group, the medium was replaced with serum-free DMEM, then H101 (MOI=85) was added, and the infection process lasted for 6 hours. The medium was then replaced with fresh DMEM+10% FBS, and the cells were incubated to 24 hours. Then, the medium was replaced with fresh DMEM+10% FBS, and NK cells at various dose levels (E:T=1:1, 5:1, 10:1, 15:1, or 20:1) were added respectively, and the cultures were further incubated for 48 hours. Dead cells and debris were washed off, and Trypan Blue Staining method was used for counting the remaining living A549 cells. In the second group, after the medium was replaced with fresh DMEM+10% FBS, H101 (MOI=85) and NK cells were added simultaneously, with the dose level of NK cells being E:T=1:1, 5:1, 10:1, 15:1, or 20:1, respectively, and the cells were further incubated for 72 hours. Dead cells and debris were washed off, and Trypan Blue Staining method was used for counting the remaining living A549 cells. In the third group, after the medium was replaced with fresh DMEM+10% FBS, NK cells at various dose levels (E:T=1:1, 5:1, 10:1, 15:1, or 20:1) were respectively added first, and the cultures were incubated for 24 hours. Then, H101 at the same dose level (MOI=85) was added without replacing the medium, the cultures were further incubated for 48 hours. Dead cells and debris were washed off, and Trypan Blue Staining method was used for counting the remaining living A549 cells. In the experiment, there was also a blank control group, in which none of the virus or NK cells were added to A549 cells. The control group underwent the corresponding medium replacement operations at the corresponding times. All the experiments were repeated for over 3 times, and the averages were used for statistical analysis.

Figure 8:
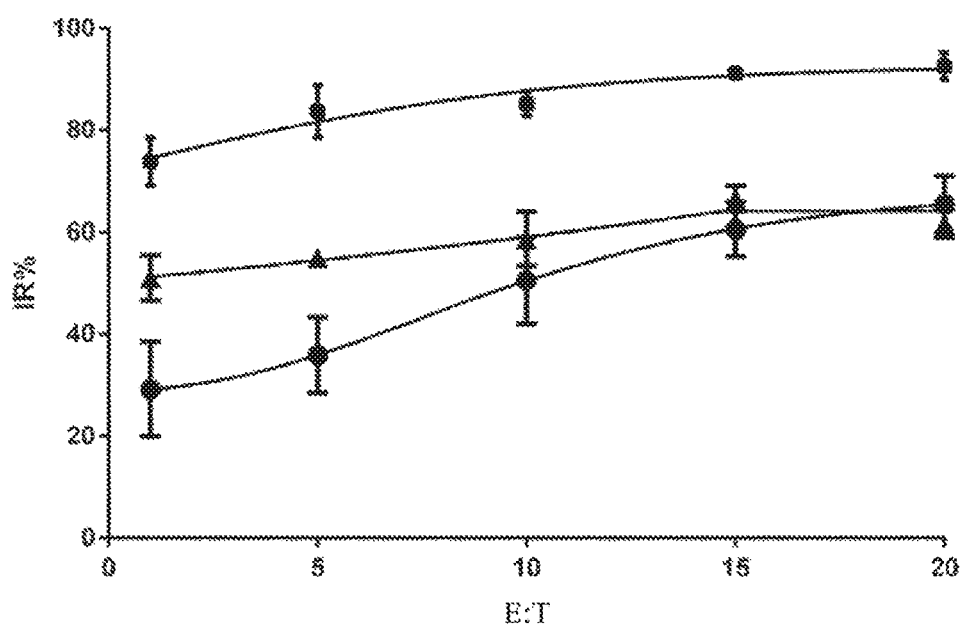
FIG. 8 shows the results of a dose escalation study of combined administrations in Example A8 according to the present disclosure. The curve connecting the squares represents the killing effect against A549 cells when H101 was given first and NK cells were given later; the curve connecting the triangles represents the killing effect against A549 cells when H101 and NK cells were given simultaneously; and the curve connecting the circles represents the killing effect against A549 cells when NK cells were given first and H101 was given later.

As shown in FIG. 8 (wherein X axis represents E:T ratios, and Y axis represents the corresponding percentage values of inhibition rates), in the combined application, there was a positive correlation between the dose level of NK cells and its killing effect, and when the dose levels of H101 and NK cells were unchanged respectively, the killing effect of the combination that H101 was administered first and NK cells later was significantly greater than the killing effect of the combination that H101 and NK cells were administered simultaneously or the killing effect of the combination that NK cells were administered first and H101 later.

Figure 9:
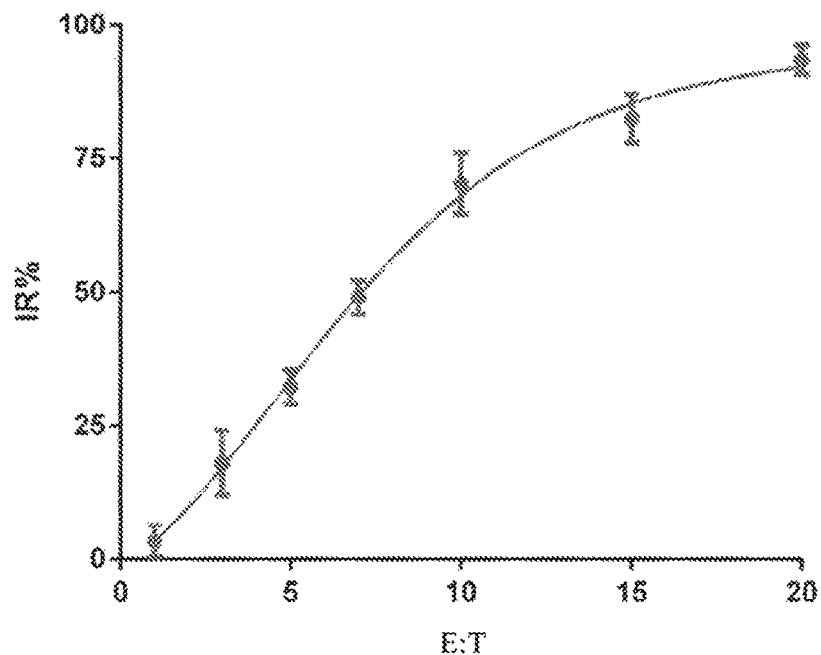
FIG. 9 shows the result of a dose-response experiment of NK cells against HepG2 cells in Experimental example B1 according to the present disclosure.

B: Study on the Killing Effect of Combined Application of Oncolytic Adenovirus and NK Cells Against HepG2 Cells Experimental Example B1: Dose-Response Experiment of NK Cells Against HepG2 Cells HepG2 cells were plated into culture plates at 30% confluency and incubated in DMEM+10% FBS at 37° C. In 5% $CO_2$ for 48 hours. Then, the medium was replaced with fresh DMEM+10% FBS, and NK cells were added with the effector to target cell ratios (i.e., E:T, ratio of cell numbers) as follows: NK:HepG2=20:1, 15:1, 10:1, 7:1, 5:1, 3:1, and 1:1, respectively. The killing process at each E:T ratio lasted for 48 hours with the cells being incubated at 37° C. in 5% $CO_2$. Afterwards, Trypan Blue Staining method was used for counting the living HepG2 cells, and the killing rates of HepG2 cells by NK cells were calculated relative to the control group in which no NK cells were added. FIG. 9 shows the dose-response curve (wherein X axis represents E:T ratio, and Y axis represents the percentage value of inhibition rate (IR)), which exhibits an inhibition rate of about 18% when E:T ratio is 3:1, indicating a suitable dose level. This dosage was adopted as the dose level of NK cells to be used in the combined killing experiment.

Experimental Example B2: Dose-Response Experiment of H101 Against HepG2 Cells

Figure 10:
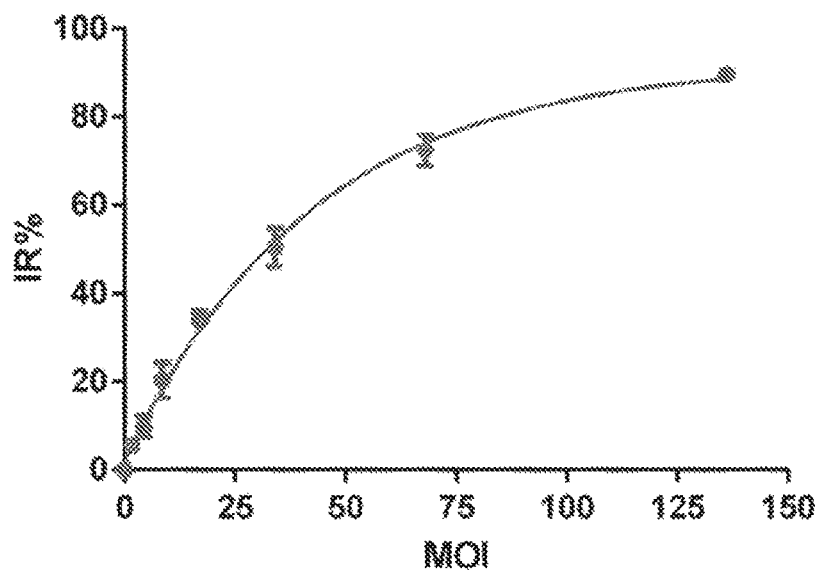
FIG. 10 shows the result of a dose-response experiment of H101 against HepG2 cells in Experimental example B2 according to the present disclosure.

HepG2 cells were plated into culture plates at 30% confluency and incubated in DMEM+10% FBS at 37° C. in 5% $CO_2$ for 24 hours. Then, the medium was replaced with fresh serum-free DMEM, and H101 was added with MOI being 136, 68, 34, 17, 8.5, 4.25, and 1.7, respectively. The infection process lasted for 6 hours with the cells being incubated at 37° C. in 5% $CO_2$, then the medium was removed, and the cells were washed with PBS. Then, fresh DMEM+10% FBS was added, and the cells were further incubated to 72 hours. Afterwards, Trypan Blue Staining method was used for counting the living HepG2 cells, and the killing rates of HepG2 cells by H101 were calculated relative to the control group in which no H101 was added. FIG. 10 shows the dose-response curve (wherein X axis represents MOI, and Y axis represents the percentage value of inhibition rate (IR)), which exhibits an inhibition rate of about 27% when the dose level of H101 against HepG2 cells is the MOI being about 13.6, indicating a suitable dose level. This dosage was adopted as the dose level of H101 to be used in the combined killing experiment.

Example B3: Combined Killing Experiment of H101 and NK

It can be concluded from the above Experimental examples that the suitable dose level for the killing of H101 against HepG2 cells was the MOI being about 13.6; and the suitable dose level for the killing of NK cells against HepG2 cells was the E:T ratio (i.e., NK:HepG2) being about 3:1.

HepG2 cells were plated into culture plates at 30% confluency and incubated in DMEM+10% FBS at 37° C. in 5% $CO_2$ for 24 hours. Then, the medium was replaced with serum-free DMEM, and H101 was added (MOI=13.6). After a six-hour infection, the medium was replaced with DMEM+10% FBS, and the cells were incubated at 37° C. in 5% $CO_2$ to 48 hours. The medium was replaced with fresh DMEM+10% FBS, and NK cells were added (E:T ratio (NK:HepG2)=3:1), and the cells were further incubated for 48 hours. Dead cells and debris were washed off, and Trypan Blue Staining method was used for counting the remaining living HepG2 cells. In the experiment, there were also a blank control group, in which none of the virus or NK cells were added to HepG2 cells; a H101 group, in which H101 was added at its corresponding time point but no NK cells were added; and a NK group, in which the NK cells were added at their corresponding time point but no H101 was added. All the control groups underwent the corresponding medium replacement operations at corresponding times. All the experiments were repeated for over 3 times, and the averages were used for statistical analysis.

Figure 11:
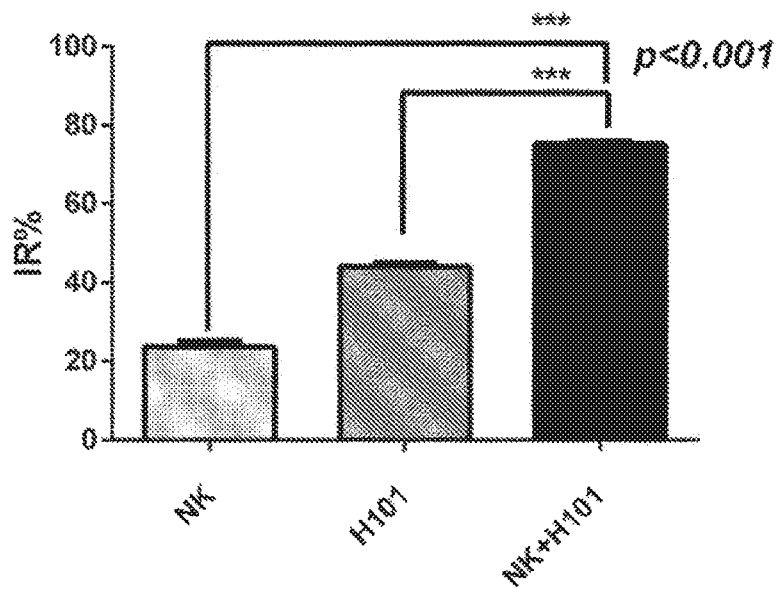
FIG. 11 shows the result of the combined killing experiment of H101 and NK cells in Example B3 according to the present disclosure.

As shown in FIG. 11 (wherein X axis represents the different groups, and Y axis represents the corresponding percentage values of inhibition rates), the combined application of H101 and NK cells (the oncolytic virus being administered first and the NK cells later) had significant synergistic killing effect against HepG2 cells, and the synergistic inhibition rate was about 75%. However, in this experiment, the inhibition rate of single application of H101 was about 44% and the inhibition rate of single application of the NK cells was about 24%.

Comparative Example B4: Simultaneous Combined Administration of the Drugs

HepG2 cells were plated into culture plates at 30% confluency and incubated in DMEM+10% FBS at 37° C. in 5% $CO_2$ for 24 hours. Then, the medium was replaced with serum-free DMEM, and H101 was added (MOI=13.6). After a six-hour infection, the medium was replaced with DMEM+10% FBS, and NK cells were added (E:T ratio (NK:HepG2)=3:1). The cells were further incubated to 96 hours, then dead cells and debris were washed off, and the remaining living HepG2 cells were counted using Trypan Blue Staining method. In the experiment, there were also a blank control group, in which none of the virus or NK cells were added to HepG2 cells; a H101 group, in which H101 was added at its corresponding time point but no NK cells were added; and a NK group, in which the NK cells were added at their corresponding time point but no H101 was added. All the control groups underwent the corresponding medium replacement operations at corresponding times. All the experiments were repeated for over 3 times, and the averages were used for statistical analysis.

Figure 12:
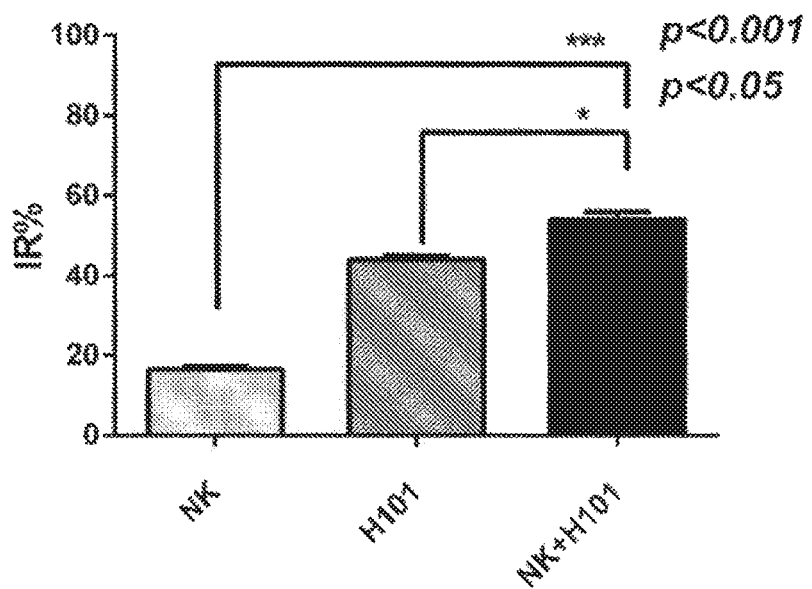
FIG. 12 shows the result of the simultaneous combined administration of H101 and NK cells in Comparative example B4 according to the present disclosure.
Figure 13:
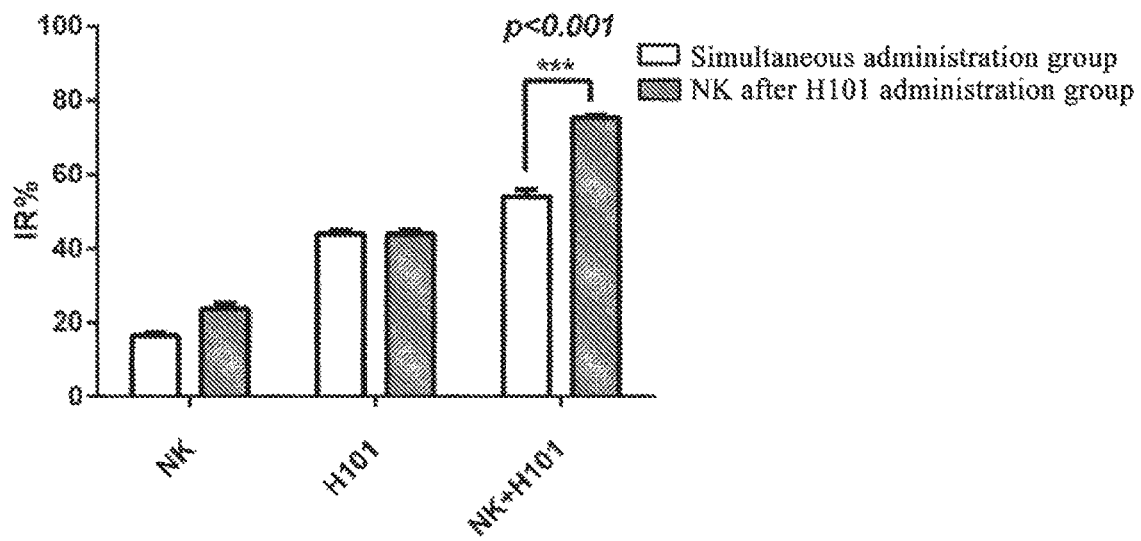
FIG. 13 shows a comparison between the result of the combined killing experiment of H101 and NK cells in Example B3 and the result of the simultaneous combined administration of H101 and NK cells in Comparative example B4 according to the present disclosure.

As shown in FIG. 12 (wherein X axis represents the different groups, and Y axis represents the corresponding percentage values of inhibition rates), the inhibition rate of the single application of H101 was about 44% and the inhibition rate of single application of the NK cells was about 17%. Compared to these single applications, the inhibition rate of combined use of NK cells and H101 was increased, which was about 54%; however, no significant synergistic effect was shown as compared to Example B3 (see the comparison shown in FIG. 13, wherein X axis represents the different groups, and Y axis represents the corresponding percentage values of inhibition rates).

The above results indicate that 1) the combined application of H101 and NK cells has superior efficacy than the single application of either H101 or NK cells; and 2) the timing of administration can significantly affect the efficacy of the combined application of H101 and NK cells—when H101 and NK cells were substantially administered simultaneously, the combined application did not show a synergistic effect; whereas when H101 was administered first and NK cells later, the combined application showed a significant synergistic effect.

Comparative Example B5: Comparison Between Different Administration Sequences in Combined Application HepG2 cells were plated into culture plates at 30% confluency and incubated in DMEM+10% FBS at 37° C. in 5% $CO_2$ for 24 hours. Then, the medium was replaced with fresh DMEM+10% FBS, and NK cells were added (E:T ratio (NK:HepG2)=3:1). The cells were incubated at 37° C. in 5% $CO_2$ for 48 hours. Then, H101 (MOI=13.6) was added without replacing the medium, and the cells were further incubated for 48 hours. Dead cells and debris were washed off, and Trypan Blue Staining method was used for counting the remaining living HepG2 cells. In the experiment, there were also a blank control group, in which none of the virus or NK cells were added to HepG2 cells; a H101 group, in which H101 was added at its corresponding time point but no NK cells were added; and a NK group, in which the NK cells were added at their corresponding time point but no H101 was added. All the control groups underwent the corresponding medium replacement operation at corresponding time. All the experiments were repeated for over 3 times, and the averages were used for statistical analysis.

Figure 14:
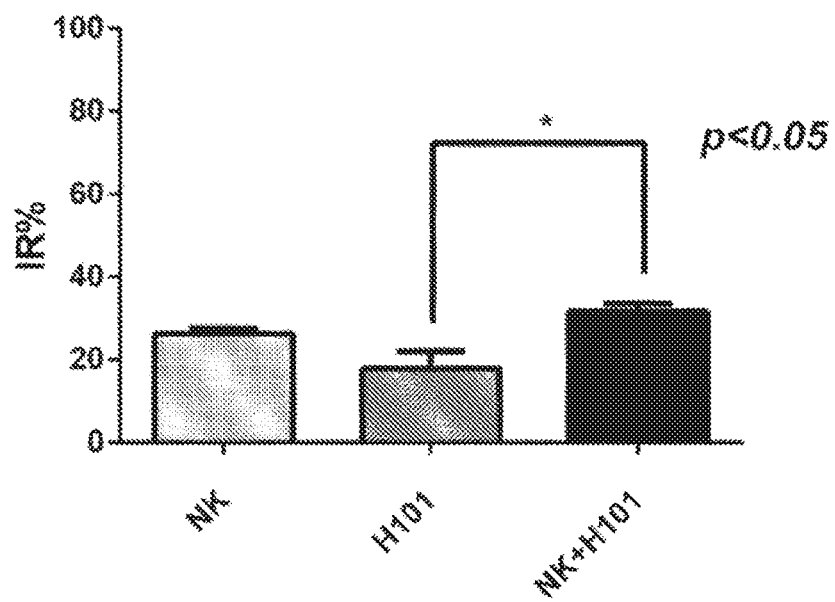
FIG. 14 shows the result of the combined administration of H101 and NK cells in a reverse sequential manner in Comparative example B5 according to the present disclosure.

As shown in FIG. 14 (wherein X axis represents the different groups, and Y axis represents the corresponding percentage values of inhibition rates), the inhibition rate of the combined application in a reverse sequential manner (NK cells being administered first and H101 later) was about 32%, the inhibition rate of the single application of H101 was about 18%, and the inhibition rate of single application of the NK cells was about 26%. The combined application in the reverse sequential manner did not show a synergistic effect.

Example B6: Dose Escalation Study of Combined Administrations

HepG2 cells were plated into culture plates at 30% confluency and incubated in DMEM+10% FBS at 37° C. in 5% $CO_2$ for 24 hours. In the first group, the medium was replaced with serum-free DMEM, then H101 (MOI=13.6) was added, and the infection process lasted for 6 hours. The medium was then replaced with fresh DMEM+10% FBS, and the cells were incubated to 48 hours. Then, the medium was replaced with fresh DMEM+10% FBS, and NK cells at various dose levels (E:T=1:1, 2:1, 3:1, 4:1, or 5:1) were added respectively, and the cells were further incubated for 48 hours. Dead cells and debris were washed off, and Trypan Blue Staining method was used for counting the remaining living HepG2 cells. In the second group, the medium was replaced with serum-free DMEM, and H101 (MOI=13.6) was added, and the infection process lasted for 6 hours. Then, the medium was replaced with fresh DMEM+10% FBS, and NK cells at various dose levels (E:T=1:1, 2:1, 3:1, 4:1, or 5:1) were added respectively. The cells were further incubated to 96 hours, then dead cells and debris were washed off, and the remaining living HepG2 cells were counted using Trypan Blue Staining method. In the third group, after the medium was replaced with fresh DMEM+10% FBS, NK cells at various dose levels (E:T=1:1, 2:1, 3:1, 4:1, or 5:1) were added respectively, and the cells were incubated for 48 hours. Then, the same dose of H101 (MOI=13.6) was added without replacing the medium, and the cells were further incubated for 48 hours. Dead cells and debris were washed off, and Trypan Blue Staining method was used for counting the remaining living HepG2 cells. In the experiment, there was also a blank control group, in which none of the virus or NK cells were added to HepG2 cells. The control group underwent the corresponding medium replacement operations at the corresponding times. All the experiments were repeated for over 3 times, and the averages were used for statistical analysis.

Figure 15:
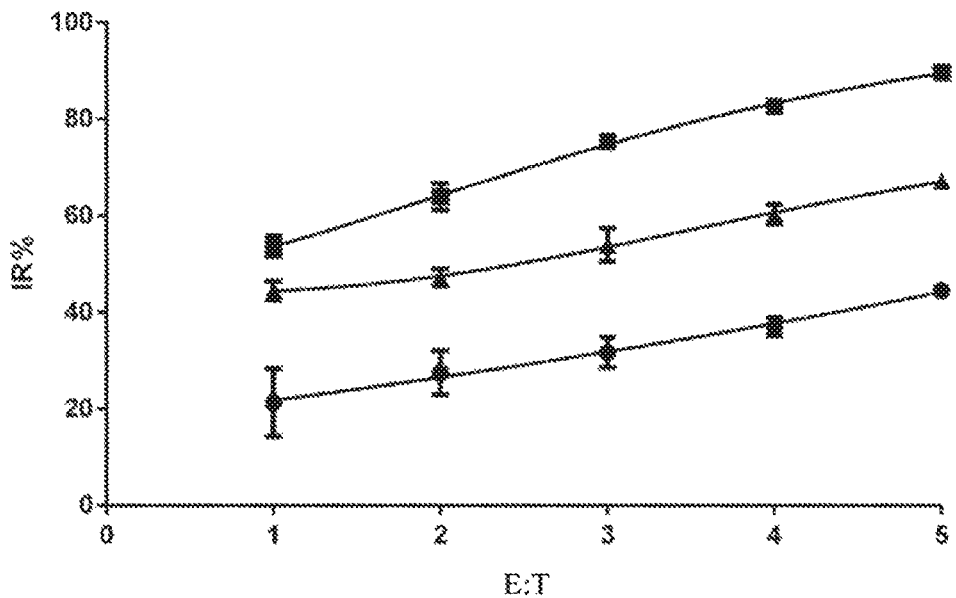
FIG. 15 shows the results of a dose escalation study of combined administrations in Example B6 according to the present disclosure. The curve connecting the squares represents the killing effect against HepG2 cells when H101 was given first and NK cells were given later; the curve connecting the triangles represents the killing effect against HepG2 cells when H101 and NK cells were given simultaneously; and the curve connecting the circles represents the killing effect against HepG2 cells when NK cells were given first and H101 was given later.

As shown in FIG. 15 (wherein X axis represents E:T ratios, and Y axis represents the corresponding percentage values of inhibition rates), in the combined application, there was a positive correlation between the dose level of NK cells and its killing effect, and when the dose levels of H101 and NK cells were unchanged respectively, the killing effect of the combination that H101 was administered first and NK cells later was significantly greater than the killing effect of the combination that H101 and NK cells were administered simultaneously or the killing effect of the combination that NK cells were administered first and H101 later.

Figure 16:
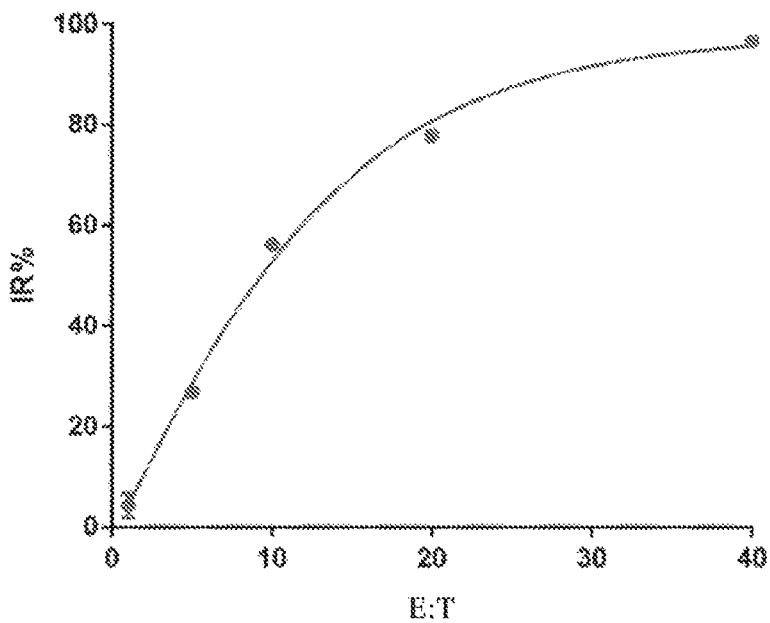
FIG. 16 shows the result of a dose-response experiment of NK cells against HT29 cells in Experimental example C1 according to the present disclosure.

C: Study on the Killing Effect of Combined Application of Oncolytic Adenovirus and NK Cells Against HT29 Cells Experimental Example C1: Dose-Response Experiment of NK Cells Against HT29 Cells HT29 cells were plated into culture plates at 30% confluency and incubated in DMEM+10% FBS at 37° C. in 5% $CO_2$ for 48 hours. Then, the medium was replaced with fresh DMEM+10% FBS, and NK cells were added with the effector to target cell ratios (i.e., E:T, ratio of cell numbers) as follows: NK:HT29=40:1, 20:1, 10:1, 5:1, and 1:1, respectively. The killing process at each E:T ratio lasted for 48 hours with the cells being incubated at 37° C. in 5% $CO_2$. Afterwards, Trypan Blue Staining method was used for counting the living HT29 cells, and the killing rates of HT29 cells by NK cells were calculated relative to the control group in which no NK cells were added. FIG. 16 shows the dose-response curve (wherein X axis represents E:T ratio, and Y axis represents the percentage value of inhibition rate (IR)), which exhibits an inhibition rate of about 17% when E:T ratio is 3:1, indicating a suitable dose level. This dosage was adopted as the dose level of NK cells to be used in the combined killing experiment.

Experimental Example C2: Dose-Response Experiment of H101 Against HT29 Cells

Figure 17:
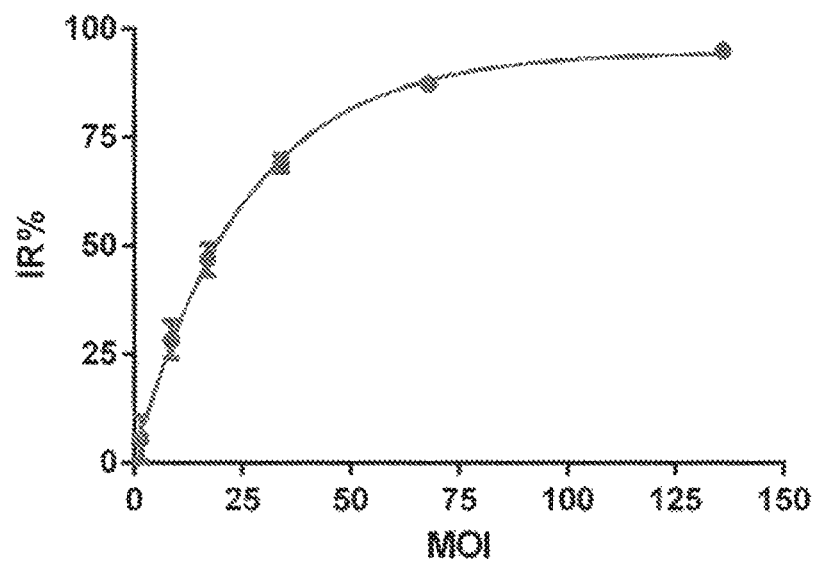
FIG. 17 shows the result of a dose-response experiment of H101 against HT29 cells in Experimental example C2 according to the present disclosure.

HT29 cells were plated into culture plates at 30% confluency and incubated in DMEM+10% FBS at 37° C. in 5% $CO_2$ for 24 hours. Then, the medium was replaced with fresh serum-free DMEM, and H101 was added with MOI being 136, 68, 34, 17, 8.5, and 1.7, respectively. The infection process lasted for 6 hours with the cells being incubated at 37° C. in 5% $CO_2$, then the medium was removed, and the cells were washed with PBS. Then, fresh DMEM+10% FBS was added, and the cells were further incubated to 72 hours. Afterwards, Trypan Blue Staining method was used for counting the living HT29 cells, and the killing rates of HT29 cells by H101 were calculated compared relative to the control group in which no H101 was added. FIG. 17 shows the dose-response curve (wherein X axis represents MOI, and Y axis represents the percentage value of inhibition rate (IR)), which exhibits an inhibition rate of about 40% when MOI is 13.6, indicating a suitable dose level. This dosage was adopted as the dose level of H101 to be used in the combined killing experiment.

Example C3: Combined Killing Experiment of H101 and NK

It can be concluded from the above Experimental examples that the suitable dose level for the killing of H101 against HT29 cells was the MOI being about 13.6; and the suitable dose level for the killing of NK cells against HT29 cells was the E:T ratio (i.e., NK:HT29) being about 3:1.

HT29 cells were plated into culture plates at 30% confluency and incubated in DMEM+10% FBS at 37° C. In 5% $CO_2$ for 24 hours. Then, the medium was replaced with serum-free DMEM, and H101 was added (MOI=13.6). After a six-hour infection, the medium was replaced with DMEM+10% FBS, and the cells were incubated at 37° C. in 5% $CO_2$ to 24 hours. The medium was replaced with fresh DMEM+10% FBS, and NK cells were added (E:T ratio (NK:HT29)=3:1), and the cells were further incubated for 48 hours. Dead cells and debris were washed off, and Trypan Blue Staining method was used for counting the remaining living HT29 cells. In the experiment, there were also a blank control group, in which none of the virus or NK cells were added to HT29 cells; a H101 group, in which H101 was added at its corresponding time point but no NK cells were added; and a NK group, in which the NK cells were added at their corresponding time point but no H101 was added. All the control groups underwent the corresponding medium replacement operations at corresponding times. All the experiments were repeated for over 3 times, and the averages were used for statistical analysis.

Figure 18:
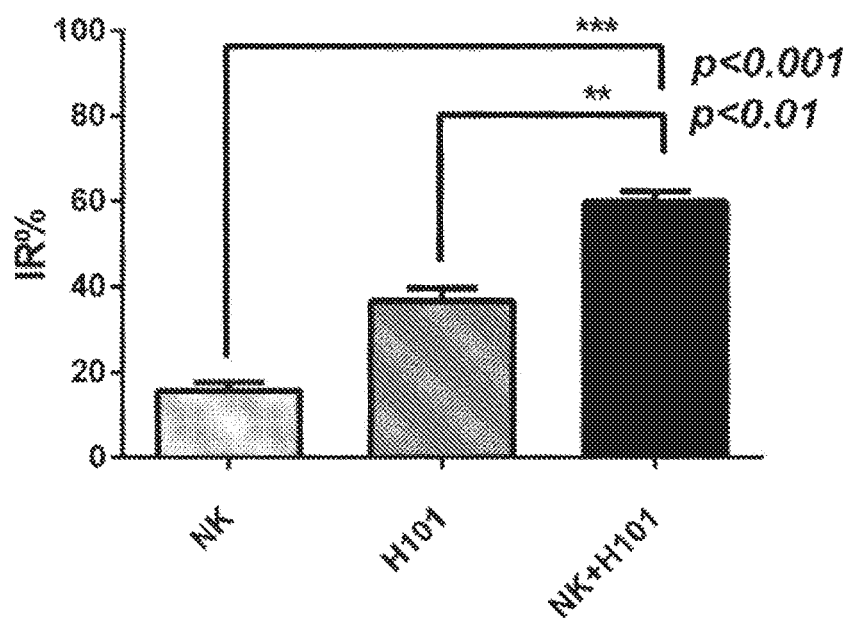
FIG. 18 shows the result of the combined killing experiment of H101 and NK cells administered at an interval of 24 hours in Example C3 according to the present disclosure.

As shown in FIG. 18 (wherein X axis represents the different groups, and Y axis represents the corresponding percentage values of inhibition rates), the combined application of H101 and NK cells (the oncolytic virus being administered first and the NK cells later) had significant synergistic killing effect against HT29 cells, and the synergistic inhibition rate was about 60%. However, in this experiment, the inhibition rate of single application of H101 was about 37% and the inhibition rate of single application of the NK cells was about 16%.

Example C4: Combined Killing Experiment of H101 and NK

Figure 23:
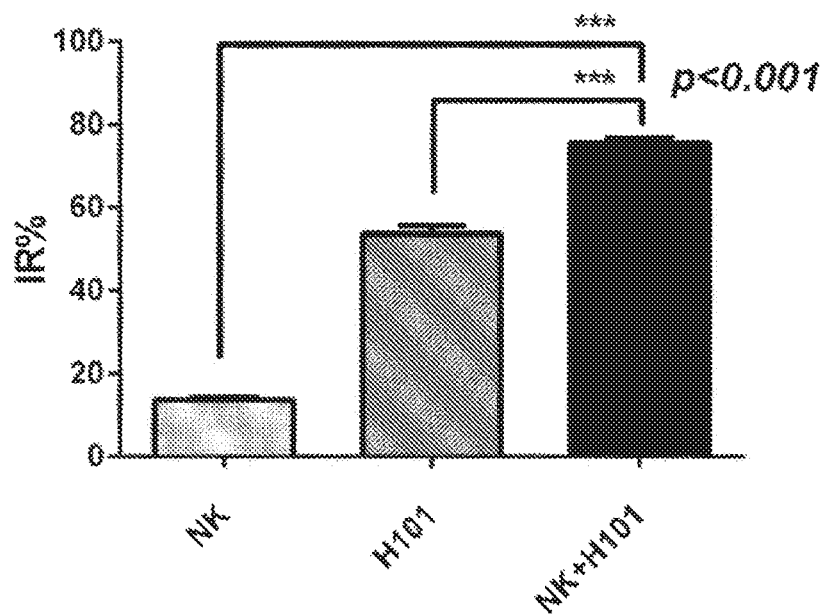
FIG. 23 shows the result of the combined killing experiment of H101 and NK cells administered at an interval of 48 hours in Example C4 according to the present disclosure.

Example C4 was similar to the above Example C3 except that, after infection by adding H101, the cells were incubated to 48 hours instead of 24 hours, and then NK cells were added. As shown in FIG. 23 (wherein X axis represents the different groups, and Y axis represents the corresponding percentage values of inhibition rates), the final result also demonstrated that the combined application of H101 and NK cells (the oncolytic virus being administered first and the NK cells later) had significant synergistic killing effect against HT29 cells, and the synergistic inhibition rate was about 76%. However, in this experiment, the inhibition rate of single application of H101 was about 54% and the inhibition rate of single application of the NK cells was about 14%.

Comparative Example C5: Simultaneous Combined Administration of the Drugs

HT29 cells were plated into culture plates at 30% confluency and incubated in DMEM+10% FBS at 37° C. in 5% $CO_2$ for 24 hours. Then, the medium was replaced with serum-free DMEM, and H101 was added (MOI=13.6). After a six-hour infection, the medium was replaced with fresh DMEM+10% FBS, and NK cells were added (E:T ratio (NK:HT29)=3:1). The cells were further incubated to 72 hours, then dead cells and debris were washed off, and the remaining living HT29 cells were counted using Trypan Blue Staining method. In the experiment, there were also a blank control group, in which none of the virus or NK cells were added to HT29 cells; a H101 group, in which H101 was added at its corresponding time point but no NK cells were added; and a NK group, in which the NK cells were added at their corresponding time point but no H101 was added. All the control groups underwent the corresponding medium replacement operations at corresponding times. All the experiments were repeated for over 3 times, and the averages ware used for statistical analysis.

Figure 19:
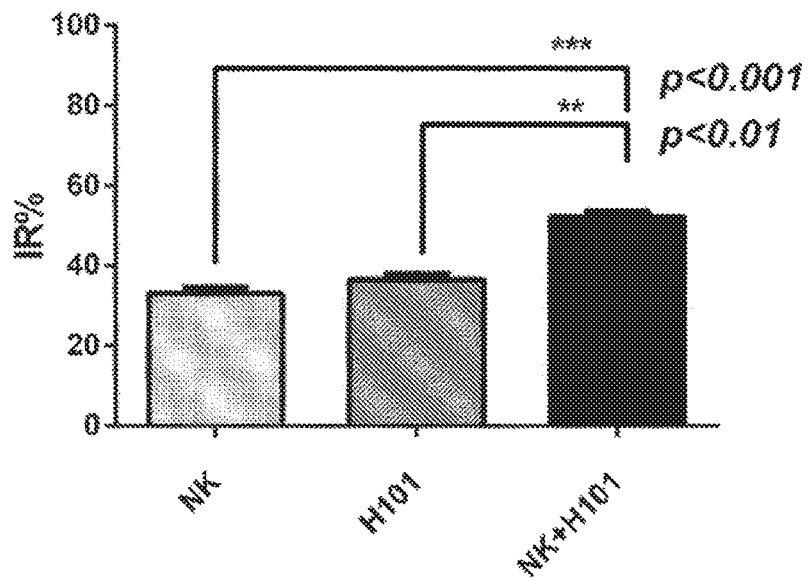
FIG. 19 shows the result of the simultaneous combined administration of H101 and NK cells in Comparative example C5 according to the present disclosure.
Figure 20:
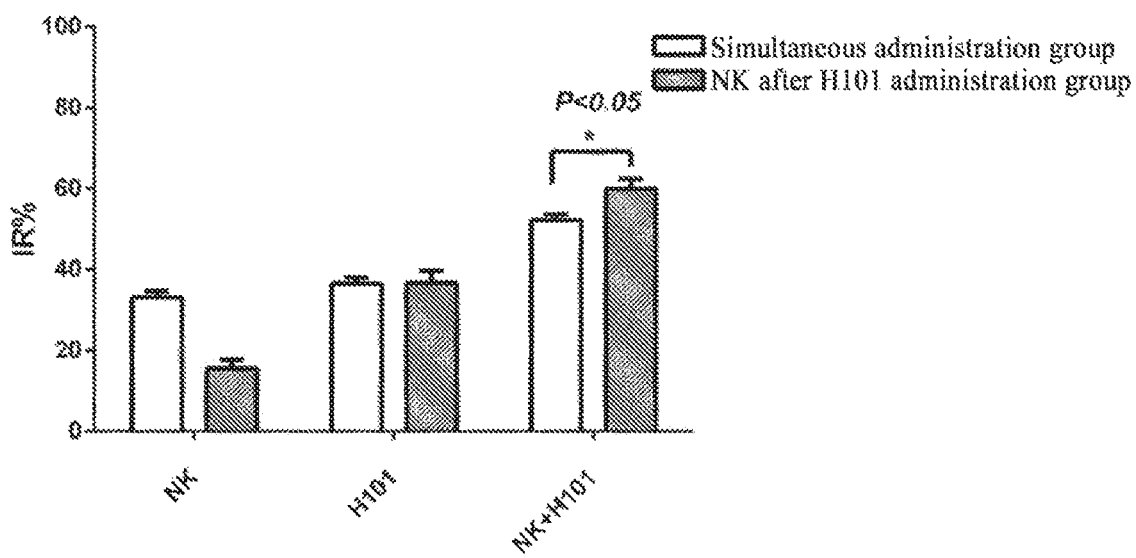
FIG. 20 shows a comparison between the result of the combined killing experiment of H101 and NK cells in Example C3 and the result of the simultaneous combined administration of H101 and NK cells in Comparative example C5 according to the present disclosure.

As shown in FIG. 19 (wherein X axis represents the different groups, and Y axis represents the corresponding percentage values of inhibition rates), the inhibition rate of the single application of H101 was about 36% and the inhibition rate of single application of the NK cells was about 33%. Compared to these single applications, the inhibition rate of combined use of NK cells and H101 was increased, which was about 52%; however, no significant synergistic effect was shown as compared to Example C3 (see the comparison shown in FIG. 20, wherein X axis represents the different groups, and Y axis represents the corresponding percentage values of inhibition rates).

Comparative Example C6: Simultaneous Combined Administration of the Drugs

Figure 24:
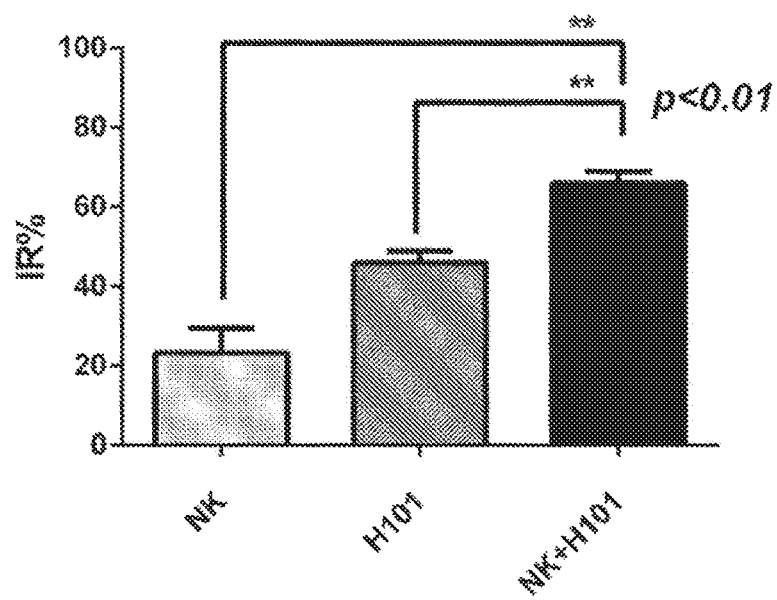
FIG. 24 shows the result of the simultaneous combined administration of H101 and NK cells in Comparative example C6 according to the present disclosure.
Figure 25:
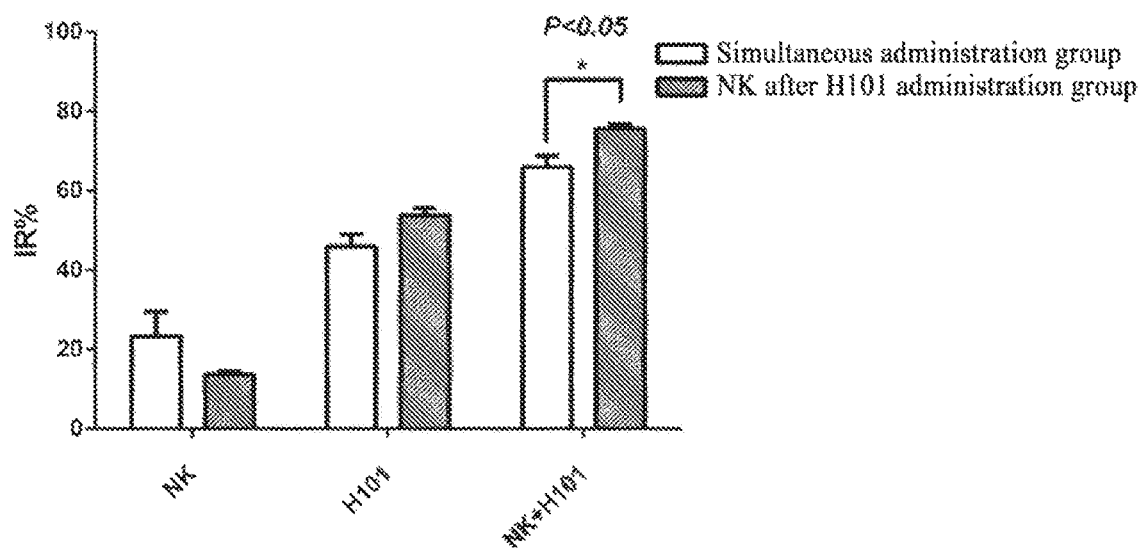
FIG. 25 shows a comparison between the result of the combined killing experiment of H101 and NK cells in Example C4 and the result of the simultaneous combined administration of H101 and NK cells in Comparative example C6 according to the present disclosure.

Comparative example C6 was similar to the above Comparative example C5 except that, after adding H101 and NK, the cells were incubated to 96 hours instead of 72 hours. As shown in FIG. 24 (wherein X axis represents the different groups, and Y axis represents the corresponding percentage values of inhibition rates), the inhibition rate of the single application of H101 was about 46% and the inhibition rate of single application of the NK cells was about 23%. Compared to these single applications, the inhibition rate of combined use of NK cells and H101 was increased, which was about 66%; however, no significant synergistic effect was shown as compared to FIG. 23 (see the comparison shown in FIG. 25, wherein X axis represents the different groups, and Y axis represents the corresponding percentage values of inhibition rates).

The above results indicate that 1) the combined application of H101 and NK cells has superior efficacy than the single application of either H101 or NK cells; and 2) the timing of administration can significantly affect the efficacy of the combined application of H101 and NK cells—when H101 and NK cells were substantially administered simultaneously, the combined application did not show a synergistic effect; whereas when NK cells were administered about 24 to 48 hours after the administration of H101, the combined application showed a significant synergistic effect.

Comparative Example C7: Comparison Between Different Administration Sequences in Combined Application HT29 cells were plated into culture plates at 30% confluency and incubated in DMEM+10% FBS at 37° C. In 5% $CO_2$ for 24 hours. Then, the medium was replaced with fresh DMEM+10% FBS, and NK cells were added (E:T ratio (NK:HT29)=3:1). The cells were incubated at 37° C. in 5% $CO_2$ for 24 hours. Then, H101 (MOI=13.6) was added without replacing the medium, and the cells were further incubated for 48 hours. Dead cells and debris were washed off, and Trypan Blue Staining method was used for counting the remaining living HT29 cells. In the experiment, there were also a blank control group, in which none of the virus or NK cells were added to HT29 cells; a H101 group, in which H101 was added at its corresponding time point but no NK cells were added; and a NK group, in which the NK cells were added at their corresponding time point but no H101 was added. All the control groups underwent the corresponding medium replacement operations at corresponding times. All the experiments were repeated for over 3 times, and the averages were used for statistical analysis.

Figure 21:
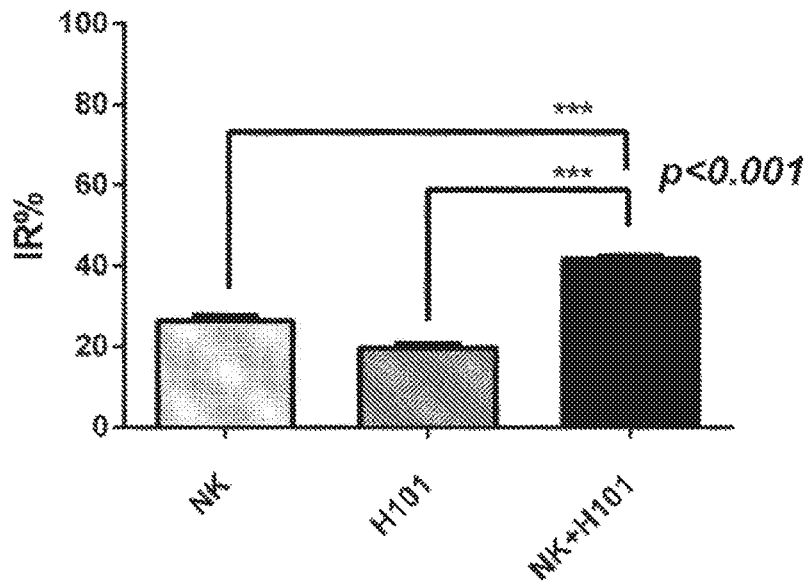
FIG. 21 shows the result of the combined administration of H101 and NK cells at an interval of 24 hours in a reverse sequential manner in Comparative example C7 according to the present disclosure.

As shown in FIG. 21 (wherein X axis represents the different groups, and Y axis represents the corresponding percentage values of inhibition rates), the inhibition rate of the combined application in a reverse sequential manner (NK cells being administered first and H101 later) was about 42%, the inhibition rate of the single application of H101 was about 20%, and the inhibition rate of single application of the NK cells was about 26%. The combined application in the reverse sequential manner did not show a synergistic effect.

Figure 26:
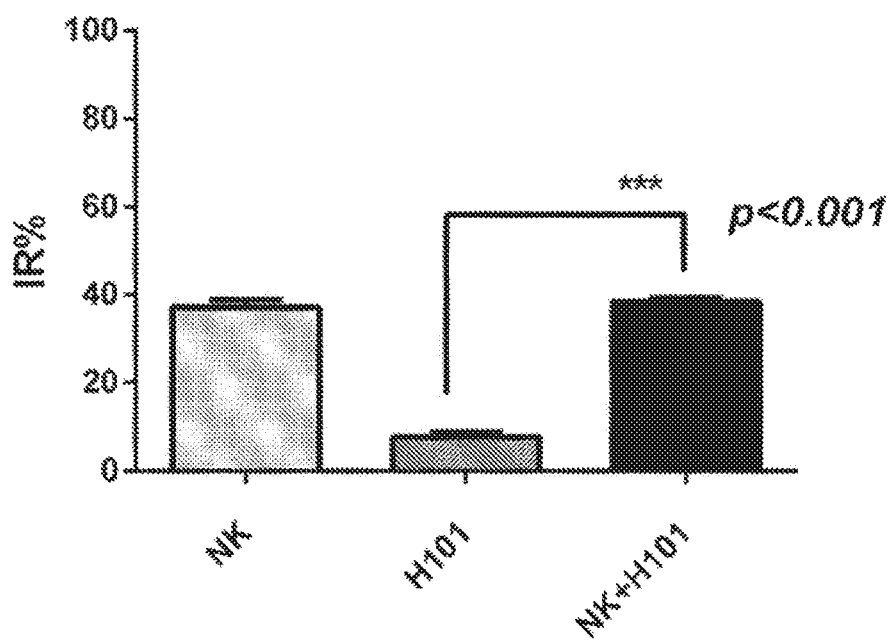
FIG. 26 shows the result of the combined administration of H101 and NK cells at an interval of 48 hours in a reverse sequential manner in Comparative example C8 according to the present disclosure.

Comparative Example C8: Comparison Between Different Administration Sequences in Combined Application Comparative example C8 was similar to the above Comparative example C7 except that, after adding NK, the cells were incubated to 48 hours instead of 24 hours, and then H101 was added. As shown in FIG. 26 (wherein X axis represents the different groups, and Y axis represents the corresponding percentage values of inhibition rates), the inhibition rate of the combined application in a reverse sequential manner (NK cells being administered first and H101 later) was about 38%, the inhibition rate of the single application of H101 was about 8%, and the inhibition rate of single application of the NK cells was about 37%. The combined application in the reverse sequential manner did not show a synergistic effect.

Example C9: Dose Escalation Study of Combined Administrations

HT29 cells were plated into culture plates at 30% confluency and incubated in DMEM+10% FBS at 37° C. in 5% $CO_2$ for 24 hours. In the first group, the medium was replaced with serum-free DMEM, then H101 (MOI=13.6) was added, and the infection process lasted for 6 hours. Then, the medium was replaced with fresh DMEM+10% FBS. After the cells were incubated for 24 hours, NK cells at various dose levels (E:T=1:1, 2:1, 3:1, 4:1, or 5:1) were added respectively, and the cells were further incubated for 48 hours. Dead cells and debris were washed off, and Trypan Blue Staining method was used for counting the remaining living HT29 cells. In the second group, the medium was replaced with serum-free DMEM, and H101 (MOI=13.6) was added. After a six-hour infection, the medium was replaced with fresh DMEM+10% FBS, and NK cells at various dose levels (E:T=1:1, 2:1, 3:1, 4:1, or 5:1) were added respectively. The cells were further incubated to 72 hours, then dead cells and debris were washed off, and the remaining living HT29 cells were counted using Trypan Blue Staining method. In the third group, after the medium was replaced with fresh DMEM+10% FBS, NK cells at various dose levels (E:T=1:1, 2:1, 3:1, 4:1, or 5:1) were first added respectively, and the cells were incubated for 24 hours. Then, the same dose of H101 (MOI=13.6) was added without replacing the medium, and the cells were further incubated for 48 hours. Dead cells and debris were washed off, and Trypan Blue Staining method was used for counting the remaining living HT29 cells. In the experiment, there was also a blank control group, in which none of the virus or NK cells were added to HT29 cells. The control groups underwent the corresponding medium replacement operations at the corresponding times. All the experiments were repeated for over 3 times, and the averages were used for statistical analysis.

Figure 22:
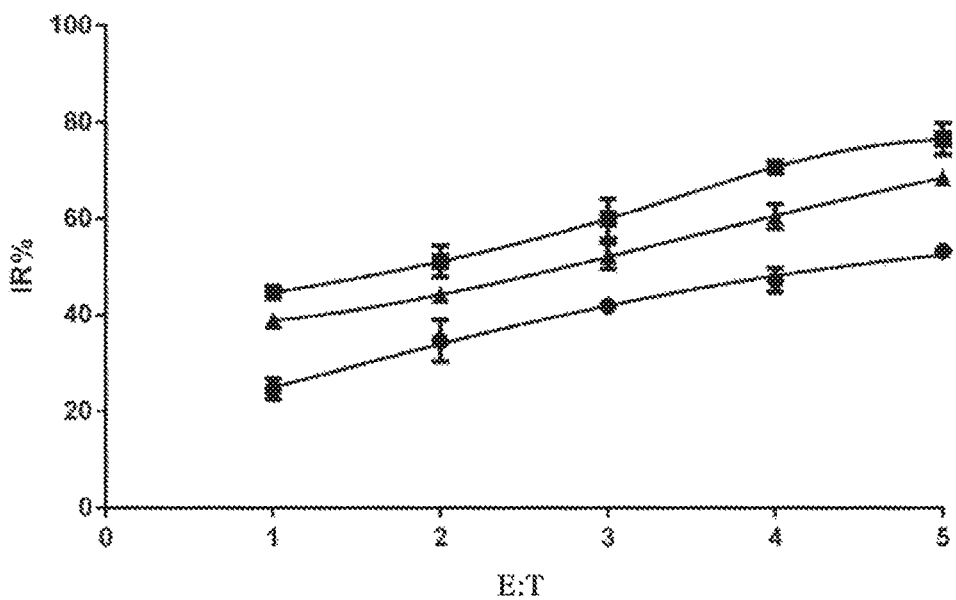
FIG. 22 shows the results of a dose escalation study of combined administrations in Example C9 according to the present disclosure. The curve connecting the squares represents the killing effect against HT29 cells when H101 was given first and NK cells were given later; the curve connecting the triangles represents the killing effect against HT29 cells when H101 and NK cells were given simultaneously; and the curve connecting the circles represents the killing effect against HT29 cells when NK cells were given first and H101 was given later.

As shown in FIG. 22 (wherein X axis represents E:T ratios, and Y axis represents the corresponding percentage values of inhibition rates), in the combined application, there was a positive correlation between the dose level of NK cells and its killing effect, and when the dose levels of H101 and NK cells were unchanged respectively, the killing effect of the combination that H101 was administered first and NK cells later was significantly greater than the killing effect of the combination that H101 and NK cells were administered simultaneously or the killing effect of the combination that NK cells were administered first and H101 later.

Example C10: Dose Escalation Study of Combined Administrations

Figure 27:
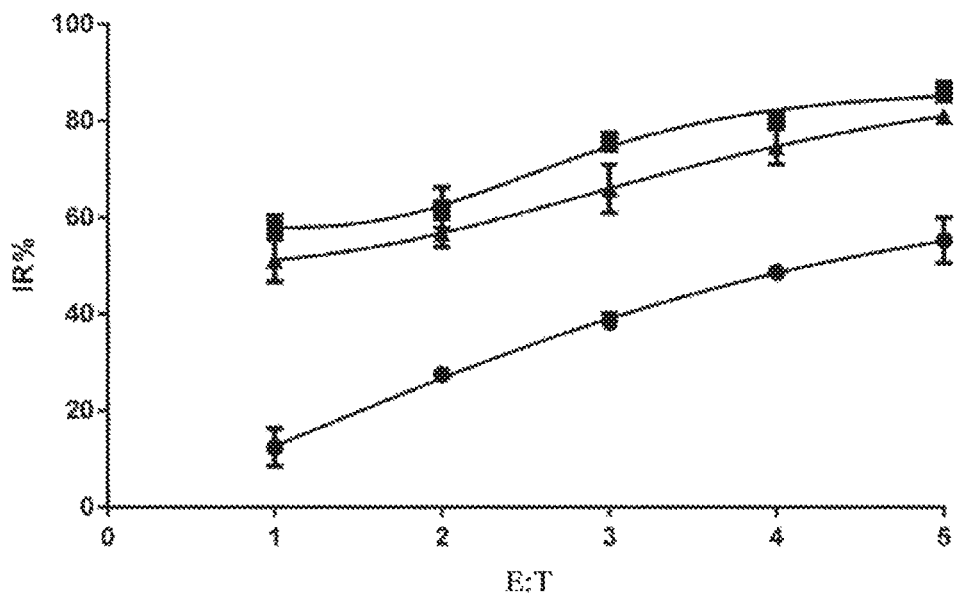
FIG. 27 shows the results of a dose escalation study of combined administrations in Example C10 according to the present disclosure. The curve connecting the squares represents the killing effect against HT29 cells when H101 was given first and NK cells were given later; the curve connecting the triangles represents the killing effect against HT29 cells when H101 and NK cells were given simultaneously; and the curve connecting the circles represents the killing effect against HT29 cells when NK cells were given first and H101 was given later.

Example C10 was similar to the above Example C9 except that, in the experimental group (oncolytic virus being administered first and NK cells later), after adding H101 the cells were incubated to 48 hours instead of 24 hours, and then NK cells were added; in the simultaneous combined administration group, after simultaneously adding H101 and NK, the cells were incubated to 96 hours instead of 72 hours; in the combined administration group in a reverse sequential manner, after adding NK the cells were incubated to 48 hours instead of 24 hours, and then H101 was added. As shown in FIG. 27 (wherein X axis represents E:T ratios, and Y axis represents the corresponding percentage values of inhibition rates), in the combined application, there was a positive correlation between the dose level of NK cells and its killing effect, and when the dose levels of H101 and NK cells were unchanged respectively, the killing effect of the combination that H101 was administered first and NK cells later was significantly greater than the killing effect of the combination that H101 and NK cells were administered simultaneously or the killing effect of the combination that NK cells were administered first and H101 later.

Experimental Example C11: Detection of NKG2D Ligands on Cell Surface after Infection of HT29 Cells by H101

HT29 cells were plated into culture plates at 50% confluency and incubated in DMEM+10% FBS at 37° C. in 5% $CO_2$ for 24 hours. Then, H101 (MOI=17) was added without replacing the medium. The infection process lasted for 24 hours with the cell being incubated at 37° C. in 5% $CO_2$. In the experiment, there was also a blank control group, in which no virus was added to HT29 cells. The cells were collected by trypsinization, washed once with PBS, and then NKG2D-associated ligands (ULBP-1, ULBP-4, ULBP-2/5/6, and MICA/MICB) on HT29 cells were detected. The changes of NKG2D-associated ligands on the surface of HT29 cells infected by H101 were calculated relative to the control group in which no H101 was added. The following antibodies were used: Anti-Human ULBP-1 PE (R&D; Item No. FAB1380P), Anti-Human ULBP-4/RAETIE APC (R&D; Item No. FAB6285A), Anti-Human ULBP-2/5/6 APC (R&D; Item No. FAB1298A), and Anti-Human MICA/MICB FITC (Miltenyi; Item No. 130-106-100). The resultant HT29 cell pellets were resuspended in 50 μl of 1% FBS+PBS, respectively. Corresponding antibodies (1-2 μl) were added to the respective samples and mixed homogeneously. After incubated at 4° C. for 30 minutes, the resultant samples were washed once with 1% FBS+PBS. The resultant HT29 cell pellets were resuspended in 300 μl of 1% FBS+PBS, mixed homogeneously, and then detected by a flow cytometer.

Figure 28:
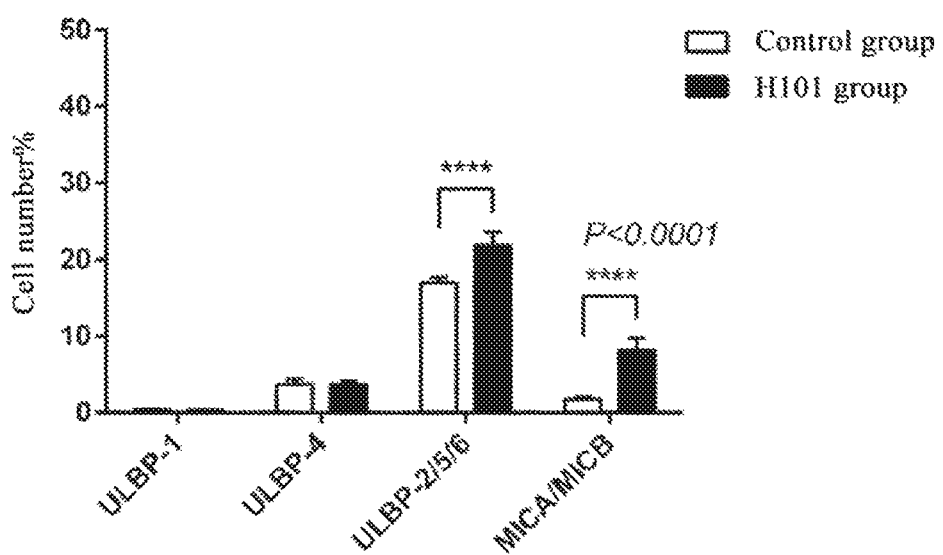
FIG. 28 shows the result of changes in NKG2D ligands on the surface of HT29 cells after the cells were infected with H101 and cultured to 24 hours in Experimental example C11 according to the present disclosure.

As shown in FIG. 28 (wherein X axis represents the different NKG2D ligand detection groups, and Y axis represents the corresponding percentage values of cell numbers), after HT29 cells were infected by H101 and cultured to 24 hours, there was no significant change in ULBP-1 and ULBP-4; whereas the expressions of ULBP-2/5/6 and MICA/MICB were significantly increased.

Experimental Example C12: Detection of NKG2D Ligands on Cell Surface after Infection of HT29 Cells by H101

Figure 29:
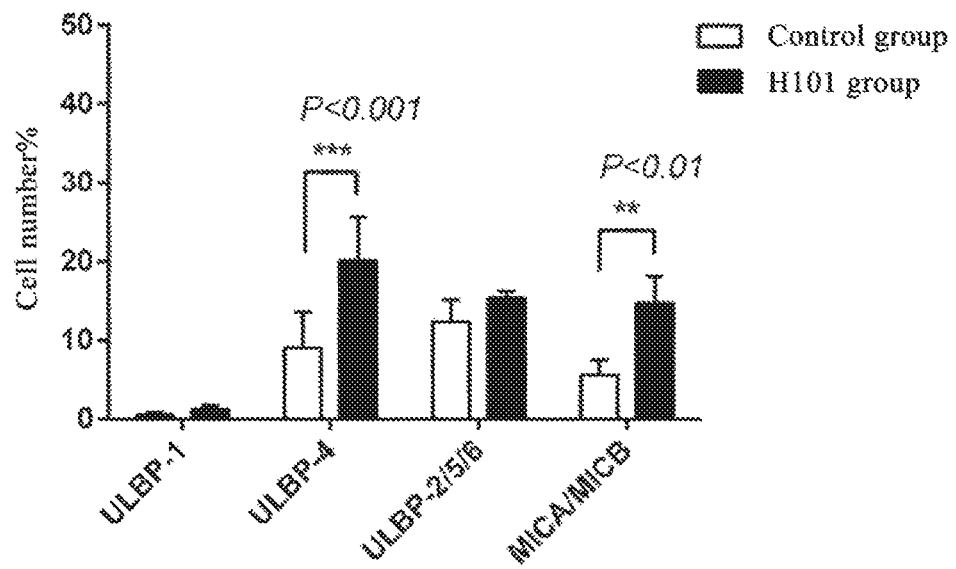
FIG. 29 shows the result of changes in NKG2D ligands on the surface of HT29 cells after the cells were infected with H101 and cultured to 48 hours in Experimental example C12 according to the present disclosure.

Experimental example C12 was similar to the above Experimental example C11, except that the detection was performed after the infection of HT29 cells by H101 lasted for 48 hours instead of 24 hours. As shown in FIG. 29 (wherein X axis represents the different NKG2D ligand detection groups, and Y axis represents the corresponding percentage values of cell numbers), after HT29 cells were infected by H101 for 48 hours, there was no significant change in ULBP-1 and ULBP-2/5/6; whereas the expressions of ULBP-4 and MICA/MICB were significantly increased.

The above results indicate 1) after HT29 cells are infected by H101, some ligands of NKG2D on the cell surface are significantly increased; 2) the increase of NKG2D ligands on the surface of HT29 cells promotes the recognition and killing effect of NK cells against HT29 cells; and 3) the combined treatment regimen of H101 and NK has the best efficacy when the oncolytic virus is administered first and NK cells later.

Figure 30:
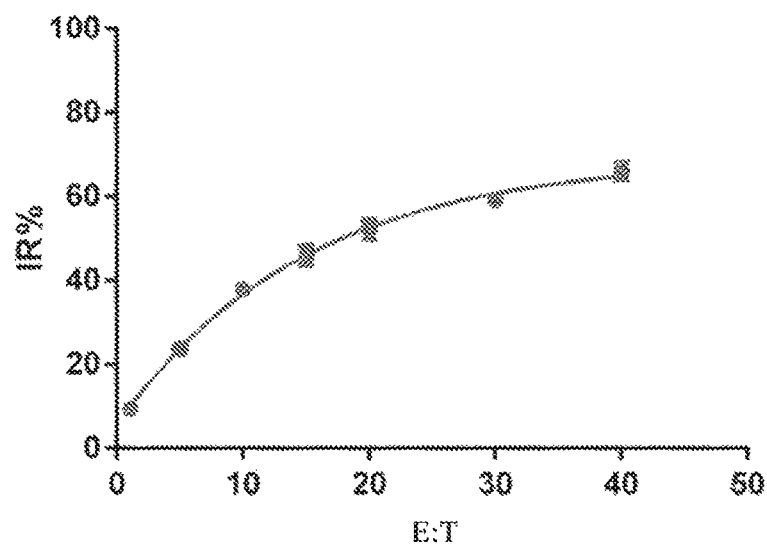
FIG. 30 shows the result of a dose-response experiment of NK cells against A549 cells in Experimental example D1 according to the present disclosure.

D: Study on the Killing Effect of Combined Application of Oncolytic Vaccinia Virus and NK Cells Against A549 Cells Experimental Example D1: Dose-Response Experiment of NK Cells Against A549 Cells A549 cells were plated into culture plates at 30% confluency and incubated in DMEM:F12 (1:1)+10% FBS at 37° C. in 5% $CO_2$ for 48 hours. Then, the medium was replaced with fresh DMEM:F12 (1:1)+10% FBS, and NK cells were added with the effector to target cell ratios (i.e., E:T, ratio of cell numbers) as follows: NK:A549=40:1, 30:1, 20:1, 15:1, 10:1, 5:1, and 1:1, respectively. The killing process at each E:T ratio lasted for 48 hours with the cells being incubated at 37° C. in 5% $CO_2$. Afterwards, Trypan Blue Staining method was used for counting the living A549 cells, and the killing rates of A549 cells by NK cells were calculated relative to the control group in which no NK cells were added. The X axis of the dose-response curve represents E:T ratio, and Y axis represents the percentage value of inhibition rate (IR). The result of the experiment with killing time being 48 hours is shown in FIG. 30, which exhibits an inhibition rate of about 24% when E:T ratio is 5:1, indicating a suitable dose level. This dosage was adopted as the dose level of NK cells to be used in the combined killing experiment.

Figure 31:
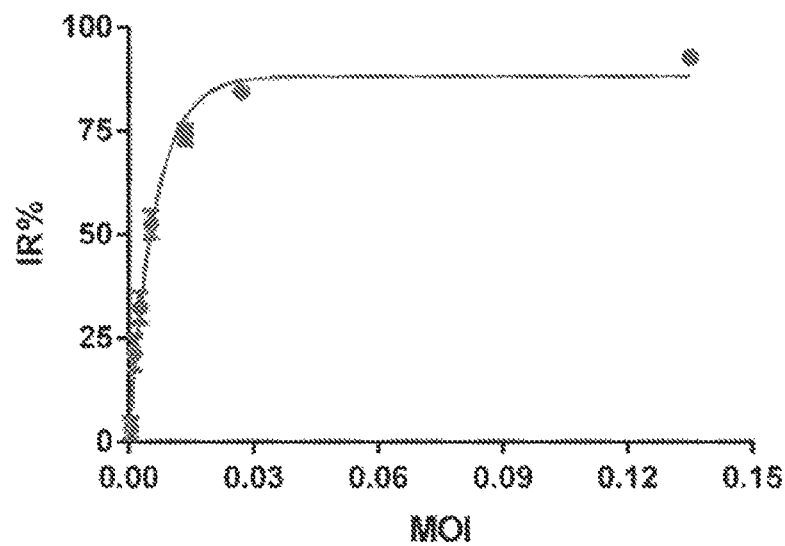
FIG. 31 shows the result of a dose-response experiment of ddvv-RFP against A549 cells in Experimental example D2 according to the present disclosure.

Experimental Example D2: Dose-Response Experiment of ddvv-RFP Against A549 Cells A549 cells were plated into culture plates at 30% confluency and incubated in DMEM:F12 (1:1)+10% FBS at 37° C. in 5% $CO_2$ for 24 hours. Then, the medium was replaced with fresh serum-free DMEM:F12 (1:1), and ddvv-RFP was added with MOI being 0.135, 0.027, 0.0135, 0.0054, 0.0027, 0.00135, and 0.00054, respectively. The time point at which ddvv-RFP was added was taken as 0 hour (the same below). The infection process lasted for 6 hours with the cells being incubated at 37° C. in 5% $CO_2$, then the medium was removed, and the cells were washed with PBS. Then, fresh DMEM:F12 (1:1)+10% FBS was added, and the cells were further incubated to 72 hours. Afterwards, Trypan Blue Staining method was used for counting the living A549 cells, and the killing rates of A549 cells by ddvv-RFP were calculated relative to the control group in which no ddvv-RFP was added. FIG. 31 shows the dose-response curve (wherein X axis represents MOI, and Y axis represents the percentage value of inhibition rate (IR)), which exhibits an inhibition rate of about 32% when MOI is 0.0027. This dosage was adopted as the dose level of ddvv-RFP to be used in the combined killing experiment.

Example D3: Combined Killing Experiment of ddvv-RFP and NK

It can be concluded from the above Experimental examples that the suitable dose level for the killing of ddvv-RFP against A549 cells was the MOI being about 0.0027; and the suitable dose level for the killing of NK cells against A549 cells was the E:T ratio (i.e., NK:A549) being about 5:1.

A549 cells were plated into culture plates at 30% confluency and incubated in DMEM:F12 (1:1)+10% FBS at 37° C. in 5% $CO_2$ for 24 hours. Then, the medium was replaced with serum-free DMEM:F12 (1:1), and ddvv-RFP (MOI=0.0027) was added. After a six-hour infection, the medium was replaced with DMEM:F12 (1:1)+10% FBS, and the cells were incubated at 37° C. in 5% $CO_2$ to 48 hours. Then, NK cells were added (E:T ratio (NK:A549)=5:1) without replacing the medium, and the cells were further incubated for 48 hours. Dead cells and debris were washed off, and Trypan Blue Staining method was used for counting the remaining living A549 cells. In the experiment, there were also a blank control group, in which none of the virus or NK cells were added to A549 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 32:
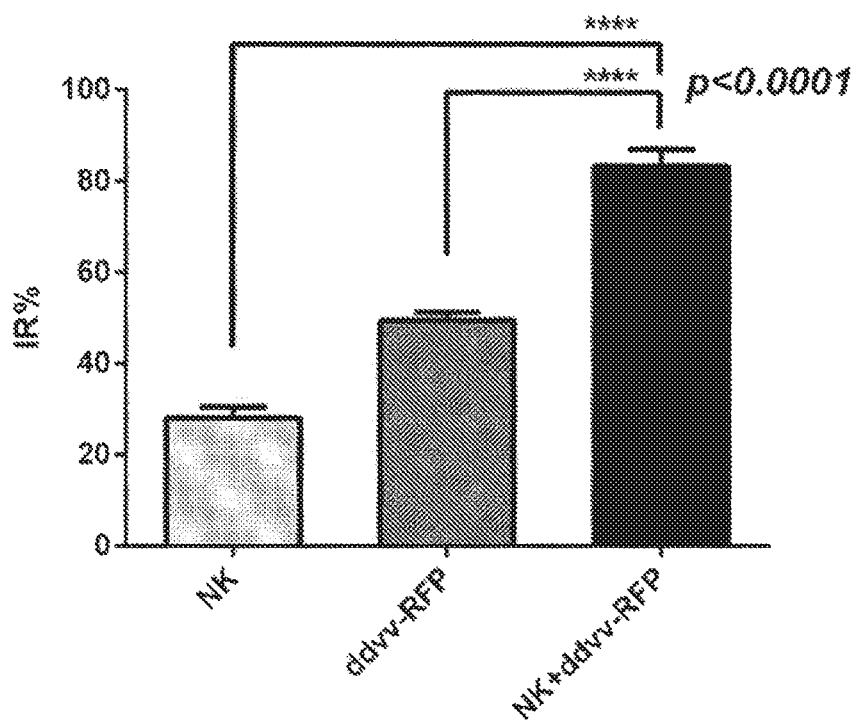
FIG. 32 shows the result of the combined killing experiment of ddvv-RFP and NK cells in Example D3 according to the present disclosure.

As shown in FIG. 32 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against A549 cells, and the synergistic inhibition rate was about 83%. However, in this experiment, the inhibition rate of single application of ddvv-RFP was about 49% and the inhibition rate of single application of the NK cells was about 28%.

Comparative Example D4: Simultaneous Combined Administration of the Drugs

A549 cells were plated into culture plates at 30% confluency and incubated in DMEM:F12 (1:1)+10% FBS at 37° C. in 5% $CO_2$ for 24 hours. Then, the medium was replaced with serum-free DMEM:F12 (1:1), and ddvv-RFP was added (MOI=0.0027). After a six-hour infection, the medium was replaced with fresh DMEM:F12 (1:1)+10% FBS, and NK cells were added (E:T ratio (NK:A549)=5:1). The cells were further incubated to 96 hours, then dead cells and debris were washed off, and the remaining living A549 cells were counted using Trypan Blue Staining method. In the experiment, there were also a blank control group, in which none of the virus or NK cells were added to A549 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 33:
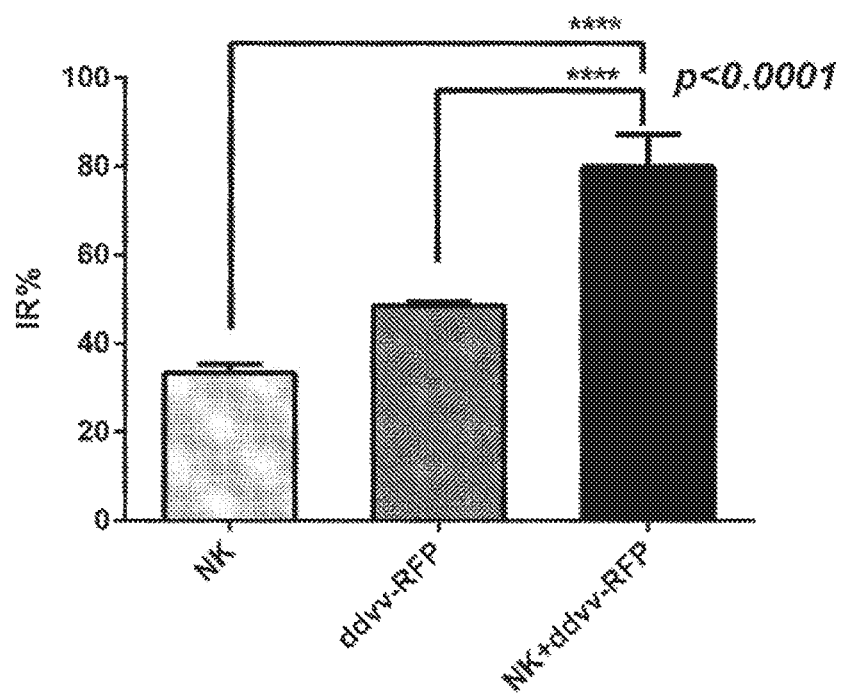
FIG. 33 shows the result of the simultaneous combined administration of ddvv-RFP and NK cells in Comparative example D4 according to the present disclosure.

As shown in FIG. 33 (wherein X axis represents the different groups, and Y axis represents the corresponding percentage values of inhibition rates), the inhibition rate of the single application of ddvv-RFP was about 49% and the inhibition rate of single application of the NK cells was about 33%. Compared to these single applications, the inhibition rate of combined use of NK cells and ddvv-RFP was increased, which was about 80%; however, no significant synergistic effect was shown.

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells—when ddvv-RFP and NK cells were substantially administered simultaneously, the combined application did not show a synergistic effect; whereas when ddvv-RFP was administered first and NK cells later, the combined application showed a significant synergistic effect.

Comparative Example D5: Comparison Between Different Administration Sequences in Combined Application A549 cells were plated into culture plates at 30% confluency and incubated in DMEM:F12 (1:1)+10% FBS at 37° C. In 5% $CO_2$ for 24 hours. Then, NK cells were added (E:T ratio (NK:A549=5:1) without replacing the medium, and the cells were incubated at 37° C. in 5% $CO_2$ for 48 hours. Then, ddvv-RFP (MOI=0.0027) was added without replacing the medium, and the cells were further incubated for 48 hours. Dead cells and debris were washed off, and Trypan Blue Staining method was used for counting the remaining living A549 cells. In the experiment, there were also a blank control group, in which none of the virus or NK cells were added to A549 cells; a ddvv-RFP group, in which ddvv-RFP was added at its corresponding time point but no NK cells were added; and a NK group, in which the NK cells were added at their corresponding time point but no ddvv-RFP was added. All the experiments were repeated for over 3 times, and the averages were used for statistical analysis.

Figure 34:
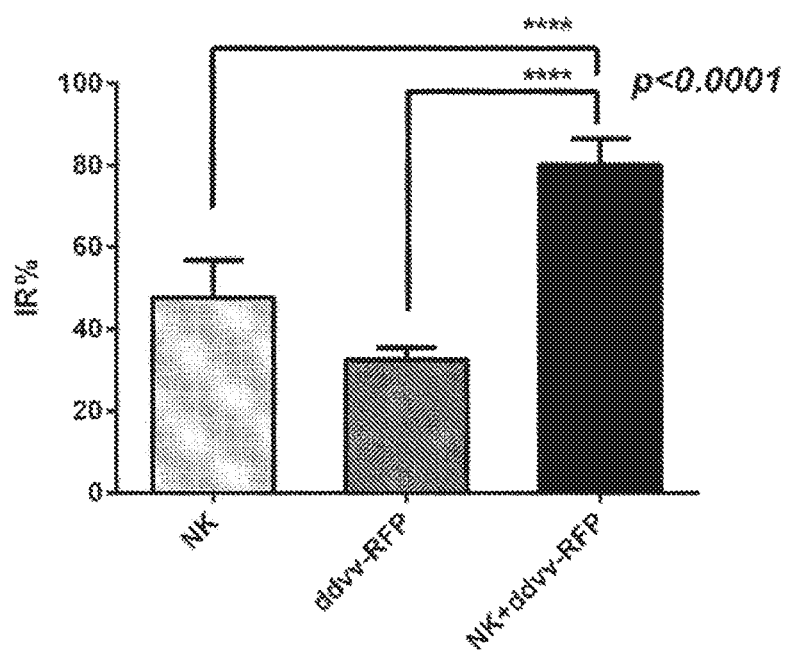
FIG. 34 shows the result of the combined administration of ddvv-RFP and NK cells in a reverse sequential manner in Comparative example D5 according to the present disclosure.

As shown in FIG. 34 (wherein X axis represents the different groups, and Y axis represents the corresponding percentage values of inhibition rates), the inhibition rate of the combined application in a reverse sequential manner (NK cells being administered first and ddvv-RFP later) was about 80%, the inhibition rate of the single application of ddvv-RFP was about 33%, and the inhibition rate of single application of the NK cells was about 48%. The combined application in the reverse sequential manner did not show a synergistic effect.

Figure 35:
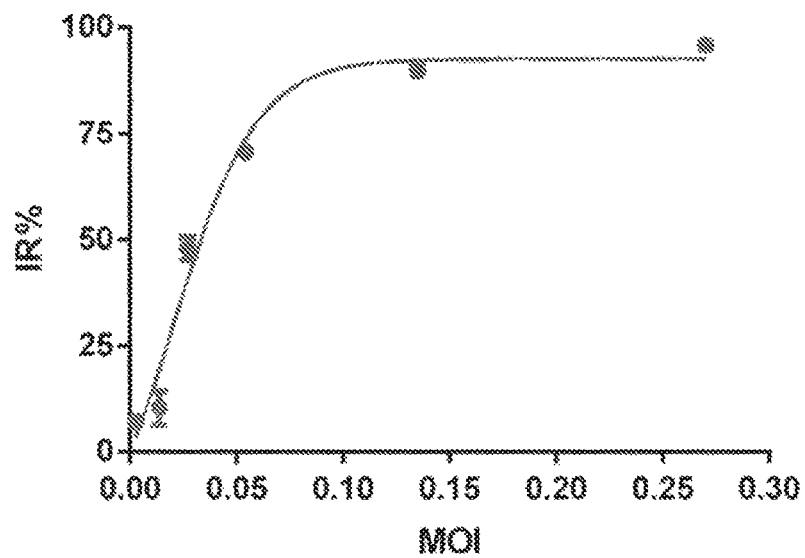
FIG. 35 shows the result of a dose-response experiment of ddvv-RFP against HepG2 cells in Experimental example E1 according to the present disclosure.

E: Study on the Killing Effect of Combined Application of Oncolytic Vaccinia Virus and NK Cells Against HepG2 Cells Experimental Example E1: Dose-Response Experiment of ddvv-RFP Against HepG2 Cells HepG2 cells were plated into culture plates at 30% confluency and incubated in DMEM+10% FBS at 37° C. In 5% $CO_2$ for 24 hours. Then, the medium was replaced with fresh serum-free DMEM, and ddvv-RFP was added with MOI being MOI=0.27, 0.135, 0.054, 0.027, 0.0135, and 0.0027, respectively. The infection process lasted for 6 hours with the cells being incubated at 37° C. in 5% $CO_2$, then the medium was removed, and the cells were washed with PBS. Then, fresh DMEM+10% FBS was added, and the cells were further incubated to 72 hours. Afterwards, Trypan Blue Staining method was used for counting the living HepG2 cells, and the killing rates of HepG2 by ddvv-RFP were calculated relative to the control group in which no ddvv-RFP was added. FIG. 35 shows the dose-response curve (wherein X axis represents MOI, and Y axis represents the percentage value of inhibition rate (IR)), which exhibits an inhibition rate of about 42% when the dose level of ddvv-RFP against HepG2 cells is the MOI being about 0.027, and an inhibition rate of about 19% when the dose level is the MOI being about 0.0135. In the subsequent combined killing experiment, it was suitable to adopt MOI=0.027 as the dose level of ddvv-RFP to be used when the interval between the administrations of ddvv-RFP and NK cells was 24 hours, while it was suitable to adopt MOI=0.0135 as the dose level of ddvv-RFP to be used when the said interval was 48 hours.

Example E2: Combined Killing Experiment of ddvv-RFP and NK

It can be concluded from the above Experimental examples that the suitable dose level for the killing of ddvv-RFP against HepG2 cells was the MOI being about 0.027; and the suitable dose level for the killing of NK cells against HepG2 cells was the E:T ratio (i.e., NK:HepG2) being about 3:1.

HepG2 cells were plated into culture plates at 30% confluency and incubated in DMEM+10% FBS at 37° C. In 5% $CO_2$ for 24 hours. Then, the medium was replaced with serum-free DMEM, and ddvv-RFP was added (MOI=0.027). After a six-hour infection, the medium was replaced with DMEM+10% FBS, and the cells were incubated at 37° C. in 5% CO2 to 24 hours. Then, NK cells were added (E:T ratio (NK:HepG2=3:1) without replacing the medium, and the cells were further incubated for 48 hours. Dead cells and debris were washed off, and Trypan Blue Staining method was used for counting the remaining living HepG2 cells. In the experiment, there were also a blank control group, in which none of the virus or NK cells were added to HepG2 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 36:
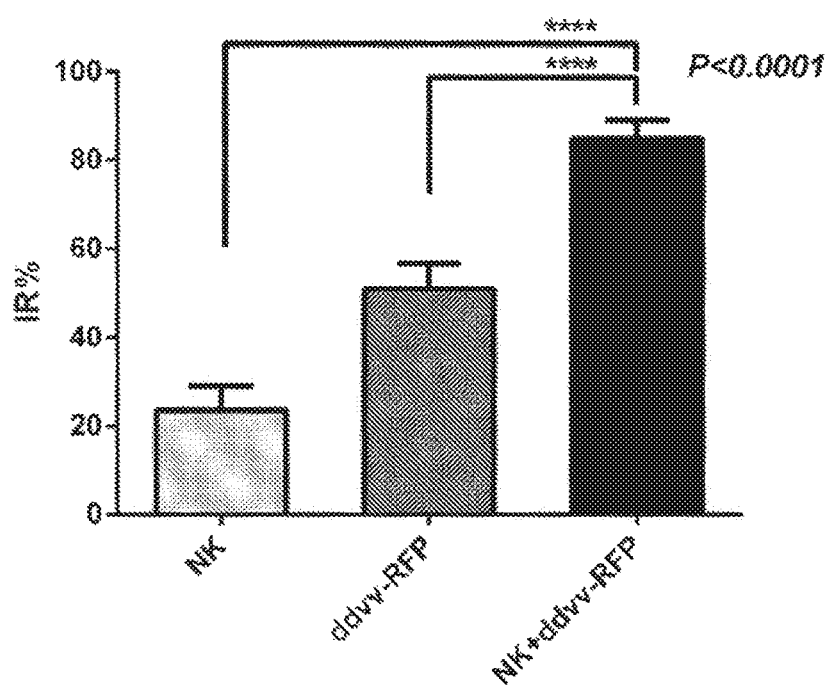
FIG. 36 shows the result of the combined killing experiment of ddvv-RFP and NK cells administered at an interval of 24 hours in Example E2 according to the present disclosure.

As shown in FIG. 36 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against HepG2 cells, and the synergistic inhibition rate was about 85%. However, in this experiment, the inhibition rate of single application of ddvv-RFP was about 51% and the inhibition rate of single application of the NK cells was about 23%.

Example E3: Combined Killing Experiment of ddvv-RFP and NK

Figure 39:
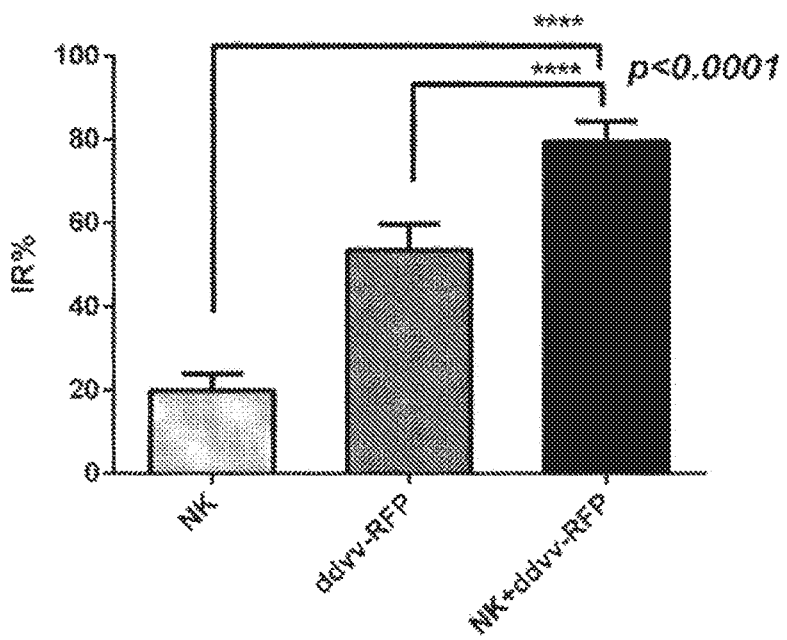
FIG. 39 shows the result of the combined killing experiment of ddvv-RFP and NK cells administered at an interval of 48 hours in Example E3 according to the present disclosure.

Example E3 was similar to the above Example E2 except that ddvv-RFP was added at a dose level of MOI=0.0135, and the infected cells were incubated to 48 hours instead of 24 hours before adding NK cells. As shown in FIG. 39 (wherein X axis represents the different groups, and Y axis represents the corresponding percentage values of inhibition rates), the final result also demonstrated that the combined application of ddvv-RFP and NK cells (the oncolytic virus being administered first and the NK cells later) had significant synergistic killing effect against HepG2 cells, and the synergistic inhibition rate was about 79%. However, in this experiment, the inhibition rate of single application of ddvv-RFP was about 53% and the inhibition rate of single application of the NK cells was about 20%.

Comparative Example E4: Simultaneous Combined Administration of the Drugs

HepG2 cells were plated into culture plates at 30% confluency and incubated in DMEM+10% FBS at 37° C. in 5% $CO_2$ for 24 hours. Then, the medium was replaced with serum-free DMEM, and ddvv-RFP was added (MOI=0.027). After a six-hour infection, the medium was replaced with fresh DMEM+10% FBS, and NK cells were added (E:T ratio (NK:HepG2)=3:1). The cells were further incubated to 72 hours, then dead cells and debris were washed off, and the remaining living HepG2 cells were counted using Trypan Blue Staining method. In the experiment, there were also a blank control group, in which none of the virus or NK cells were added to HepG2 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 37:
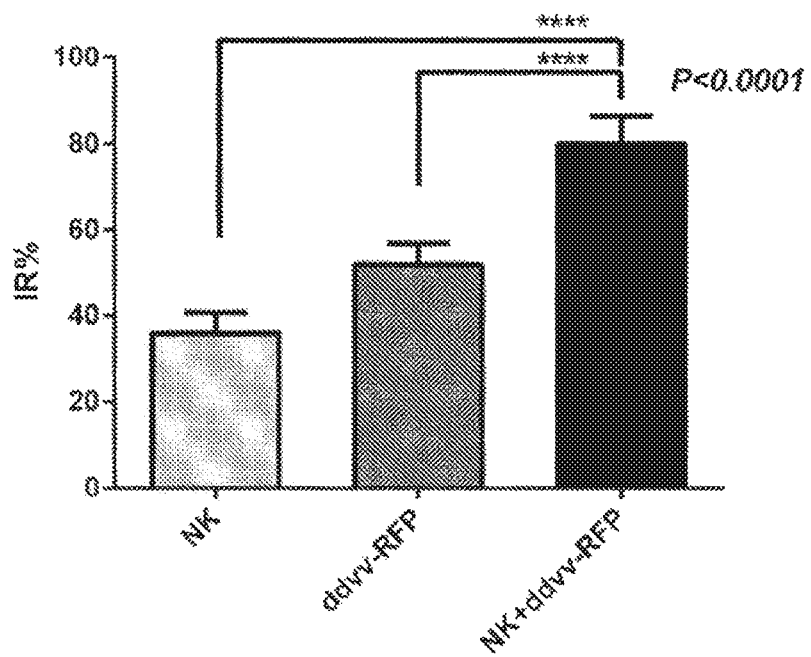
FIG. 37 shows the result of the simultaneous combined administration of ddvv-RFP and NK cells in Comparative example E4 according to the present disclosure.

As shown in FIG. 37 (wherein X axis represents the different groups, and Y axis represents the corresponding percentage values of inhibition rates), the inhibition rate of the single application of ddvv-RFP was about 52% and the inhibition rate of single application of the NK cells was about 36%. Compared to these single applications, the inhibition rate of combined use of NK cells and ddvv-RFP was increased, which was about 80%; however, no significant synergistic effect was shown.

Comparative Example E5: Simultaneous Combined Administration of the Drugs

Figure 40:
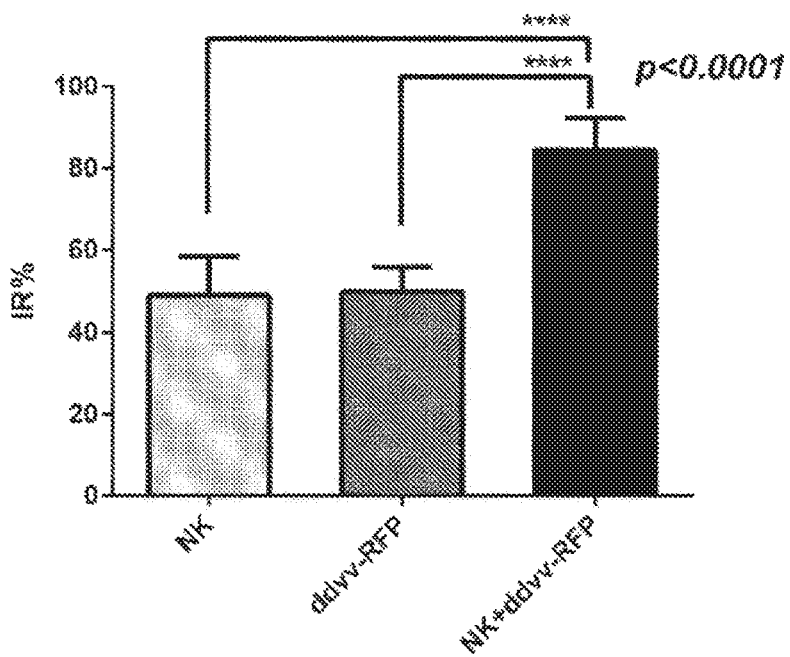
FIG. 40 shows the result of the simultaneous combined administration of ddvv-RFP and NK cells in Comparative example E5 according to the present disclosure.

Comparative example E5 was similar to the above Comparative example E4 except that ddvv-RFP was added at a dose level of MOI=0.0135, and the cells were incubated with both ddvv-RFP and NK cells to 96 hours instead of 72 hours. As shown in FIG. 40 (wherein X axis represents the different groups, and Y axis represents the corresponding percentage values of inhibition rates), the inhibition rate of the single application of ddvv-RFP was about 50% and the inhibition rate of single application of the NK cells was about 49%. Compared to these single applications, the inhibition rate of combined use of NK cells and ddvv-RFP was increased, which was about 84%; however, no significant synergistic effect was shown.

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells— when ddvv-RFP and NK cells were substantially administered simultaneously, the combined application did not show a synergistic effect; whereas when NK cells were administered about 24 to 48 hours after the administration of ddvv-RFP, the combined application showed a significant synergistic effect.

Comparative Example E6: Comparison Between Different Administration Sequences in Combined Application HepG2 cells were plated into culture plates at 30% confluency and incubated in DMEM+10% FBS at 37° C. in 5% CO$_2$ for 24 hours. Then, the medium was replaced with fresh DMEM+10% FBS, and NK cells were added (E:T ratio (NK:HepG2)=3:1). The cells were incubated at 37° C. in 5% CO$_2$ for 24 hours. Then, ddvv-RFP (MOI=0.0027) was added without replacing the medium, and the cells were further incubated for 48 hours. Dead cells and debris were washed off, and Trypan Blue Staining method was used for counting the remaining living HepG2 cells. In the experiment, there were also a blank control group, in which none of the virus or NK cells were added to HepG2 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 38:
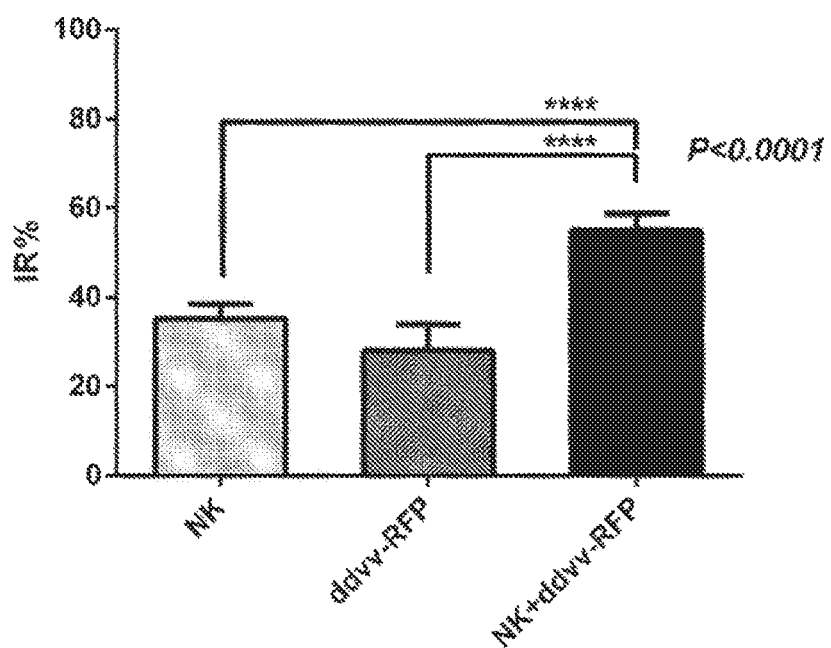
FIG. 38 shows the result of the combined administration of ddvv-RFP and NK cells at an interval of 24 hours in a reverse sequential manner in Comparative example E6 according to the present disclosure.

As shown in FIG. 38 (wherein X axis represents the different groups, and Y axis represents the corresponding percentage values of inhibition rates), the inhibition rate of the combined application in a reverse sequential manner (NK cells being administered first and ddvv-RFP later) was about 55%, the inhibition rate of the single application of ddvv-RFP was about 28%, and the inhibition rate of single application of the NK cells was about 35%. The combined application in the reverse sequential manner did not show a synergistic effect.

Figure 41:
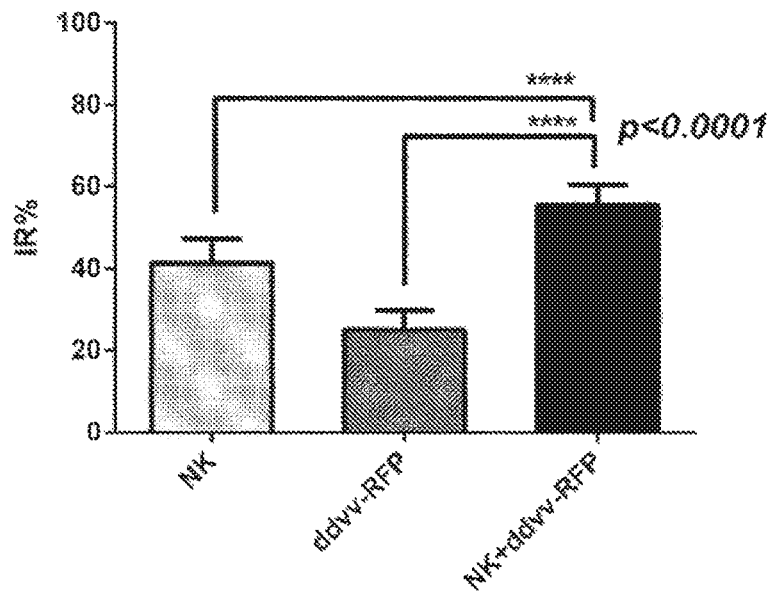
FIG. 41 shows the result of the combined administration of ddvv-RFP and NK cells at an interval of 48 hours in a reverse sequential manner in Comparative example E7 according to the present disclosure.

Comparative Example E7: Comparison Between Different Administration Sequences in Combined Application Comparative example E7 was similar to the above Comparative example E6 except that, after adding NK the cells were incubated to 48 hours instead of 24 hours, and then ddvv-RFP was added (MOI=0.0135). As shown in FIG. 41 (wherein X axis represents the different groups, and Y axis represents the corresponding percentage values of inhibition rates), the inhibition rate of the combined application in a reverse sequential manner (NK cells being administered first and ddvv-RFP later) was about 56%, the inhibition rate of the single application of ddvv-RFP was about 25%, and the inhibition rate of single application of the NK cells was about 41%. The combined application in the reverse sequential manner did not show a synergistic effect.

F: Study on the Killing Effect of Combined Application of Oncolytic Vaccinia Virus and NK Cells Against HT29 Cells

Experimental Example F1: Dose-Response Experiment of ddvv-RFP Against HT29

Figure 42:
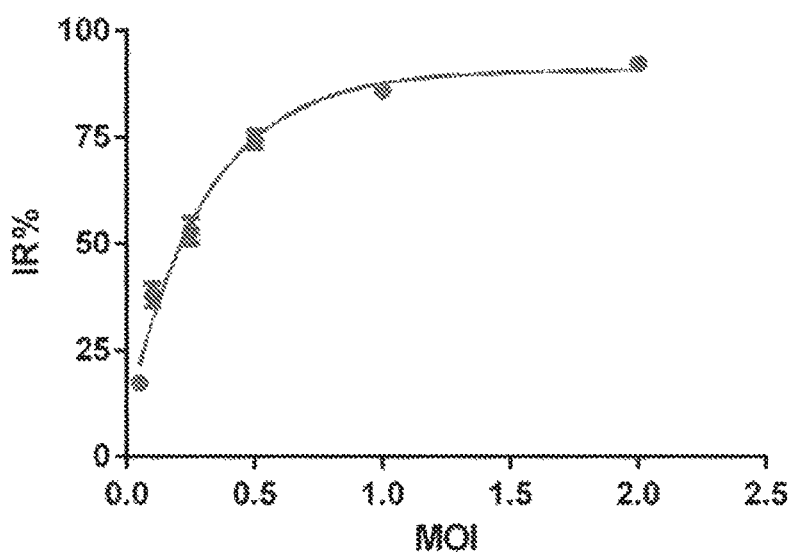
FIG. 42 shows the result of a dose-response experiment of ddvv-RFP against HT29 cells in Experimental example F1 according to the present disclosure.

HT29 cells were plated into culture plates at 30% confluency and incubated in DMEM+10% FBS at 37° C. in 5% CO$_2$ for 24 hours. Then, the medium was replaced with fresh serum-free DMEM, and ddvv-RFP was added with MOI being MOI=2, 1, 0.5, 0.25, 0.1, and 0.05, respectively. The infection process lasted for 6 hours with the cells being incubated at 37° C. in 5% CO$_2$, then the medium was removed, and the cells were washed with PBS. Then, fresh DMEM+10% FBS was added, and the cells were further incubated to 72 hours. Afterwards, Trypan Blue Staining method was used for counting the living HT29 cells, and the killing rates of HT29 cells by ddvv-RFP were calculated relative to the control group in which no ddvv-RFP was added. FIG. 42 shows the dose-response curve (wherein X axis represents MOI, and Y axis represents the percentage value of inhibition rate (IR)), which exhibits an inhibition rate of about 49% when the dose level of ddvv-RFP against HT29 cells is the MOI being about 0.2. This dosage, MOI=0.2, was adopted as the dose level of ddvv-RFP to be used in the combined killing experiment.

Example F2: Combined Killing Experiment of ddvv-RFP and NK

It can be concluded from the above Experimental examples that the suitable dose level for the killing of ddvv-RFP against HT29 cells was the MOI being about 0.2; and the suitable dose level for the killing of NK cells against HT29 cells was the E:T ratio (i.e., NK:HT29) being about 3:1.

HT29 cells were plated into culture plates at 30% confluency and incubated in DMEM+10% FBS at 37° C. in 5% CO$_2$ for 24 hours. Then, the medium was replaced with serum-free DMEM, and ddvv-RFP was added (MOI=0.2). After a six-hour infection, the medium was replaced with DMEM+10% FBS, and the cells were incubated at 37° C. in 5% CO2 to 24 hours. The medium was replaced with fresh DMEM+10% FBS, and NK cells were added (E:T ratio (NK:HT29)=3:1), and the cells were further incubated for 48 hours. Dead cells and debris were washed off, and Trypan Blue Staining method was used for counting the remaining living HT29 cells. In the experiment, there were also a blank control group, in which none of the virus or NK cells were added to HT29 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 43:
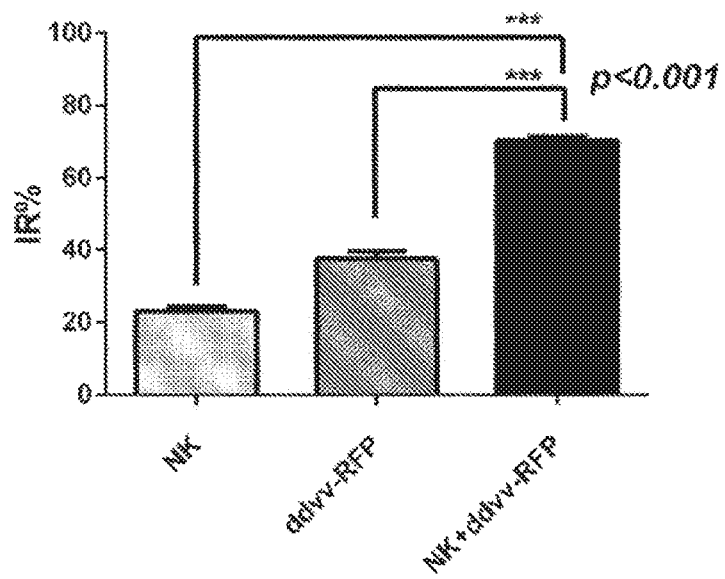
FIG. 43 shows the result of the combined killing experiment of ddvv-RFP and NK cells administered at an interval of 24 hours in Example F2 according to the present disclosure.

As shown in FIG. 43 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against HT29 cells, and the synergistic inhibition rate was about 70%. However, in this experiment, the inhibition rate of single application of ddvv-RFP was about 38% and the inhibition rate of single application of the NK cells was about 23%.

Example F3: Combined Killing Experiment of ddvv-RFP and NK

Figure 46:
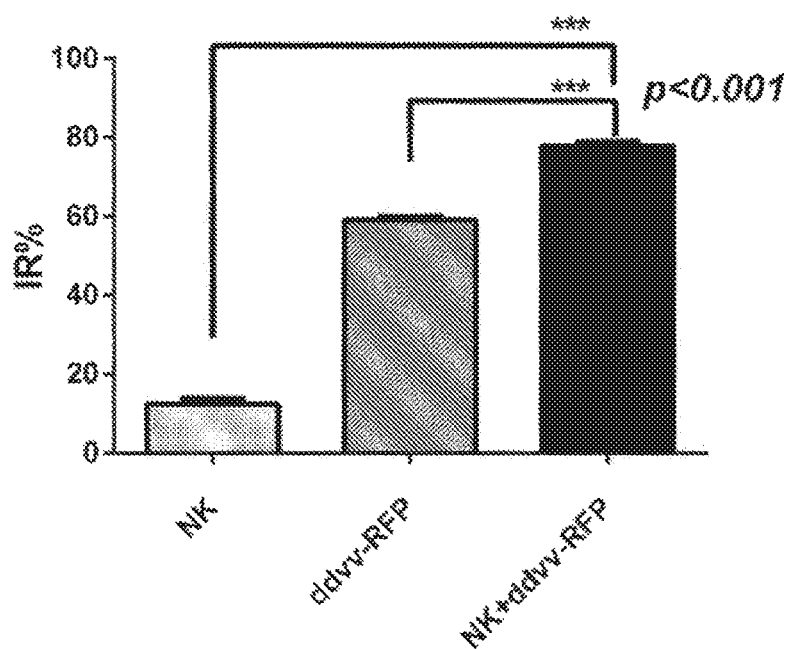
FIG. 46 shows the result of the combined killing experiment of ddvv-RFP and NK cells administered at an interval of 48 hours in Example F3 according to the present disclosure.

Example F3 was similar to the above Example F2 except that, after infection by adding ddvv-RFP, the cells were incubated to 48 hours instead of 24 hours, and then NK cells were added. As shown in FIG. 46 (wherein X axis represents the different groups, and Y axis represents the corresponding percentage values of inhibition rates), the final result also demonstrated that the combined application of ddvv-RFP and NK cells (the oncolytic virus being administered first and the NK cells later) had significant synergistic killing effect against HT29 cells, and the synergistic inhibition rate was about 78%. However, in this experiment, the inhibition rate of single application of ddvv-RFP was about 59% and the inhibition rate of single application of the NK cells was about 12%.

Comparative Example F4: Simultaneous Combined Administration of the Drugs

HT29 cells were plated into culture plates at 30% confluency and incubated in DMEM+10% FBS at 37° C. in 5% $CO_2$ for 24 hours. Then, the medium was replaced with serum-free DMEM, and ddvv-RFP was added (MOI=0.2). After a six-hour infection, the medium was replaced with fresh DMEM+10% FBS, and NK cells were added (E:T ratio (NK:HT29)=3:1). The cells were further incubated to 72 hours, then dead cells and debris were washed off, and the remaining living HT29 cells were counted using Trypan Blue Staining method. In the experiment, there were also a blank control group, in which none of the virus or NK cells were added to HT29 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 44:
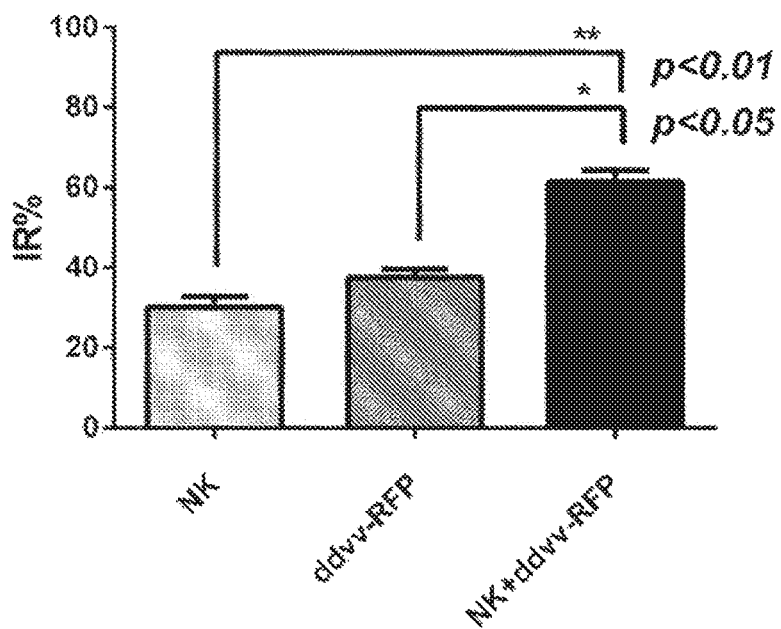
FIG. 44 shows the result of the simultaneous combined administration of ddvv-RFP and NK cells in Comparative example F4 according to the present disclosure.

As shown in FIG. 44 (wherein X axis represents the different groups, and Y axis represents the corresponding percentage values of inhibition rates), the inhibition rate of the single application of ddvv-RFP was about 38% and the inhibition rate of single application of the NK cells was about 30%. Compared to these single applications, the inhibition rate of combined use of NK cells and ddvv-RFP was increased, which was about 61%; however, no significant synergistic effect was shown.

Comparative Example F5: Simultaneous Combined Administration of the Drugs

Figure 47:
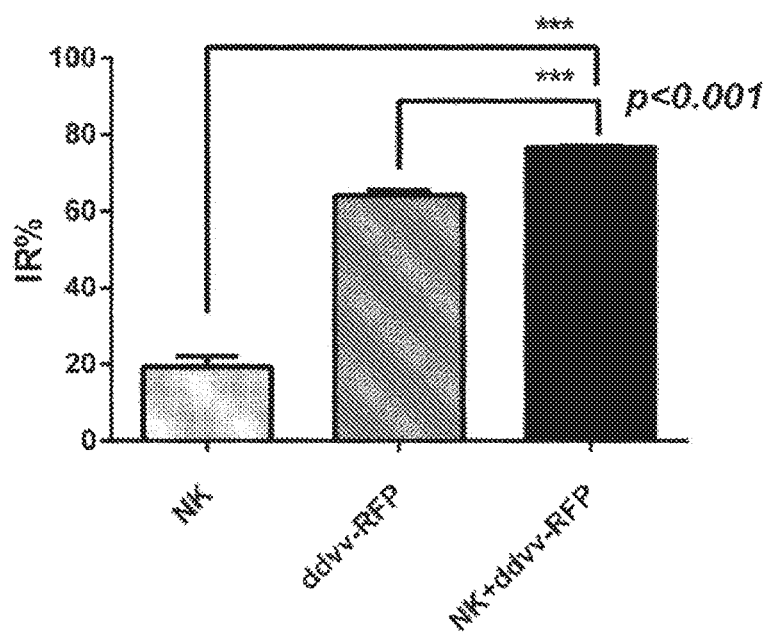
FIG. 47 shows the result of the simultaneous combined administration of ddvv-RFP and NK cells in Comparative example F5 according to the present disclosure.

Comparative example F5 was similar to the above Comparative example F4 except that, after adding ddvv-RFP and NK, the cells were incubated to 96 hours instead of 72 hours. As shown in FIG. 47 (wherein X axis represents the different groups, and Y axis represents the corresponding percentage values of inhibition rates), the inhibition rate of the single application of ddvv-RFP was about 64% and the inhibition rate of single application of the NK cells was about 19%. Compared to these single applications, the inhibition rate of combined use of NK cells and ddvv-RFP was increased, which was about 77%; however, no significant synergistic effect was shown.

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells—when ddvv-RFP and NK cells were administered simultaneously, the combined application did not show a synergistic effect; whereas when NK cells were administered about 24 to 48 hours after the administration of ddvv-RFP, the combined application showed a significant synergistic effect.

Comparative Example F6: Comparison Between Different Administration Sequences in Combined Application HT29 cells were plated into culture plates at 30% confluency and incubated in DMEM+10% FBS at 37° C. in 5% $CO_2$ for 24 hours. Then, the medium was replaced with fresh DMEM+10% FBS, and NK cells were added (E:T ratio (NK:HT29)=3:1). The cells were incubated at 37° C. in 5% $CO_2$ for 24 hours. Then, ddvv-RFP (MOI=0.2) was added without replacing the medium, and the cells were further incubated for 48 hours. Dead cells and debris were washed off, and Trypan Blue Staining method was used for counting the remaining living HT29 cells. In the experiment, there were also a blank control group, in which none of the virus or NK cells were added to HT29 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 45:
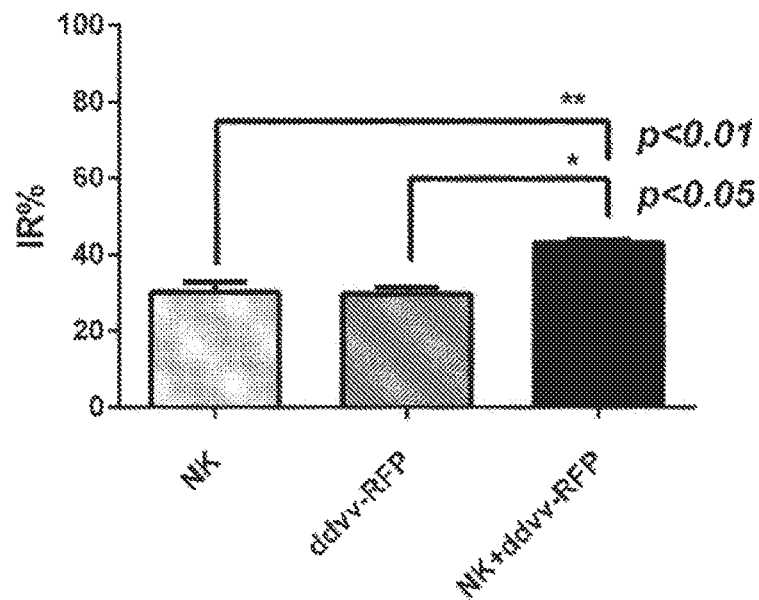
FIG. 45 shows the result of the combined administration of ddvv-RFP and NK cells at an interval of 24 hours in a reverse sequential manner in Comparative example F6 according to the present disclosure.

As shown in FIG. 45 (wherein X axis represents the different groups, and Y axis represents the corresponding percentage values of inhibition rates), the inhibition rate of the combined application in a reverse sequential manner (NK cells being administered first and ddvv-RFP later) was about 43%, the inhibition rate of the single application of ddvv-RFP was about 30%, and the inhibition rate of single application of the NK cells was about 30%. The combined application in the reverse sequential manner did not show a synergistic effect.

Figure 48:
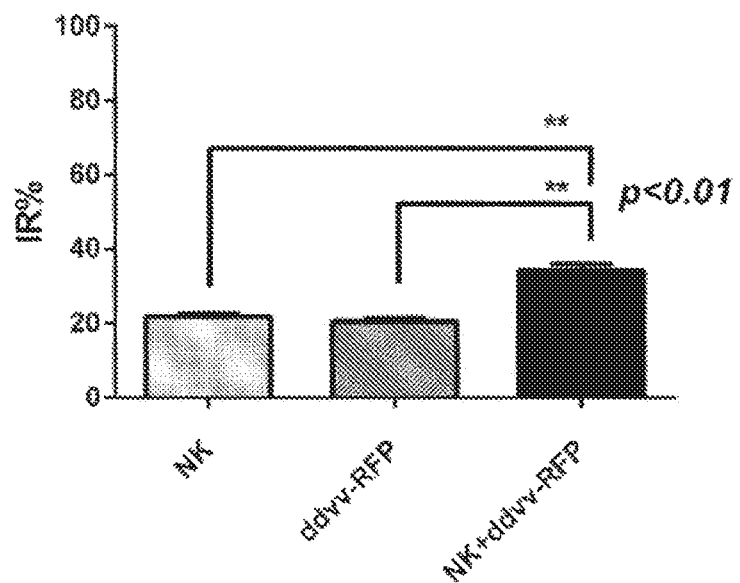
FIG. 48 shows the result of the combined administration of ddvv-RFP and NK cells at an interval of 48 hours in a reverse sequential manner in Comparative example F7 according to the present disclosure.

Comparative Example F7: Comparison Between Different Administration Sequences in Combined Application Comparative example F7 was similar to the above Comparative example F6 except that after adding NK the cells were incubated to 48 hours instead of 24 hours, and then ddvv-RFP was added. As shown in FIG. 48 (wherein X axis represents the different groups, and Y axis represents the corresponding percentage values of inhibition rates), the inhibition rate of the combined application in a reverse sequential manner (NK cells being administered first and ddvv-RFP later) was about 34%, the inhibition rate of the single application of ddvv-RFP was about 21%, and the inhibition rate of single application of the NK cells was about 22%. The combined application in the reverse sequential manner did not show a synergistic effect.

G: Study on the Killing Effect of Combined Application of Oncolytic Vaccinia Virus and NK Cells Against HCT116 Cells

Figure 49:
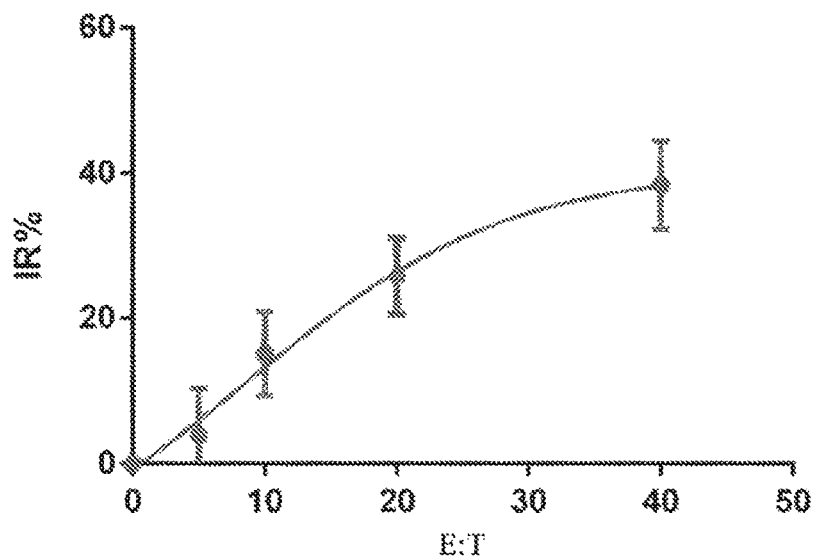
FIG. 49 shows the result of a dose-response experiment of the combined administration of NK cells against HCT116 cells in Experimental example G1 according to the present disclosure.

Experimental Example G1: Dose-Response Experiment of NK Cells Against HCT116 Cells HCT116 cells were plated into culture plates at 30% confluency and incubated in McCoy's 5A+10% FBS at 37° C. in 5% $CO_2$ for 48 hours. Then, the medium was replaced with fresh McCoy's 5A+10% FBS, and NK cells were added with the effector to target cell ratios (i.e., E:T, ratio of cell numbers) as follows: NK:HCT116=40:1, 20:1, 10:1, and 5:1, respectively. The killing process at each E:T ratio lasted for 48 hours with the cells being incubated at 37° C. In 5% $CO_2$. Afterwards, Trypan Blue Staining method was used for counting the living HCT116 cells, and the killing rates of HCT116 cells by NK cells were calculated relative to the control group in which no NK cells were added. The dose-response curve is shown in FIG. 49 (wherein X axis represents E:T ratio, and Y axis represents the percentage value of inhibition rate (IR)), which exhibits an inhibition rate of about 13% when E:T ratio is 10:1, indicating a suitable dose level. This dosage was adopted as the dose level of NK cells to be used in the combined killing experiment.

Figure 50:
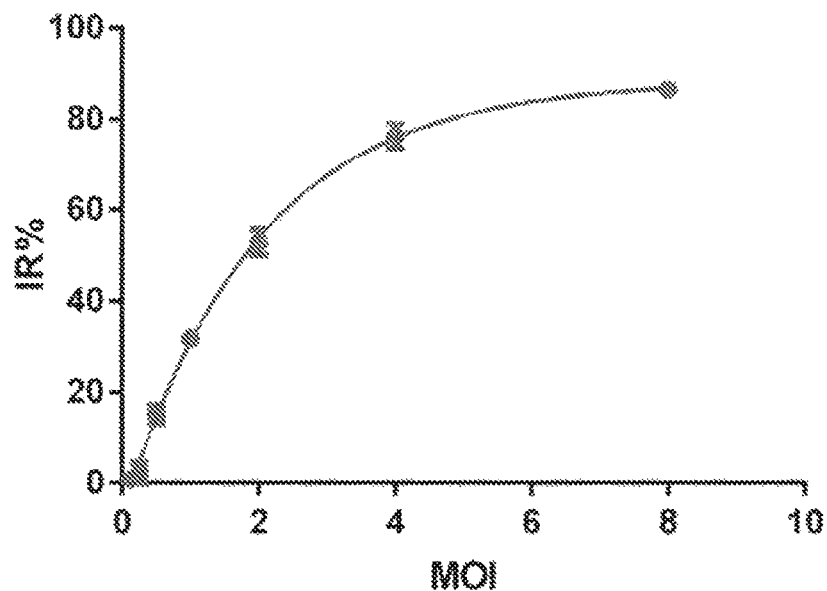
FIG. 50 shows the result of a dose-response experiment of ddvv-RFP against HCT116 cells in Experimental example G2 according to the present disclosure.

Experimental Example G2: Dose-Response Experiment of ddvv-RFP Against HCT116 Cells HCT116 cells were plated into culture plates at 30% confluency and incubated in McCoy's 5A+10% FBS at 37° C. in 5% $CO_2$ for 24 hours. Then, the medium was replaced with fresh serum-free McCoy's 5A, and ddvv-RFP was added with MOI being MOI=8, 4, 2, 1, 0.5, 0.25, and 0.125, respectively. The infection process lasted for 6 hours with the cells being incubated at 37° C. in 5% $CO_2$, then the medium was removed, and the cells were washed with PBS. Then, McCoy's 5A+10% FBS was added, and the cells were further incubated to 72 hours. Afterwards, Trypan Blue Staining method was used for counting the living HCT116 cells, and the killing rates of HCT116 cells by ddvv-RFP were calculated relative to the control group in which no ddvv-RFP was added. FIG. 50 shows the dose-response curve (wherein X axis represents MOI, and Y axis represents the percentage value of inhibition rate (IR)), which exhibits an inhibition rate of about 22% when the dose level of ddvv-RFP against HCT116 cells is the MOI being about 0.7, indicating a suitable dose level. This dosage was adopted as the dose level of ddvv-RFP to be used in the combined killing experiment.

Example G3: Combined Killing Experiment of ddvv-RFP and NK

It can be concluded from the above Experimental examples that the suitable dose level for the killing of ddvv-RFP against HCT116 cells was the MOI being about 0.7; and the suitable dose level for the killing of NK cells against HCT116 cells was the E:T ratio (i.e., NK:HCT116) being about 10:1.

HCT116 cells were plated into culture plates at 30% confluency and incubated in McCoy's 5A+10% FBS at 37° C. in 5% $CO_2$ for 24 hours. Then, the medium was replaced with serum-free McCoy's 5A, and ddvv-RFP was added (MOI=0.7). After a six-hour infection, the medium was replaced with McCoy's 5A+10% FBS, and the cells were incubated at 37° C. in 5% CO2 to 24 hours. Then, NK cells were added (E:T ratio (NK:HCT116)=10:1) without replacing the medium, and the cells were further incubated for 48 hours. Dead cells and debris were washed off, and Trypan Blue Staining method was used for counting the remaining living HCT116 cells. In the experiment, there were also a blank control group, in which none of the virus or NK cells were added to HCT116 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 51:
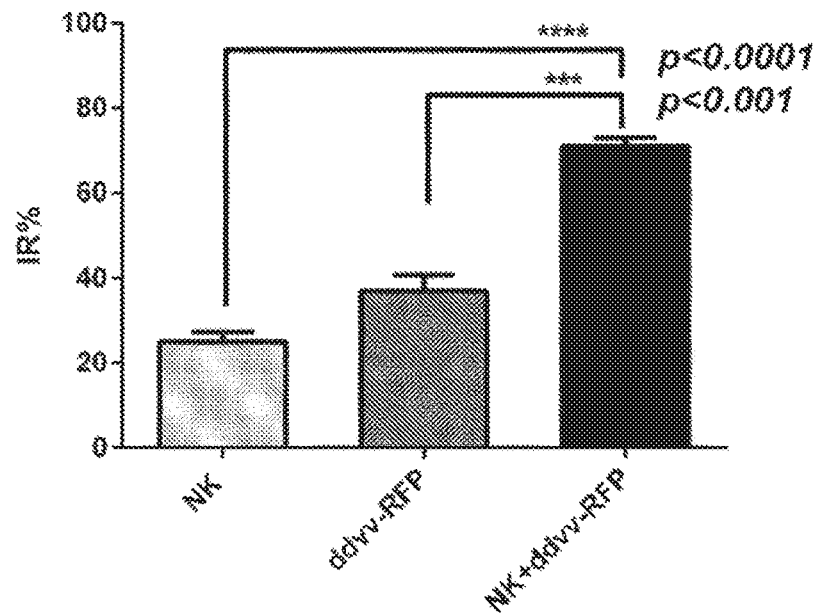
FIG. 51 shows the result of the combined killing experiment of ddvv-RFP and NK cells in Example G3 according to the present disclosure.

As shown in FIG. 51 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against HCT116 cells, and the synergistic inhibition rate was about 71%. However, in this experiment, the inhibition rate of single application of ddvv-RFP was about 37% and the inhibition rate of single application of the NK cells was about 25%.

Comparative Example G4: Simultaneous Combined Administration of the Drugs

HCT116 cells were plated into culture plates at 30% confluency and incubated in McCoy's 5A+10% FBS at 37° C. in 5% $CO_2$ for 24 hours. Then, the medium was replaced with serum-free McCoy's 5A, and ddvv-RFP was added (MOI=0.7). After a six-hour infection, the medium was replaced with fresh McCoy's 5A+10% FBS, and NK cells were added (E:T ratio (NK:HCT116)=10:1). The cells were further incubated to 72 hours, then dead cells and debris were washed off, and the remaining living HCT116 cells were counted using Trypan Blue Staining method. In the experiment, there were also a blank control group, in which none of the virus or NK cells were added to HCT116 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 52:
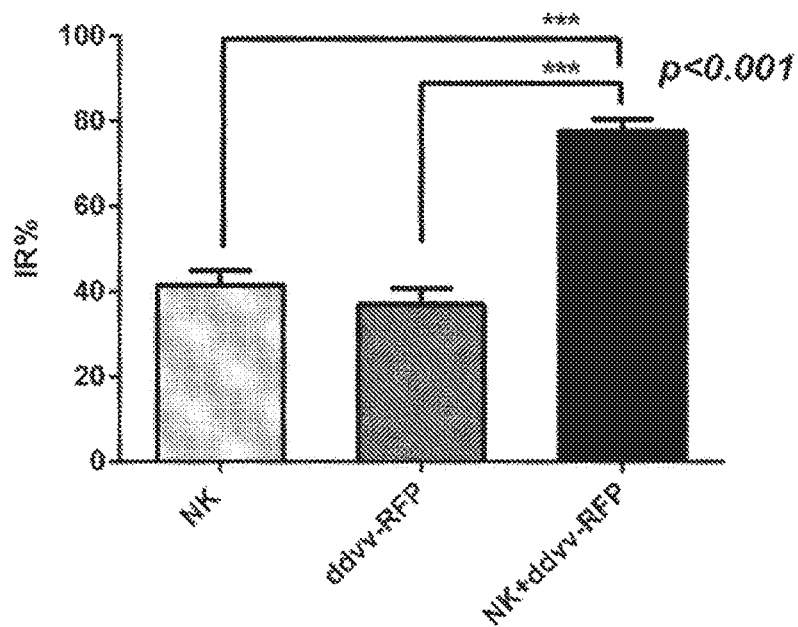
FIG. 52 shows the result of the simultaneous combined administration of ddvv-RFP and NK cells in Comparative example G4 according to the present disclosure.

As shown in FIG. 52 (wherein X axis represents the different groups, and Y axis represents the corresponding percentage values of inhibition rates), the inhibition rate of the single application of ddvv-RFP was about 37% and the inhibition rate of single application of the NK cells was about 41%. Compared to these single applications, the inhibition rate of combined use of NK cells and ddvv-RFP was increased, which was about 78%; however, no significant synergistic effect was shown.

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells— when ddvv-RFP and NK cells were substantially administered simultaneously, the combined application did not show a synergistic effect; whereas when ddvv-RFP was administered first and NK cells later, the combined application showed a significant synergistic effect.

Comparative Example G5: Comparison Between Different Administration Sequences in Combined Application HCT116 cells were plated into culture plates at 30% confluency and incubated in McCoy's 5A+10% FBS at 37° C. in 5% $CO_2$ for 24 hours. Then, NK cells were added (E:T ratio (NK:HCT116)=10:1) without replacing the medium, and the cells were incubated at 37° C. in 5% $CO_2$ for 24 hours. Then, ddvv-RFP (MOI=0.7) was added without replacing the medium, and the cells were further incubated for 48 hours. Dead cells and debris were washed off, and Trypan Blue Staining method was used for counting the remaining living HCT116 cells. In the experiment, there were also a blank control group, in which none of the virus or NK cells were added to HCT116 cells; a ddvv-RFP group, in which ddvv-RFP was added at its corresponding time point but no NK cells were added; and a NK group, in which the NK cells were added at their corresponding time point but no ddvv-RFP was added. All the experiments were repeated for over 3 times, and the averages were used for statistical analysis.

Figure 53:
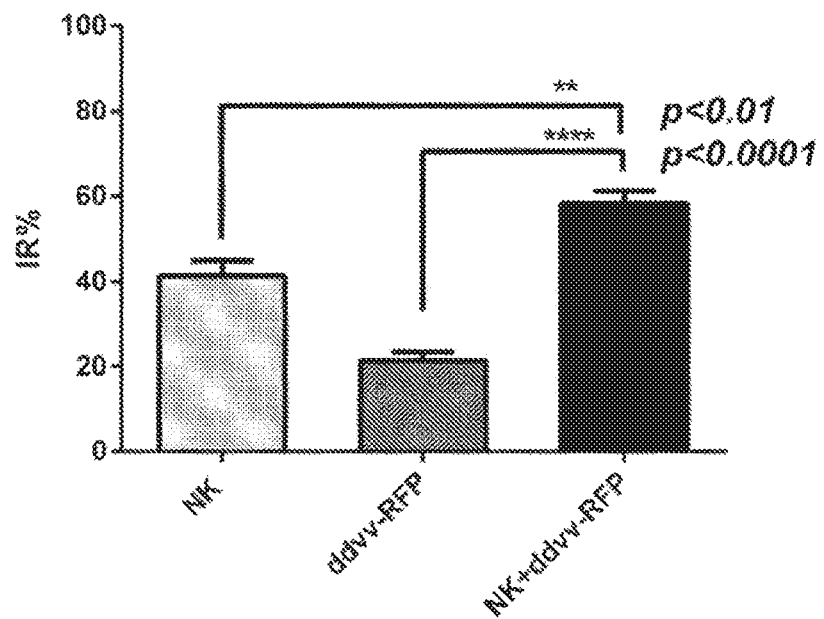
FIG. 53 shows the result of the combined administration of ddvv-RFP and NK cells in a reverse sequential manner in Comparative example G5 according to the present disclosure.

As shown in FIG. 53 (wherein X axis represents the different groups, and Y axis represents the corresponding percentage values of inhibition rates), the inhibition rate of the combined application in a reverse sequential manner (NK cells being administered first and ddvv-RFP later) was about 58%, the inhibition rate of the single application of ddvv-RFP was about 21%, and the inhibition rate of single application of the NK cells was about 41%. The combined application in the reverse sequential manner did not show a synergistic effect.

Figure 54:
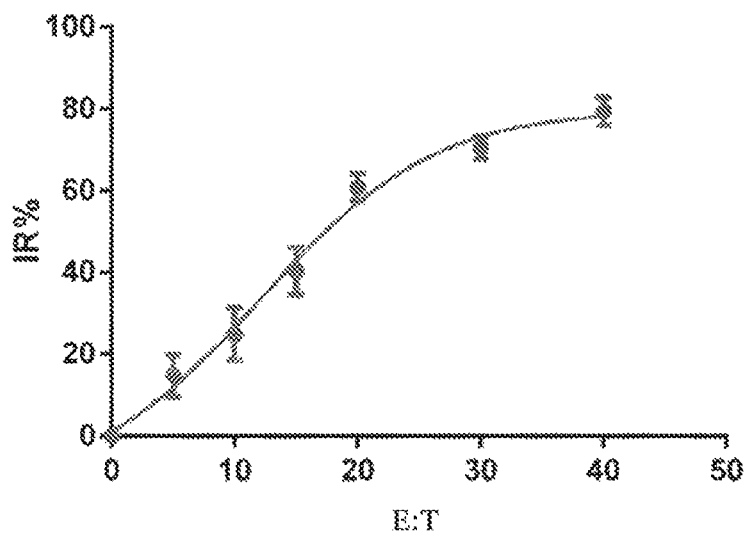
FIG. 54 shows the result of a dose-response experiment of NK cells against FaDu cells in Experimental example H1 according to the present disclosure.

H: Study on the Killing Effect of Combined Application of Oncolytic Vaccinia Virus and NK Cells Against FaDu Cells Experimental Example H1: Dose-Response Experiment of NK Cells Against FaDu Cells FaDu cells were plated into culture plates at 30% confluency and incubated in MEM+10% FBS at 37° C. In 5% $CO_2$ for 48 hours. Then, the medium was replaced with fresh MEM+10% FBS, and NK cells were added with the effector to target cell ratios (i.e., E:T, ratio of cell numbers) as follows: NK:FaDu=40:1, 30:1, 20:1, 15:1, 10:1, and 5:1, respectively. The killing process at each E:T ratio lasted for 48 hours with the cells being incubated at 37° C. in 5% $CO_2$. Afterwards, Trypan Blue Staining method was used for counting the living FaDu cells, and the killing rates of FaDu cells by NK cells were calculated relative to the control group in which no NK cells were added. The dose-response curve is shown in FIG. 54 (wherein X axis represents E:T ratio, and Y axis represents the percentage value of inhibition rate (IR)), which exhibits an inhibition rate of about 27% when E:T ratio is 10:1, indicating a suitable dose level. This dosage was adopted as the dose level of NK cells to be used in the combined killing experiment.

Figure 55:
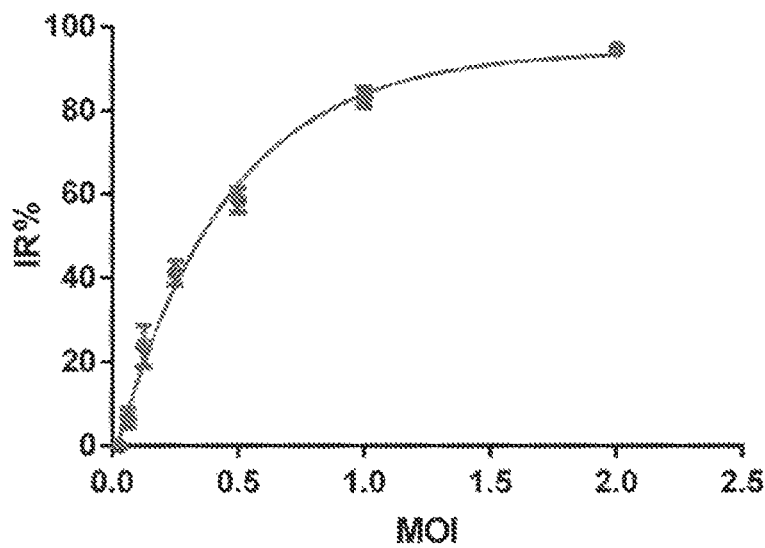
FIG. 55 shows the result of a dose-response experiment of ddvv-RFP against FaDu cells in Experimental example H2 according to the present disclosure.

Experimental Example H2: Dose-Response Experiment of ddvv-RFP Against FaDu Cells FaDu cells were plated into culture plates at 30% confluency and incubated in MEM+10% FBS at 37° C. In 5% $CO_2$ for 24 hours. Then, the medium was replaced with fresh serum-free MEM, and ddvv-RFP was added with MOI being MOI=2, 1, 0.5, 0.25, 0.125, 0.0625 and 0.03125, respectively. The infection process lasted for 6 hours with the cells being incubated at 37° C. In 5% $CO_2$, then the medium was removed, and the cells were washed with PBS. Then, MEM+10% FBS was added, and the cells were further incubated to 72 hours. Afterwards, Trypan Blue Staining method was used for counting the living FaDu cells, and the killing rates of FaDu by ddvv-RFP were calculated relative to the control group in which no ddvv-RFP was added. FIG. 55 shows the dose-response curve (wherein X axis represents MOI, and Y axis represents the percentage value of inhibition rate (IR)), which exhibits an inhibition rate of about 32% when the dose level of ddvv-RFP against FaDu cells is the MOI being about 0.2, indicating a suitable dose level. This dosage was adopted as the dose level of ddvv-RFP to be used in the combined killing experiment.

Example H3: Combined Killing Experiment of ddvv-RFP and NK Cells

It can be concluded from the above Experimental examples that the suitable dose level for the killing of ddvv-RFP against FaDu cells was the MOI being about 0.2; and the suitable dose level for the killing of NK cells against FaDu cells was the E:T ratio (i.e., NK:FaDu) being about 10:1.

FaDu cells ware plated into culture plates at 30% confluency and incubated in MEM+10% FBS at 37° C. In 5% $CO_2$ for 24 hours. Then, the medium was replaced with serum-free MEM, and ddvv-RFP was added (MOI=0.2). After a six-hour infection, the medium was replaced with MEM+ 10% FBS, and the cells were incubated at 37° C. In 5% CO2 to 24 hours. Then, NK cells were added (E:T ratio (NK: FaDu)=10:1) without replacing the medium, and the cells were further incubated for 48 hours. Dead cells and debris ware washed off, and Trypan Blue Staining method was used for counting the remaining living FaDu cells. In the experiment, there were also a blank control group, in which none of the virus or NK cells were added to FaDu cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages ware used for statistical analysis.

Figure 56:
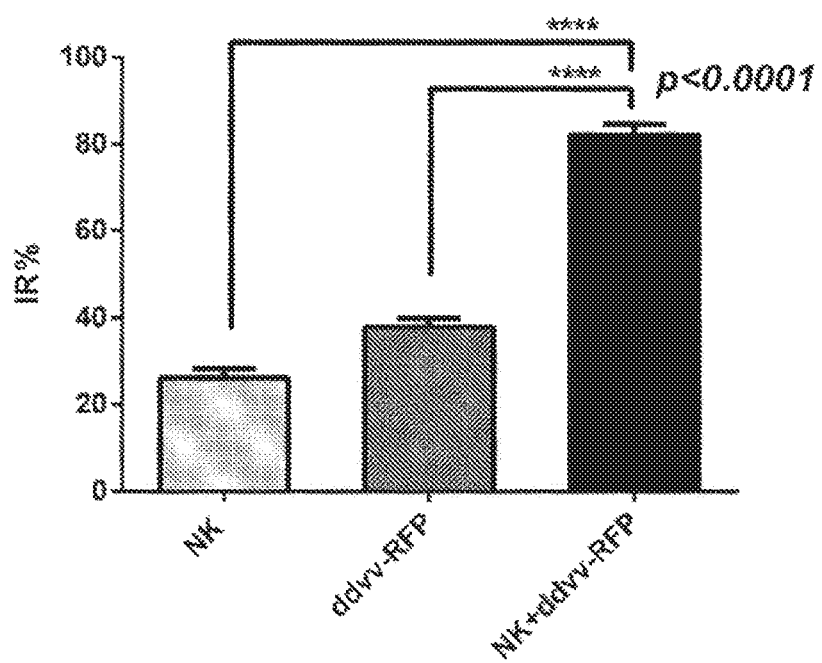
FIG. 56 shows the result of the combined killing experiment of ddvv-RFP and NK cells in Example H3 according to the present disclosure.

As shown in FIG. 56 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against FaDu cells, and the synergistic inhibition rate was about 82%. However, in this experiment, the inhibition rate of single application of ddvv-RFP was about 38% and the inhibition rate of single application of the NK cells was about 26%.

Comparative Example H4: Simultaneous Combined Administration of the Drugs

FaDu cells were plated into culture plates at 30% confluency and incubated in MEM+10% FBS at 37° C. in 5% $CO_2$ for 24 hours. Then, the medium was replaced with serum-free MEM, and ddvv-RFP was added (MOI=0.2). After a six-hour infection, the medium was replaced with fresh MEM+10% FBS, and NK cells were added (E:T ratio (NK:FaDu)=10:1). The cells were further incubated to 72 hours, then dead cells and debris were washed off, and the remaining living FaDu cells were counted using Trypan Blue Staining method. In the experiment, there were also a blank control group, in which none of the virus or NK cells were added to FaDu cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 57:
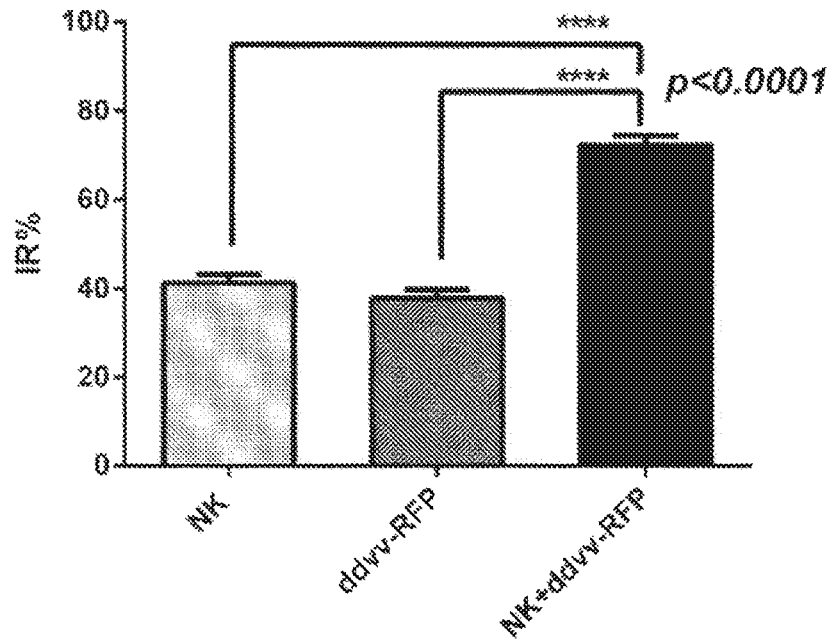
FIG. 57 shows the result of the simultaneous combined administration of ddvv-RFP and NK cells in Comparative example H4 according to the present disclosure.

As shown in FIG. 57 (wherein X axis represents the different groups, and Y axis represents the corresponding percentage values of inhibition rates), the inhibition rate of the single application of ddvv-RFP was about 38% and the inhibition rate of single application of the NK cells was about 41%. Compared to these single applications, the inhibition rate of combined use of NK cells and ddvv-RFP was increased, which was about 72%; however, no significant synergistic effect was shown.

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells— when ddvv-RFP and NK cells were substantially administered simultaneously, the combined application did not show a synergistic effect; whereas when ddvv-RFP was administered first and NK cells later, the combined application showed a significant synergistic effect.

Comparative Example H5: Comparison Between Different Administration Sequences in Combined Application FaDu cells were plated into culture plates at 30% confluency and incubated in MEM+10% FBS at 37° C. in 5% $CO_2$ for 24 hours. Then, NK cells were added (E:T ratio (NK:FaDu)=10:1) without replacing the medium, and the cells were incubated at 37° C. in 5% $CO_2$ for 24 hours. Then, ddvv-RFP (MOI=0.2) was added without replacing the medium, and the cells were further incubated for 48 hours. Dead cells and debris were washed off, and Trypan Blue Staining method was used for counting the remaining living FaDu cells. In the experiment, there were also a blank control group, in which none of the virus or NK cells were added to FaDu cells; a ddvv-RFP group, in which ddvv-RFP was added at its corresponding time point but no NK cells were added; and a NK group, in which the NK cells were added at their corresponding time point but no ddvv-RFP was added. All the experiments were repeated for over 3 times, and the averages were used for statistical analysis.

Figure 58:
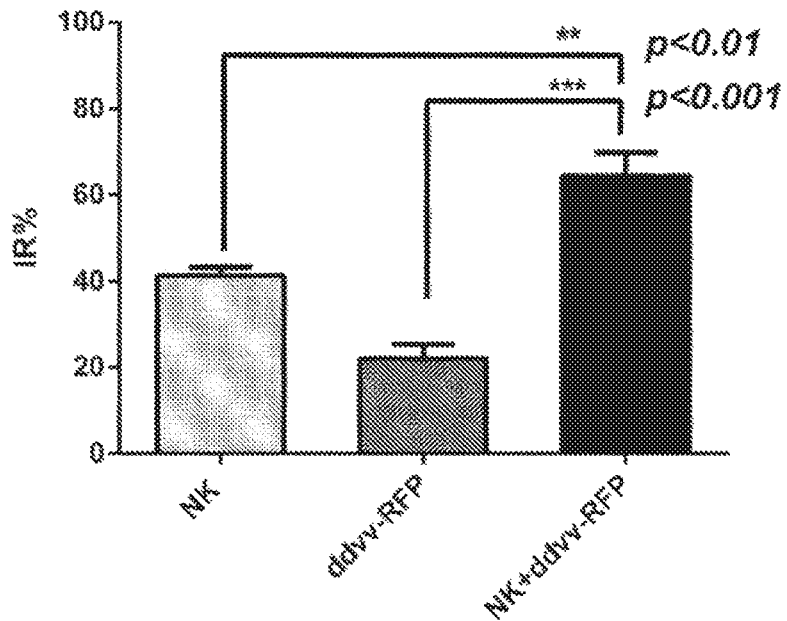
FIG. 58 shows the result of the combined administration of ddvv-RFP and NK cells in a reverse sequential manner in Comparative example H5 according to the present disclosure.

As shown in FIG. 58 (wherein X axis represents the different groups, and Y axis represents the corresponding percentage values of inhibition rates), the inhibition rate of the combined application in a reverse sequential manner (NK cells being administered first and ddvv-RFP later) was about 64%, the inhibition rate of the single application of ddvv-RFP was about 22% and the inhibition rate of single application of the NK cells was about 41%. The combined application in the reverse sequential manner did not show a significant synergistic effect ($P>0.8$).

Figure 59:
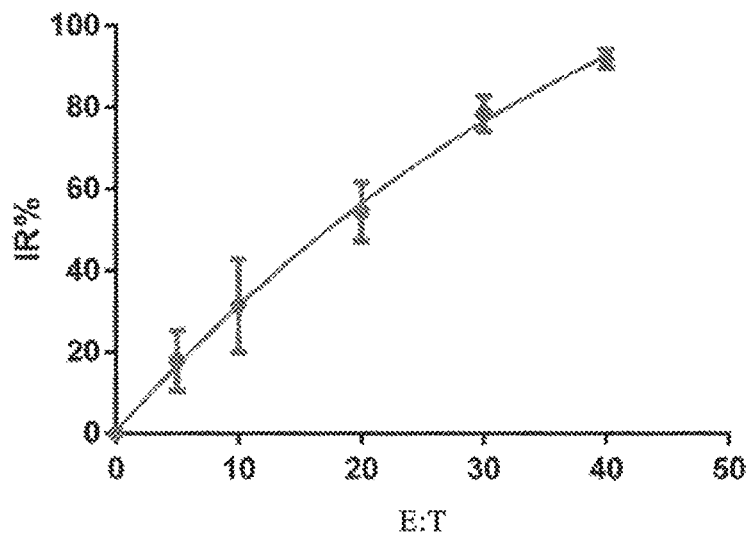
FIG. 59 shows the result of a dose-response experiment of NK cells against SK-HEP-1 in Experimental example I1 according to the present disclosure.

I: Study on the Killing Effect of Combined Application of Oncolytic Vaccinia Virus and NK Cells Against SK-HEP-1 Cells Experimental Example I1: Dose-Response Experiment of NK Cells Against SK-HEP-1 Cells SK-HEP-1 cells were plated into culture plates at 30% confluency and incubated in MEM+10% FBS at 37° C. In 5% $CO_2$ for 48 hours. Then, the medium was replaced with fresh MEM+10% FBS, and NK cells were added with the effector to target cell ratios (i.e., E:T, ratio of cell numbers) as follows: NK:SK-HEP-1=40:1, 30:1, 20:1, 10:1, and 5:1, respectively. The killing process at each E:T ratio lasted for 48 hours with the cells being incubated at 37° C. in 5% $CO_2$. Afterwards, Trypan Blue Staining method was used for counting the living SK-HEP-1 cells, and the killing rates of SK-HEP-1 cells by NK cells were calculated relative to the control group in which no NK cells were added. FIG. 59 shows the dose-response curve (wherein X axis represents E:T ratio, and Y axis represents the percentage value of inhibition rate (IR)), which exhibits an inhibition rate of about 17% when E:T ratio is 5:1, indicating a suitable dose level. This dosage was adopted as the dose level of NK cells to be used in the combined killing experiment.

Figure 60:
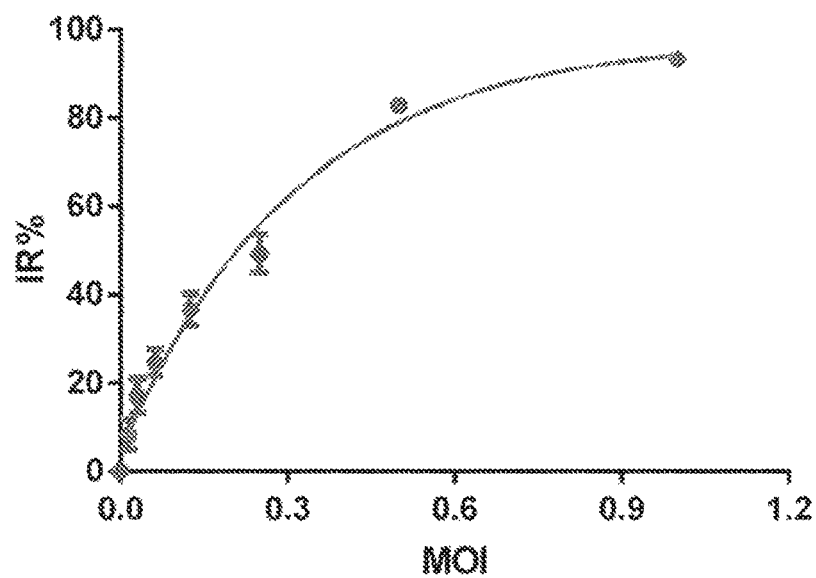
FIG. 60 shows the result of a dose-response experiment of ddvv-RFP against SK-HEP-1 cells in Experimental example I2 according to the present disclosure.

Experimental Example I2: Dose-Response Experiment of ddvv-RFP Against SK-HEP-1 Cells SK-HEP-1 cells were plated into culture plates at 30% confluency and incubated in MEM+10% FBS at 37° C. in 5% $CO_2$ for 24 hours. Then, the medium was replaced with fresh serum-free MEM, and ddvv-RFP was added with MOI being MOI=1, 0.5, 0.25, 0.125, 0.0625, 0.03 and 0.015, respectively. The infection process lasted for 6 hours with the cells being incubated at 37° C. in 5% $CO_2$, then the medium was removed, and the cells were washed with PBS. Then, MEM+10% FBS was added, and the cells were further incubated to 72 hours. Afterwards, Trypan Blue Staining method was used for counting the living SK-HEP-1 cells, and the killing rates of SK-HEP-1 by ddvv-RFP were calculated relative to the control group in which no ddvv-RFP was added. FIG. 60 shows the dose-response curve (wherein X axis represents MOI, and Y axis represents the percentage value of inhibition rate (IR)), which exhibits an inhibition rate of about 40% when the dose level of ddvv-RFP against SK-HEP-1 cells is the MOI being about 0.15, indicating a suitable dose level. This dosage was adopted as the dose level of ddvv-RFP to be used in the combined killing experiment.

Example I3: Combined Killing Experiment of ddvv-RFP and NK

It can be concluded from the above Experimental examples that the suitable dose level for the killing of ddvv-RFP against SK-HEP-1 cells was the MOI being about 0.15; and the suitable dose level for the killing of NK cells against SK-HEP-1 cells was the E:T ratio (i.e., NK:SK-HEP-1) being about 5:1.

SK-HEP-1 cells were plated into culture plates at 30% confluency and incubated in MEM+10% FBS at 37° C. in 5% $CO_2$ for 24 hours. Then, the medium was replaced with serum-free MEM, and ddvv-RFP was added (MOI=0.15). After a six-hour infection, the medium was replaced with MEM+10% FBS, and the cells were incubated at 37° C. In 5% CO2 to 24 hours. The medium was replaced with fresh MEM+10% FBS, and NK cells were added (E:T ratio (NK:SK-HEP-1)=5:1), and the cells were further incubated for 48 hours. Dead cells and debris were washed off, and Trypan Blue Staining method was used for counting the remaining living SK-HEP-1 cells. In the experiment, there were also a blank control group, in which none of the virus or NK cells were added to SK-HEP-1 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 61:
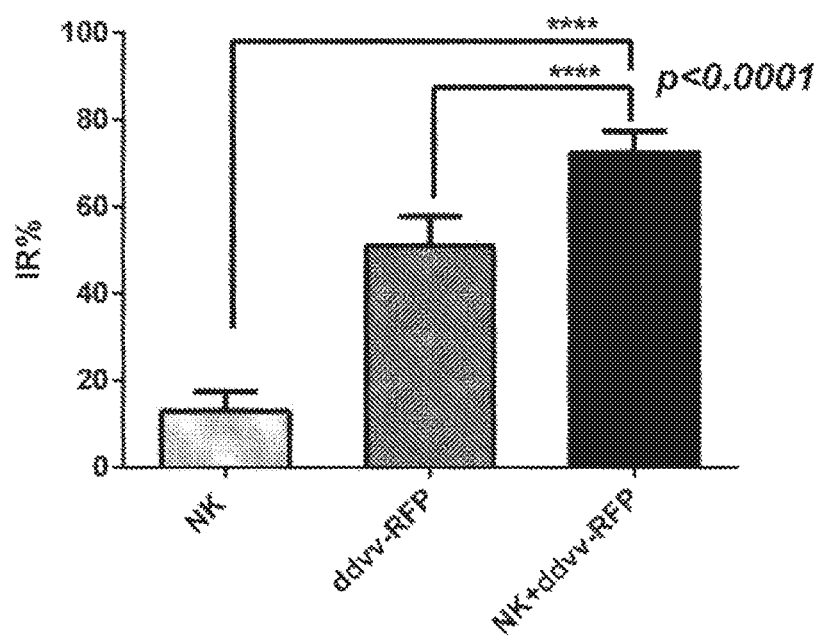
FIG. 61 shows the result of the combined killing experiment of ddvv-RFP and NK cells in Example I3 according to the present disclosure.

As shown in FIG. 61 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against SK-HEP-1 cells, and the synergistic inhibition rate was about 72%. However, in this experiment, the inhibition rate of single application of ddvv-RFP was about 51% and the inhibition rate of single application of the NK cells was about 13%.

Comparative Example I4: Simultaneous Combined Administration of the Drugs

SK-HEP-1 cells were plated into culture plates at 30% confluency and incubated in MEM+10% FBS at 37° C. in 5% $CO_2$ for 24 hours. Then, the medium was replaced with serum-free MEM, and ddvv-RFP was added (MOI=0.15). After a six-hour infection, the medium was replaced with fresh MEM+10% FBS, and NK cells were added (E:T ratio (NK:SK-HEP-1)=5:1). The cells were further incubated to 72 hours, then dead cells and debris were washed off, and the remaining living SK-HEP-1 cells were counted using Trypan Blue Staining method. In the experiment, there were also a blank control group, in which none of the virus or NK cells were added to SK-HEP-1 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 62:
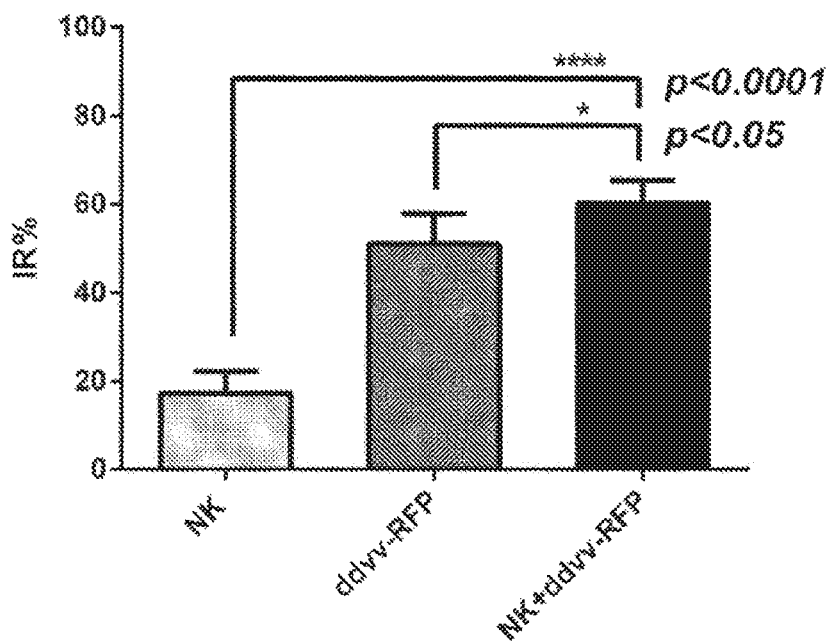
FIG. 62 shows the result of the simultaneous combined administration of ddvv-RFP and NK cells in Comparative example I4 according to the present disclosure.

As shown in FIG. 62 (wherein X axis represents the different groups, and Y axis represents the corresponding percentage values of inhibition rates), the inhibition rate of the single application of ddvv-RFP was about 51% and the inhibition rate of single application of the NK cells was about 17%. Compared to these single applications, the inhibition rate of combined use of NK cells and ddvv-RFP was increased, which was about 60%; however, no significant synergistic effect was shown.

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells—when ddvv-RFP and NK cells were substantially administered simultaneously, the combined application did not show a synergistic effect; whereas when ddvv-RFP was administered first and NK cells later, the combined application showed a significant synergistic effect.

Comparative Example I5: Comparison Between Different Administration Sequences in Combined Application SK-HEP-1 cells were plated into culture plates at 30% confluency and incubated in MEM+10% FBS at 37° C. in 5% $CO_2$ for 24 hours. Then, the medium was replaced with fresh MEM+10% FBS, and NK cells were added (E:T ratio (NK:SK-HEP-1)=5:1). The cells were incubated at 37° C. in 5% $CO_2$ for 24 hours. Then, ddvv-RFP (MOI=0.15) was added without replacing the medium, and the cells were further incubated for 48 hours. Dead cells and debris were washed off, and Trypan Blue Staining method was used for counting the remaining living SK-HEP-1 cells. In the experiment, there were also a blank control group, in which none of the virus or NK cells were added to SK-HEP-1 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 63:
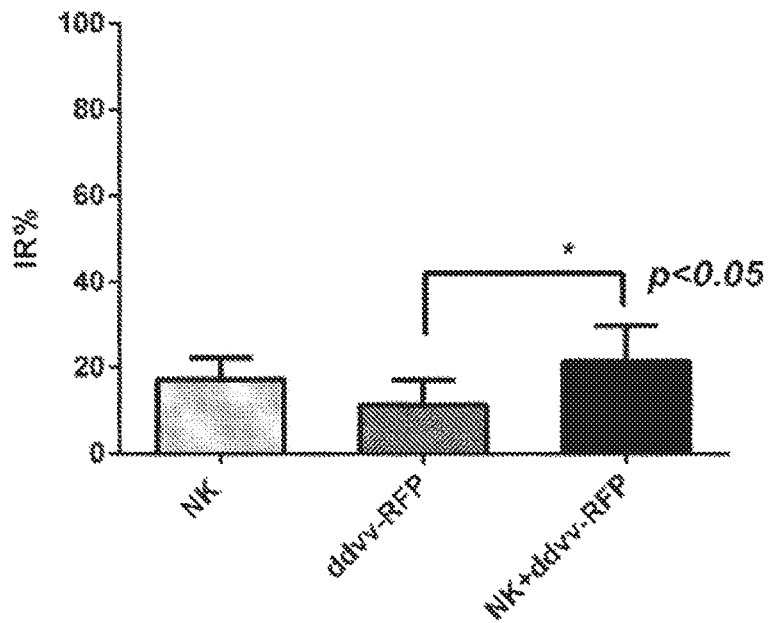
FIG. 63 shows the result of the combined administration of ddvv-RFP and NK cells in a reverse sequential manner in Comparative example I5 according to the present disclosure.

As shown in FIG. 63 (wherein X axis represents the different groups, and Y axis represents the corresponding percentage values of inhibition rates), the inhibition rate of the combined application in a reverse sequential manner (NK cells being administered first and ddvv-RFP later) was about 21%, the inhibition rate of the single application of ddvv-RFP was about 11%, and the inhibition rate of single application of the NK cells was about 17%. The combined application in the reverse sequential manner did not show a synergistic effect.

Figure 64:
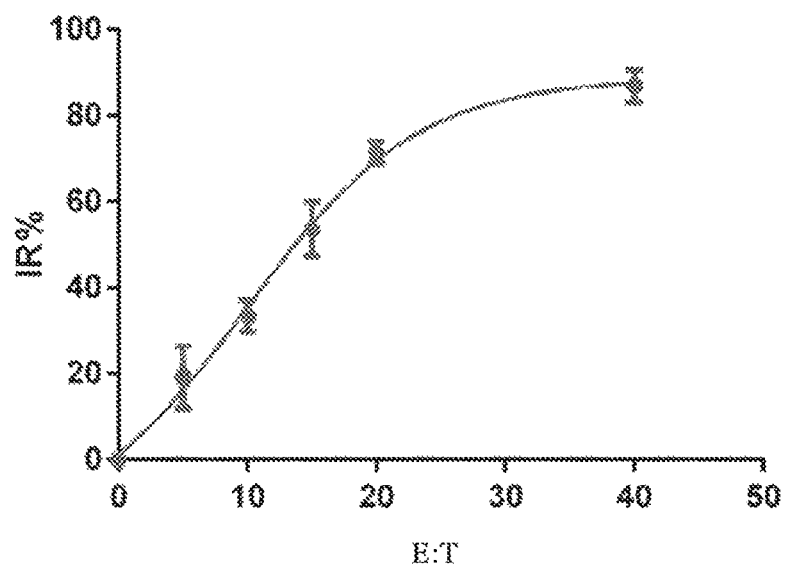
FIG. 64 shows the result of a dose-response experiment of NK cells against PANC-1 cells in Experimental example J1 according to the present disclosure.

J: Study on the Killing Effect of Combined Application of Oncolytic Vaccinia Virus and NK Cells Against PANC-1 Cells Experimental Example J1: Dose-Response Experiment of NK Cells Against PANC-1 Cells PANC-1 cells were plated into culture plates at 30% confluency and incubated in DMEM+10% FBS at 37° C. in 5% $CO_2$ for 48 hours. Then, the medium was replaced with fresh DMEM+10% FBS, and NK cells were added with the effector to target cell ratios (i.e., E:T, ratio of cell numbers) as follows: NK:PANC-1=40:1, 20:1, 15:1, 10:1, and 5:1, respectively. The killing process at each E:T ratio lasted for 48 hours with the cells being incubated at 37° C. in 5% $CO_2$. Afterwards, Trypan Blue Staining method was used for counting the living PANC-1 cells, and the killing rates of PANC-1 cells by NK cells were calculated relative to the control group in which no NK cells were added. FIG. 64 shows the dose-response curve (wherein X axis represents E:T ratio, and Y axis represents the percentage value of inhibition rate (IR)), which exhibits an inhibition rate of about 10% when E:T ratio is 3:1. This dosage was adopted as the dose level of NK cells to be used in the combined killing experiment.

Figure 65:
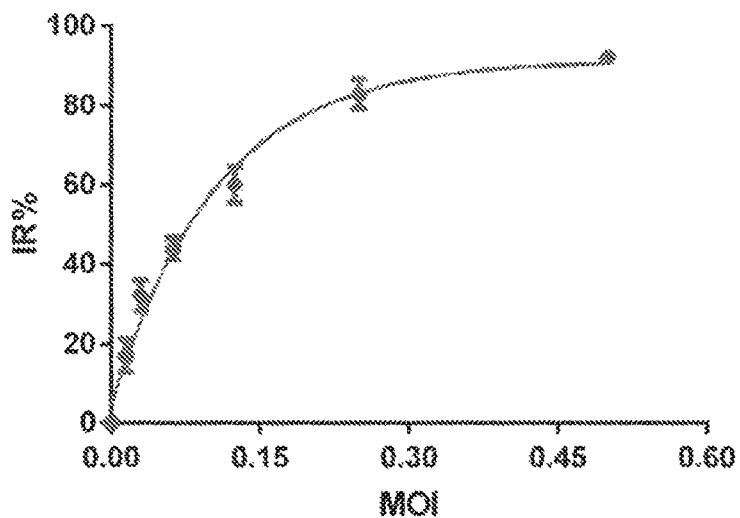
FIG. 65 shows the result of a dose-response experiment of ddvv-RFP against PANC-1 cells in Experimental example J2 according to the present disclosure.

Experimental Example J2: Dose-Response Experiment of ddvv-RFP Against PANC-1 Cells PANC-1 cells were plated into culture plates at 30% confluency and incubated in DMEM+10% FBS at 37° C. in 5% $CO_2$ for 24 hours. Then, the medium was replaced with fresh serum-free DMEM, and ddvv-RFP was added with MOI being MOI=0.5, 0.25, 0.125, 0.0625, 0.03 and 0.015, respectively. The infection process lasted for 6 hours with the cells being incubated at 37° C. In 5% $CO_2$, then the medium was removed, and the cells were washed with PBS. Then, DMEM+10% FBS was added, and the cells were further incubated to 72 hours. Afterwards, Trypan Blue Staining method was used for counting the living PANC-1 cells, and the killing rates of PANC-1 by ddvv-RFP were calculated relative to the control group in which no ddvv-RFP was added. FIG. 65 shows the dose-response curve (wherein X axis represents MOI, and Y axis represents the percentage value of inhibition rate (IR)), which exhibits an inhibition rate of about 58% when MOI is 0.1. This dosage was adopted as the dose level of ddvv-RFP to be used in the combined killing experiment.

Example J3: Combined Killing Experiment of ddvv-RFP and NK

It can be concluded from the above Experimental examples that the suitable dose level for the killing of ddvv-RFP against PANC-1 cells was the MOI being about 0.1; and the suitable dose level for the killing of NK cells against PANC-1 cells was the E:T ratio (i.e., NK:PANC-1) being about 3:1.

PANC-1 cells were plated into culture plates at 30% confluency and incubated in DMEM+10% FBS at 37° C. in 5% $CO_2$ for 24 hours. Then, the medium was replaced with serum-free DMEM, and ddvv-RFP was added (MOI=0.1). After a six-hour infection, the medium was replaced with DMEM+10% FBS, and the cells were incubated at 37° C. in 5% CO2 to 48 hours. The medium was replaced with fresh DMEM+10% FBS, and NK cells were added (E:T ratio (NK:PANC-1)=3:1), and the cells were further incubated for 48 hours. Dead cells and debris were washed off, and Trypan Blue Staining method was used for counting the remaining living PANC-1 cells. In the experiment, there were also a blank control group, in which none of the virus or NK cells were added to PANC-1 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 66:
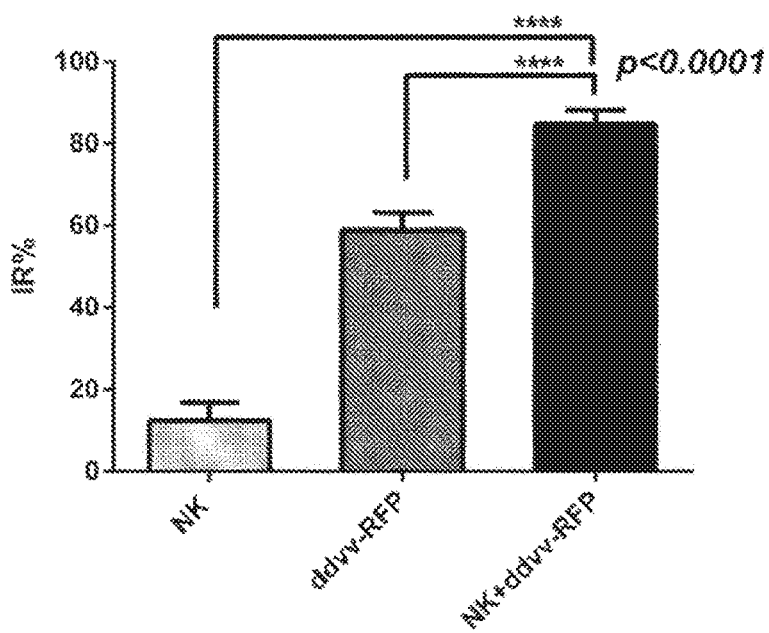
FIG. 66 shows the result of the combined killing experiment of ddvv-RFP and NK cells administered at an interval of 48 hours in Example J3 according to the present disclosure.

As shown in FIG. 66 (wherein X axis represents the different groups, and Y axis represents the corresponding percentage values of inhibition rates), the combined application of ddvv-RFP and NK cells (the oncolytic virus being administered first and the NK cells later) had significant synergistic killing effect against PANC-1 cells, and the synergistic inhibition rate was about 85%. However, in this experiment, the inhibition rate of single application of ddvv-RFP was about 59% and the inhibition rate of single application of the NK cells was about 13%.

Comparative Example J4: Simultaneous Combined Administration of the Drugs

PANC-1 cells were plated into culture plates at 30% confluency and incubated in DMEM+10% FBS at 37° C. in 5% $CO_2$ for 24 hours. Then, the medium was replaced with serum-free DMEM, and ddvv-RFP was added (MOI=0.1). After a six-hour infection, the medium was replaced with fresh DMEM+10% FBS, and NK cells were added (E:T ratio (NK:PANC-1)=3:1). The cells were further incubated to 96 hours, then dead cells and debris were washed off, and the remaining living PANC-1 cells were counted using Trypan Blue Staining method. In the experiment, there were also a blank control group, in which none of the virus or NK cells were added to PANC-1 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 67:
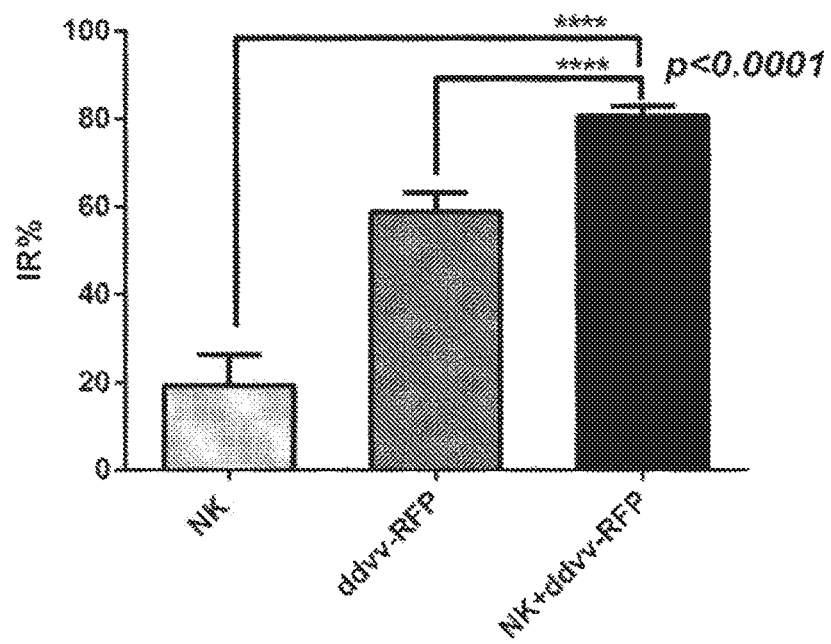
FIG. 67 shows the result of the simultaneous combined administration of ddvv-RFP and NK cells in Comparative example J4 according to the present disclosure.

As shown in FIG. 67 (wherein X axis represents the different groups, and Y axis represents the corresponding percentage values of inhibition rates), the inhibition rate of the single application of ddvv-RFP was about 59% and the inhibition rate of single application of the NK cells was about 19%. Compared to these single applications, the inhibition rate of combined use of NK cells and ddvv-RFP was increased, which was about 80%; however, no significant synergistic effect was shown (P>0.3).

The above results indicate that 1) the combined application of ddvv-RFP and NK cells has superior efficacy than the single application of either ddvv-RFP or NK cells; and 2) the timing of administration can significantly affect the efficacy of the combined application of ddvv-RFP and NK cells—when ddvv-RFP and NK cells were substantially administered simultaneously, the combined application did not show a significant synergistic effect; whereas when ddvv-RFP was administered first and NK cells later, the combined application showed a significant synergistic effect.

Comparative Example J5: Comparison Between Different Administration Sequences in Combined Application PANC-1 cells were plated into culture plates at 30% confluency and incubated in DMEM+10% FBS at 37° C. in 5% $CO_2$ for 24 hours. Then, the medium was replaced with fresh DMEM+10% FBS, and NK cells were added (E:T ratio (NK:PANC-1)=3:1). The cells were incubated at 37° C. in 5% $CO_2$ for 48 hours. Then, ddvv-RFP (MOI=0.1) was added without replacing the medium, and the cells were further incubated for 48 hours. Dead cells and debris were washed off, and Trypan Blue Staining method was used for counting the remaining living PANC-1 cells. In the experiment, there were also a blank control group, in which none of the virus or NK cells were added to PANC-1 cells; a ddvv-RFP group, in which ddvv-RFP was added at its corresponding time point but no NK cells were added; and a NK group, in which the NK cells were added at their corresponding time point but no ddvv-RFP was added. All the control groups underwent the corresponding medium replacement operations at corresponding times. All the experiments were repeated for over 3 times, and the averages were used for statistical analysis.

Figure 68:
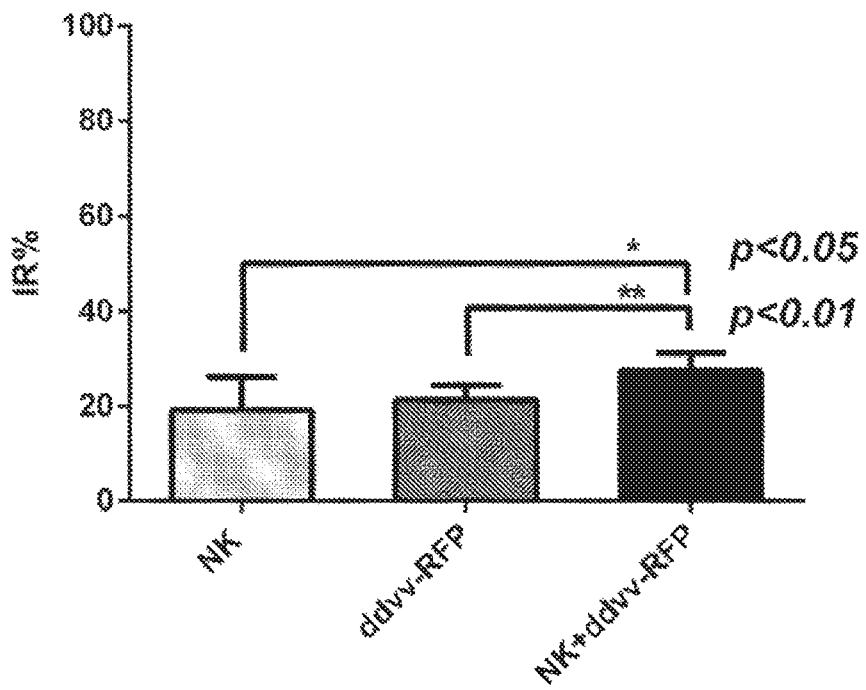
FIG. 68 shows the result of the combined administration of ddvv-RFP and NK cells at an interval of 48 hours in a reverse sequential manner in Comparative example J5 according to the present disclosure.

As shown in FIG. 68 (wherein X axis represents the different groups, and Y axis represents the corresponding percentage values of inhibition rates), the inhibition rate of the combined application in a reverse sequential manner (NK cells being administered first and ddvv-RFP later) was about 28%, the inhibition rate of the single application of ddvv-RFP was about 21%, and the inhibition rate of single application of the NK cells was about 19%. The combined application in the reverse sequential manner did not show a synergistic effect.

What is claimed is:
1. A method for treating a tumor and/or cancer, comprising the following steps in a sequential manner:
   1) administering an oncolytic virus to a tumor and/or cancer patient, wherein the oncolytic virus can selectively replicate in tumor cells; and
   2) 18 to 72 hours after the administration of the oncolytic virus, administering NK cells to the tumor and/or cancer patient;
   wherein the NK cells are not modified;
   wherein the method is conducted by only administrating the oncolytic virus and the NK cells as drugs.
2. The method of claim 1, wherein the oncolytic virus is selected from genetically mutated viruses with oncolytic abilities and wild-type viruses with oncolytic abilities.
3. The method of claim 1, wherein the oncolytic virus is selected from an oncolytic adenovirus, vaccinia virus, herpes simplex virus, measles virus, Semliki Forest virus, vesicular stomatitis virus, poliovirus, retrovirus, reovirus, Seneca Valley virus, Echo enterovirus, Coxsackie virus, Newcastle disease virus, and Maraba virus.

4. The method of claim 1, wherein the NK cells are selected from autologous NK cells and allogeneic NK cells.

5. The method of claim 4, wherein the NK cells are in vitro expanded autologous NK cells or in vitro expanded allogeneic NK cells.

6. The method of claim 1, wherein the tumor and/or cancer includes lung cancer, melanoma, head and neck cancer, liver cancer, brain cancer, colorectal cancer, bladder cancer, breast cancer, ovarian cancer, uterine cancer, cervical cancer, lymph cancer, gastric cancer, esophagus cancer, renal cancer, prostate cancer, pancreatic cancer, and leukemia.

7. The method of claim 1, wherein the oncolytic virus is given at a therapeutically effective dose once daily, consecutively for 1 to 6 days.

8. The method of claim 1, wherein the NK cells are given at a dose level ranging from $1\times10^7$ to $1\times10^{10}$ cells/day, once daily, consecutively for 1 to 6 days.

9. The method of claim 1, wherein the oncolytic virus is given at a therapeutically effective dose every other day, consecutively for 2 to 6 days.

10. The method of claim 1, wherein the NK cells are given at a dose level ranging from $1\times10^7$ to $1\times10^{10}$ cells/day, every other day, consecutively for 2 to 6 days.

11. The method of claim 1, wherein the oncolytic virus is administered via intratumoral injection or administered intravenously; and wherein the NK cells are administered intravenously.

12. The method of claim 1, wherein the oncolytic virus is an oncolytic adenovirus.

13. The method of claim 12, wherein E1 region and/or E3 region of the oncolytic adenovirus are/is genetically modified.

14. The method of claim 12, wherein the oncolytic adenovirus is selected from Onyx-015, H101, Ad5-yCD/mutTKSR39rep-hIL12, CG0070, DNX-2401, OBP-301, ONCOS-102, ColoAd1, VCN-01, and/or ProstAtak™.

15. The method of claim 1, wherein the oncolytic virus is an oncolytic adenovirus, and the dosage thereof ranges from $5\times10^7$ to $5\times10^{12}$ VP/day.

* * * * *